(12) United States Patent
Yunomura et al.

(10) Patent No.: US 9,388,433 B2
(45) Date of Patent: Jul. 12, 2016

(54) METHOD FOR PRODUCING POLYMER, METHOD FOR PRODUCING ORGANIC ACID, AND ORGANIC ACID-PRODUCING MICROORGANISM

(71) Applicant: MITSUBISHI CHEMICAL CORPORATION, Tokyo (JP)

(72) Inventors: Shuichi Yunomura, Yokohama (JP); Gou Takahashi, Yokkaichi (JP); Yoshiaki Mori, Yokkaichi (JP)

(73) Assignee: MITSUBISHI CHEMICAL CORPORATION, Tokyo (JP)

( * ) Notice: Subject to any disclaimer, the term of this patent is extended or adjusted under 35 U.S.C. 154(b) by 107 days.

(21) Appl. No.: 14/030,486

(22) Filed: Sep. 18, 2013

(65) Prior Publication Data

US 2014/0018511 A1 Jan. 16, 2014

Related U.S. Application Data

(63) Continuation of application No. PCT/JP2012/056935, filed on Mar. 16, 2012.

(30) Foreign Application Priority Data

Mar. 18, 2011 (JP) .................................. 2011-061412

(51) Int. Cl.
*C12P 7/46* (2006.01)
*C12P 7/40* (2006.01)
*C12N 1/20* (2006.01)
*C12N 9/12* (2006.01)
*C12N 9/88* (2006.01)

(52) U.S. Cl.
CPC ................ *C12P 7/46* (2013.01); *C12N 9/1205* (2013.01); *C12N 9/88* (2013.01); *C12Y 207/01029* (2013.01); *C12Y 402/01118* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 5,143,833 | A | 9/1992 | Datta |
| 5,143,834 | A | 9/1992 | Glassner et al. |
| 5,168,055 | A | 12/1992 | Datta et al. |
| 6,284,904 | B1 | 9/2001 | Ponnampalam |
| 2004/0002143 | A1 | 1/2004 | Asakura et al. |
| 2006/0003424 | A1 | 1/2006 | Asakura et al. |
| 2006/0172401 | A1 | 8/2006 | Yamagishi |
| 2006/0205048 | A1 | 9/2006 | Murase et al. |
| 2006/0281156 | A1 | 12/2006 | Aoyama et al. |
| 2007/0087423 | A1 | 4/2007 | Murakami et al. |
| 2009/0156779 | A1 | 6/2009 | Murase et al. |
| 2012/0329095 | A1 | 12/2012 | Yoshikawa et al. |
| 2013/0030215 | A1 | 1/2013 | Bui et al. |

FOREIGN PATENT DOCUMENTS

| | | |
|---|---|---|
| EP | 2 192 189 A1 | 6/2010 |
| JP | 2-283289 A | 11/1990 |
| JP | 11-113588 A | 4/1999 |
| JP | 11-196888 A | 7/1999 |
| JP | 2005-333886 A | 12/2005 |
| JP | 2006-000091 A | 1/2006 |
| JP | 2008-259451 A | 10/2008 |
| JP | 2010-100617 A | 5/2010 |
| WO | WO 00/18935 A1 | 4/2000 |
| WO | WO 2005/010182 A1 | 2/2005 |
| WO | WO 2005/021770 A1 | 3/2005 |
| WO | WO 2005/026349 A1 | 3/2005 |
| WO | WO 2009/025363 A1 | 2/2009 |
| WO | WO 2010/119927 A1 | 10/2010 |
| WO | WO 2011/059031 A1 | 5/2011 |
| WO | WO 2011/085311 A1 | 7/2011 |

OTHER PUBLICATIONS

Datsenko et al. One-step inactivation of chromosomal genes in *Escherichia coli* K-12 using PCR products, PNAS (Jun. 2000), 97(12): 6640-6645.*
U.S. Appl. No. 14/275,451, filed May 12, 2014, Yunomura, et al.
International Search Report issued Jun. 19, 2012 in PCT/JP2012/056935.
English translation of the International Preliminary Report on Patentability and Written Opinion issued Oct. 3, 2013 in PCT/JP2012/056935.
Ningqing Ran, et al., "Directed Evolution of 2-Keto-3-deoxy-6-*phosphoaalactonate* Aldolase to Replace 3-Deoxy-D-arabino-heptulosonic Acid 7-Phosphate Synthase" J. Am. Chem. Soc., vol. 129, 2007, pp. 6130-6139.
Ya-Jun Liu, et al., "*Corynebacterium glutamicum* Contains 3-Deoxy-D-Arabino-Heptulosonate7-Phosphate Synthases That Display Novel Biochemical Features" Applied and Environmental Microbiology, vol. 74, No. 17, Sep. 2008, pp. 5497-5503.
Haruhiko Teramoto, et al., "Regulation of Expression of Genes Involved in Quinate and Shikimate Utilization in *Corynebacterium glutamicum*" Applied and Environmental Microbiology, vol. 75, No. 11, Jun. 2009, pp. 3461-3468.
Karen M. Draths, et al., "Environmentally Compatible Sythesis of Adipic Acid from D-Glucose" J. Am. Chem. Soc., vol. 116, 1994, pp. 399-400.
David A. Elsemore, et al., "Unusual Ancestry of *Dehydratases* Associated with Quinate Catabolism in *Acinetobacter calcoaceticus*," Journal of Bacteriology, vol. 177, No. 20, Oct. 1995, pp. 5971-5978.
Extended European Search Report issued Feb. 3, 2014 in Patent Application No. 12760069.0.
Office Action issued Nov. 4, 2015 in Japanese Patent Application No. 2013-505959 (with English language translation).
Office Action as received in the corresponding Japanese Application No. 2013-505959 dated Mar. 8. 2016 w/English Translation.
Office Action as received in the corresponding European Patent Application No. 12760069.0 dated Apr. 15, 2016.

* cited by examiner

*Primary Examiner* — Iqbal H Chowdhury
(74) *Attorney, Agent, or Firm* — Oblon, McClelland, Maier & Neustadt, L.L.P

(57) ABSTRACT

The present invention provides a method of producing a polymer, which comprises the step of performing a polymerization reaction using, as a starting material, an organic acid obtained by allowing a microorganism or a treated cell thereof to act on an organic raw material, wherein said microorganism has an ability to produce an organic acid and has been modified so as to produce less aromatic carboxylic acid as compared to an unmodified strain.

22 Claims, 4 Drawing Sheets

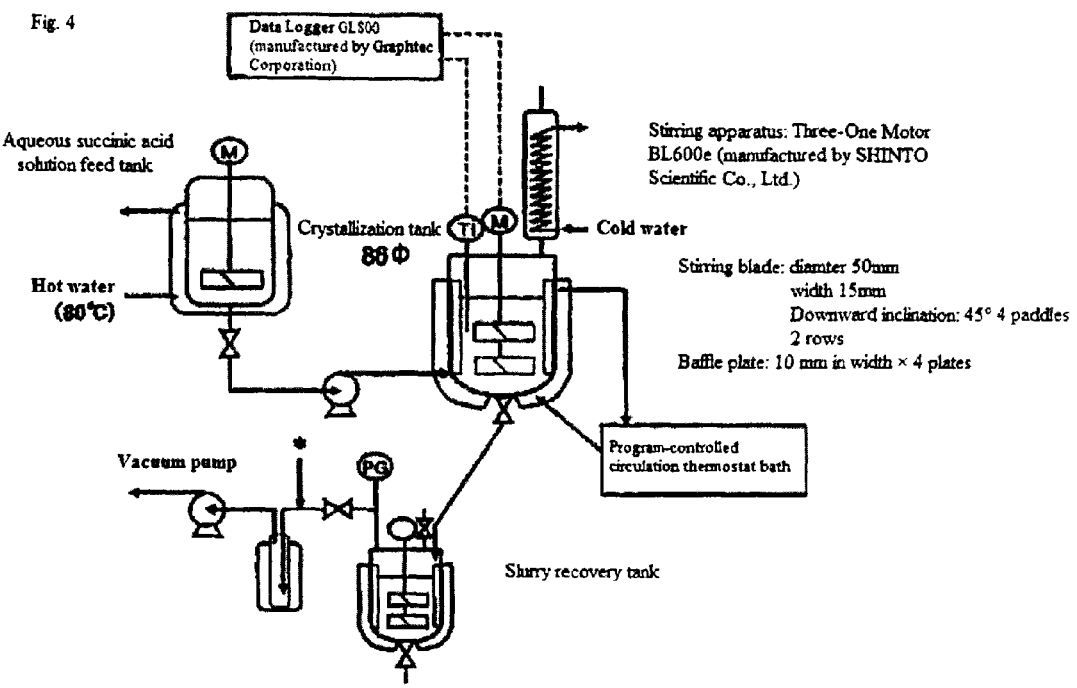

SEQUENCE LISTING

```
<160> NUMBER OF SEQ ID NOS: 27

<210> SEQ ID NO 1
<211> LENGTH: 25
<212> TYPE: DNA
<213> ORGANISM: Artificial Sequence
<220> FEATURE:
<223> OTHER INFORMATION: Synthetic primer

<400> SEQUENCE: 1
gtccggagct cttgctgaaa agctg                                           25

<210> SEQ ID NO 2
<211> LENGTH: 34
<212> TYPE: DNA
<213> ORGANISM: Artificial Sequence
<220> FEATURE:
<223> OTHER INFORMATION: Synthetic primer
```

```
<400> SEQUENCE: 2
cagccactca acacggtggt gacgcgacca ggac                                    34

<210> SEQ ID NO 3
<211> LENGTH: 33
<212> TYPE: DNA
<213> ORGANISM: Artificial Sequence
<220> FEATURE:
<223> OTHER INFORMATION: Synthetic primer

<400> SEQUENCE: 3
caccgtgttg agtggctgcc ggaattcggc gtc                                     33

<210> SEQ ID NO 4
<211> LENGTH: 24
<212> TYPE: DNA
<213> ORGANISM: Artificial Sequence
<220> FEATURE:
<223> OTHER INFORMATION: Synthetic primer

<400> SEQUENCE: 4
ctagttgggg attccccgct cgag                                               24

<210> SEQ ID NO 5
<211> LENGTH: 24
<212> TYPE: DNA
<213> ORGANISM: Artificial Sequence
<220> FEATURE:
<223> OTHER INFORMATION: Synthetic primer

<400> SEQUENCE: 5
acacaggaaa cagctatgac catg                                               24

<210> SEQ ID NO 6
<211> LENGTH: 21
<212> TYPE: DNA
<213> ORGANISM: Artificial Sequence
<220> FEATURE:
<223> OTHER INFORMATION: Synthetic primer

<400> SEQUENCE: 6
gttttcccag tcacgacgtt g                                                  21

<210> SEQ ID NO 7
<211> LENGTH: 1101
<212> TYPE: DNA
<213> ORGANISM: Corynebacterium glutamicum
<220> FEATURE:
<221> NAME/KEY: CDS
<222> LOCATION: (1)..(1098)

<400> SEQUENCE: 7 atg agt tct cca gtc tca ctc gaa aac gcg gcg tca acc agc aac aag         48
Met Ser Ser Pro Val Ser Leu Glu Asn Ala Ala Ser Thr Ser Asn Lys
1               5                   10                  15 cgc gtc gtg gct ttc cac gag ctg cct agc cct aca gat ctc atc gcc         96
Arg Val Val Ala Phe His Glu Leu Pro Ser Pro Thr Asp Leu Ile Ala
            20                  25                  30 gca aac cca ctg aca cca aag cag gct tcc aag gtg gag cag gat cgc        144
Ala Asn Pro Leu Thr Pro Lys Gln Ala Ser Lys Val Glu Gln Asp Arg
        35                  40                  45 cag gac atc gct gat atc ttc gct ggc gac gat gac cgc ctc gtt gtc        192
Gln Asp Ile Ala Asp Ile Phe Ala Gly Asp Asp Asp Arg Leu Val Val
    50                  55                  60
```

```
gtt gtg gga cct tgc tca gtt cac gat cct gaa gca gcc atc gat tac    240
Val Val Gly Pro Cys Ser Val His Asp Pro Glu Ala Ala Ile Asp Tyr
65              70                  75                  80 gca aac cgc ctg gct ccg ctg gca aag cgc ctt gac cag gac ctc aag    288
Ala Asn Arg Leu Ala Pro Leu Ala Lys Arg Leu Asp Gln Asp Leu Lys
                85                  90                  95 att gtc atg cgc gtg tac ttc gag aag cct cgc acc acc gtc ggt tgg    336
Ile Val Met Arg Val Tyr Phe Glu Lys Pro Arg Thr Thr Val Gly Trp
            100                 105                 110 aag gga ttg atc aac gat cct cac ctc aac gaa acc tac gac atc cca    384
Lys Gly Leu Ile Asn Asp Pro His Leu Asn Glu Thr Tyr Asp Ile Pro
        115                 120                 125 gag ggc ttg cgc att gcg cgc aaa gtg ctt atc gac gtt gtg aac ctt    432
Glu Gly Leu Arg Ile Ala Arg Lys Val Leu Ile Asp Val Val Asn Leu
    130                 135                 140 gat ctc cca gtc ggc tgc gaa ttc ctc gaa cca aac agc cct cag tac    480
Asp Leu Pro Val Gly Cys Glu Phe Leu Glu Pro Asn Ser Pro Gln Tyr
145                 150                 155                 160 tac gcc gac act gtc gca tgg gga gca atc ggc gct cgt acc acc gaa    528
Tyr Ala Asp Thr Val Ala Trp Gly Ala Ile Gly Ala Arg Thr Thr Glu
                165                 170                 175 tct cag gtg cac cgc cag ctg gct tct ggg atg tct atg cca att ggt    576
Ser Gln Val His Arg Gln Leu Ala Ser Gly Met Ser Met Pro Ile Gly
            180                 185                 190 ttc aag aac gga act gac gga aac atc cag gtt gca gtc gac gcg gta    624
Phe Lys Asn Gly Thr Asp Gly Asn Ile Gln Val Ala Val Asp Ala Val
        195                 200                 205 cag gct gcc cag aac cca cac ttc ttc ttc gga acc tcc gac gac ggc    672
Gln Ala Ala Gln Asn Pro His Phe Phe Phe Gly Thr Ser Asp Asp Gly
    210                 215                 220 gcg ctg agc gtc gtg gag acc gca ggc aat agc aac tcc cac atc att    720
Ala Leu Ser Val Val Glu Thr Ala Gly Asn Ser Asn Ser His Ile Ile
225                 230                 235                 240 ttg cgc ggc ggt acc tcc ggc ccg aat cat gat gca gct tcg gtg gag    768
Leu Arg Gly Gly Thr Ser Gly Pro Asn His Asp Ala Ala Ser Val Glu
                245                 250                 255 gcc gtc gtc gag aag ctt ggt gaa aac gct cgt ctc atg atc gat gct    816
Ala Val Val Glu Lys Leu Gly Glu Asn Ala Arg Leu Met Ile Asp Ala
            260                 265                 270 tcc cat gct aac tcc ggc aag gat cat atc cga cag gtt gag gtt gtt    864
Ser His Ala Asn Ser Gly Lys Asp His Ile Arg Gln Val Glu Val Val
        275                 280                 285 cgt gaa atc gca gag cag att tct ggc ggt tct gaa gct gtg gct gga    912
Arg Glu Ile Ala Glu Gln Ile Ser Gly Gly Ser Glu Ala Val Ala Gly
    290                 295                 300 atc atg att gag tcc ttc ctc gtt ggt ggc gca cag aac ctt gat cct    960
Ile Met Ile Glu Ser Phe Leu Val Gly Gly Ala Gln Asn Leu Asp Pro
305                 310                 315                 320 gcg aaa ttg cgc atc aat ggc ggt gaa ggc ctg gtg tac gga cag tct   1008
Ala Lys Leu Arg Ile Asn Gly Gly Glu Gly Leu Val Tyr Gly Gln Ser
                325                 330                 335 gtg acc gat aag tgc atc gat att gac acc acc atc gat ttg ctc gct   1056
Val Thr Asp Lys Cys Ile Asp Ile Asp Thr Thr Ile Asp Leu Leu Ala
            340                 345                 350 gag ctg gcc gca gca gta agg gaa cgc cga gca gca gcc aag taa       1101
Glu Leu Ala Ala Ala Val Arg Glu Arg Arg Ala Ala Ala Lys
        355                 360                 365
```

<210> SEQ ID NO 8

<211> LENGTH: 366
<212> TYPE: PRT
<213> ORGANISM: Corynebacterium glutamicum

<400> SEQUENCE: 8

Met Ser Ser Pro Val Ser Leu Glu Asn Ala Ala Ser Thr Ser Asn Lys
1               5                   10                  15

Arg Val Val Ala Phe His Glu Leu Pro Ser Pro Thr Asp Leu Ile Ala
            20                  25                  30

Ala Asn Pro Leu Thr Pro Lys Gln Ala Ser Lys Val Glu Gln Asp Arg
        35                  40                  45

Gln Asp Ile Ala Asp Ile Phe Ala Gly Asp Asp Arg Leu Val Val
    50                  55                  60

Val Val Gly Pro Cys Ser Val His Asp Pro Glu Ala Ala Ile Asp Tyr
65                  70                  75                  80

Ala Asn Arg Leu Ala Pro Leu Ala Lys Arg Leu Asp Gln Asp Leu Lys
                85                  90                  95

Ile Val Met Arg Val Tyr Phe Glu Lys Pro Arg Thr Thr Val Gly Trp
            100                 105                 110

Lys Gly Leu Ile Asn Asp Pro His Leu Asn Glu Thr Tyr Asp Ile Pro
        115                 120                 125

Glu Gly Leu Arg Ile Ala Arg Lys Val Leu Ile Asp Val Val Asn Leu
    130                 135                 140

Asp Leu Pro Val Gly Cys Glu Phe Leu Glu Pro Asn Ser Pro Gln Tyr
145                 150                 155                 160

Tyr Ala Asp Thr Val Ala Trp Gly Ala Ile Gly Ala Arg Thr Thr Glu
                165                 170                 175

Ser Gln Val His Arg Gln Leu Ala Ser Gly Met Ser Met Pro Ile Gly
            180                 185                 190

Phe Lys Asn Gly Thr Asp Gly Asn Ile Gln Val Ala Val Asp Ala Val
        195                 200                 205

Gln Ala Ala Gln Asn Pro His Phe Phe Phe Gly Thr Ser Asp Asp Gly
    210                 215                 220

Ala Leu Ser Val Val Glu Thr Ala Gly Asn Ser Asn Ser His Ile Ile
225                 230                 235                 240

Leu Arg Gly Gly Thr Ser Gly Pro Asn His Asp Ala Ala Ser Val Glu
                245                 250                 255

Ala Val Val Glu Lys Leu Gly Glu Asn Ala Arg Leu Met Ile Asp Ala
            260                 265                 270

Ser His Ala Asn Ser Gly Lys Asp His Ile Arg Gln Val Glu Val Val
        275                 280                 285

Arg Glu Ile Ala Glu Gln Ile Ser Gly Gly Ser Glu Ala Val Ala Gly
    290                 295                 300

Ile Met Ile Glu Ser Phe Leu Val Gly Gly Ala Gln Asn Leu Asp Pro
305                 310                 315                 320

Ala Lys Leu Arg Ile Asn Gly Gly Glu Gly Leu Val Tyr Gly Gln Ser
                325                 330                 335

Val Thr Asp Lys Cys Ile Asp Ile Asp Thr Thr Ile Asp Leu Leu Ala
            340                 345                 350

Glu Leu Ala Ala Ala Val Arg Glu Arg Ala Ala Lys
        355                 360                 365

<210> SEQ ID NO 9
<211> LENGTH: 1401
<212> TYPE: DNA

<213> ORGANISM: Corynebacterium glutamicum
<220> FEATURE:
<221> NAME/KEY: CDS
<222> LOCATION: (1)..(1398)

<400> SEQUENCE: 9

```
atg aat agg ggt gtg agt tgg aca gtt gat atc cct aaa gaa gtt ctc      48
Met Asn Arg Gly Val Ser Trp Thr Val Asp Ile Pro Lys Glu Val Leu
1               5                   10                  15 cct gat ttg cca cca ttg cca gaa ggc atg cag cag cag ttc gag gac      96
Pro Asp Leu Pro Pro Leu Pro Glu Gly Met Gln Gln Gln Phe Glu Asp
            20                  25                  30 acc att tcc cgt gac gct aag cag caa cct acg tgg gat cgt gca cag     144
Thr Ile Ser Arg Asp Ala Lys Gln Gln Pro Thr Trp Asp Arg Ala Gln
        35                  40                  45 gca gaa aac gtg cgc aag atc ctt gag tcg gtt cct cca atc gtt gtt     192
Ala Glu Asn Val Arg Lys Ile Leu Glu Ser Val Pro Pro Ile Val Val
    50                  55                  60 gcc cct gag gta ctt gag ctg aag cag aag ctt gct gat gtt gct aac     240
Ala Pro Glu Val Leu Glu Leu Lys Gln Lys Leu Ala Asp Val Ala Asn
65                  70                  75                  80 ggt aag gcc ttc ctc ttg cag ggt ggt gac tgt gcg gaa act ttc gag     288
Gly Lys Ala Phe Leu Leu Gln Gly Gly Asp Cys Ala Glu Thr Phe Glu
                85                  90                  95 tca aac acc gag ccg cac att cgc gcc aac gta aag act ctg ctg cag     336
Ser Asn Thr Glu Pro His Ile Arg Ala Asn Val Lys Thr Leu Leu Gln
            100                 105                 110 atg gca gtt gtt ttg acc tac ggt gca tcc act ccc gtg atc aag atg     384
Met Ala Val Val Leu Thr Tyr Gly Ala Ser Thr Pro Val Ile Lys Met
        115                 120                 125 gct cgt att gct ggt cag tac gca aag cct cgc tct tct gat ttg gat     432
Ala Arg Ile Ala Gly Gln Tyr Ala Lys Pro Arg Ser Ser Asp Leu Asp
    130                 135                 140 gga aat ggt ctg cca aac tac cgt ggc gat atc gtc aac ggt gtg gag     480
Gly Asn Gly Leu Pro Asn Tyr Arg Gly Asp Ile Val Asn Gly Val Glu
145                 150                 155                 160 gca acc cct gag gct cgt cgc cac gat cct gcc cgc atg atc cgt gct     528
Ala Thr Pro Glu Ala Arg Arg His Asp Pro Ala Arg Met Ile Arg Ala
                165                 170                 175 tac gct aac gct tct gct gcg atg aac ttg gtg cgc gcg ctc acc agc     576
Tyr Ala Asn Ala Ser Ala Ala Met Asn Leu Val Arg Ala Leu Thr Ser
            180                 185                 190 tct ggc acc gct gat ctt tac cgt ctc agc gag tgg aac cgc gag ttc     624
Ser Gly Thr Ala Asp Leu Tyr Arg Leu Ser Glu Trp Asn Arg Glu Phe
        195                 200                 205 gtt gcg aac tcc cca gct ggt gca cgc tac gag gct ctt gct cgt gag     672
Val Ala Asn Ser Pro Ala Gly Ala Arg Tyr Glu Ala Leu Ala Arg Glu
    210                 215                 220 atc gac tcc ggt ctg cgc ttc atg gaa gca tgt ggc gtg tcc gat gag     720
Ile Asp Ser Gly Leu Arg Phe Met Glu Ala Cys Gly Val Ser Asp Glu
225                 230                 235                 240 tcc ctg cgc gct gca gat att tac tgc tcc cac gag gca ctt ctc gtg     768
Ser Leu Arg Ala Ala Asp Ile Tyr Cys Ser His Glu Ala Leu Leu Val
                245                 250                 255 gat tac gag cgc tcc atg ctg cgt ctt gca acc gat gag gaa ggc aac     816
Asp Tyr Glu Arg Ser Met Leu Arg Leu Ala Thr Asp Glu Glu Gly Asn
            260                 265                 270 gag gaa ctt tac gat ctt tca gct cac cag ctg tgg atc ggc gag cgc     864
Glu Glu Leu Tyr Asp Leu Ser Ala His Gln Leu Trp Ile Gly Glu Arg
        275                 280                 285
```

```
acc cgc ggt atg gat gat ttc cat gtg aac ttc gca tcc atg atc tct    912
Thr Arg Gly Met Asp Asp Phe His Val Asn Phe Ala Ser Met Ile Ser
290                 295                 300 aac cca atc ggc atc aag att ggt cct ggt atc acc cct gaa gag gct    960
Asn Pro Ile Gly Ile Lys Ile Gly Pro Gly Ile Thr Pro Glu Glu Ala
305                 310                 315                 320 gtt gca tac gct gac aag ctc gat ccg aac ttc gag cct ggc cgt ttg   1008
Val Ala Tyr Ala Asp Lys Leu Asp Pro Asn Phe Glu Pro Gly Arg Leu
            325                 330                 335 acc atc gtt gct cgc atg ggc cac gac aag gtt cgc tcc gta ctt cct   1056
Thr Ile Val Ala Arg Met Gly His Asp Lys Val Arg Ser Val Leu Pro
            340                 345                 350 ggt gtt atc cag gct gtt gag gca tcc gga cac aag gtt att tgg cag   1104
Gly Val Ile Gln Ala Val Glu Ala Ser Gly His Lys Val Ile Trp Gln
            355                 360                 365 tcc gat ccg atg cac ggc aat acc ttc acc gca tcc aat ggc tac aag   1152
Ser Asp Pro Met His Gly Asn Thr Phe Thr Ala Ser Asn Gly Tyr Lys
370                 375                 380 acc cgt cac ttc gac aag gtt atc gat gag gtc cag ggc ttc ttc gag   1200
Thr Arg His Phe Asp Lys Val Ile Asp Glu Val Gln Gly Phe Phe Glu
385                 390                 395                 400 gtc cac cgc gca ttg ggc acc cac cca ggc gga atc cac att gag ttc   1248
Val His Arg Ala Leu Gly Thr His Pro Gly Gly Ile His Ile Glu Phe
            405                 410                 415 act ggt gaa gat gtc acc gag tgc ctc ggt ggc gct gaa gac atc acc   1296
Thr Gly Glu Asp Val Thr Glu Cys Leu Gly Gly Ala Glu Asp Ile Thr
            420                 425                 430 gat gtt gat ctg cca ggc cgc tac gag tcc gca tgc gat cct cgc ctg   1344
Asp Val Asp Leu Pro Gly Arg Tyr Glu Ser Ala Cys Asp Pro Arg Leu
            435                 440                 445 aac act cag cag tct ttg gag ttg gct ttc ctc gtt gca gaa atg ctg   1392
Asn Thr Gln Gln Ser Leu Glu Leu Ala Phe Leu Val Ala Glu Met Leu
            450                 455                 460 cgt aac taa                                                        1401
Arg Asn
465

<210> SEQ ID NO 10
<211> LENGTH: 466
<212> TYPE: PRT
<213> ORGANISM: Corynebacterium glutamicum

<400> SEQUENCE: 10

Met Asn Arg Gly Val Ser Trp Thr Val Asp Ile Pro Lys Glu Val Leu
1               5                   10                  15

Pro Asp Leu Pro Pro Leu Pro Glu Gly Met Gln Gln Gln Phe Glu Asp
            20                  25                  30

Thr Ile Ser Arg Asp Ala Lys Gln Gln Pro Thr Trp Asp Arg Ala Gln
        35                  40                  45

Ala Glu Asn Val Arg Lys Ile Leu Glu Ser Val Pro Pro Ile Val Val
    50                  55                  60

Ala Pro Glu Val Leu Glu Leu Lys Gln Lys Leu Ala Asp Val Ala Asn
65                  70                  75                  80

Gly Lys Ala Phe Leu Leu Gln Gly Gly Asp Cys Ala Glu Thr Phe Glu
                85                  90                  95

Ser Asn Thr Glu Pro His Ile Arg Ala Asn Val Lys Thr Leu Leu Gln
            100                 105                 110

Met Ala Val Val Leu Thr Tyr Gly Ala Ser Thr Pro Val Ile Lys Met
        115                 120                 125
```

Ala Arg Ile Ala Gly Gln Tyr Ala Lys Pro Arg Ser Ser Asp Leu Asp
            130                 135                 140

Gly Asn Gly Leu Pro Asn Tyr Arg Gly Asp Ile Val Asn Gly Val Glu
145                 150                 155                 160

Ala Thr Pro Glu Ala Arg Arg His Asp Pro Ala Arg Met Ile Arg Ala
                165                 170                 175

Tyr Ala Asn Ala Ser Ala Ala Met Asn Leu Val Arg Ala Leu Thr Ser
                180                 185                 190

Ser Gly Thr Ala Asp Leu Tyr Arg Leu Ser Glu Trp Asn Arg Glu Phe
            195                 200                 205

Val Ala Asn Ser Pro Ala Gly Ala Arg Tyr Glu Ala Leu Ala Arg Glu
210                 215                 220

Ile Asp Ser Gly Leu Arg Phe Met Glu Ala Cys Gly Val Ser Asp Glu
225                 230                 235                 240

Ser Leu Arg Ala Ala Asp Ile Tyr Cys Ser His Glu Ala Leu Leu Val
                245                 250                 255

Asp Tyr Glu Arg Ser Met Leu Arg Leu Ala Thr Asp Glu Glu Gly Asn
            260                 265                 270

Glu Glu Leu Tyr Asp Leu Ser Ala His Gln Leu Trp Ile Gly Glu Arg
        275                 280                 285

Thr Arg Gly Met Asp Asp Phe His Val Asn Phe Ala Ser Met Ile Ser
290                 295                 300

Asn Pro Ile Gly Ile Lys Ile Gly Pro Gly Ile Thr Pro Glu Glu Ala
305                 310                 315                 320

Val Ala Tyr Ala Asp Lys Leu Asp Pro Asn Phe Glu Pro Gly Arg Leu
                325                 330                 335

Thr Ile Val Ala Arg Met Gly His Asp Lys Val Arg Ser Val Leu Pro
            340                 345                 350

Gly Val Ile Gln Ala Val Glu Ala Ser Gly His Lys Val Ile Trp Gln
        355                 360                 365

Ser Asp Pro Met His Gly Asn Thr Phe Thr Ala Ser Asn Gly Tyr Lys
370                 375                 380

Thr Arg His Phe Asp Lys Val Ile Asp Glu Val Gln Gly Phe Phe Glu
385                 390                 395                 400

Val His Arg Ala Leu Gly Thr His Pro Gly Gly Ile His Ile Glu Phe
                405                 410                 415

Thr Gly Glu Asp Val Thr Glu Cys Leu Gly Gly Ala Glu Asp Ile Thr
            420                 425                 430

Asp Val Asp Leu Pro Gly Arg Tyr Glu Ser Ala Cys Asp Pro Arg Leu
        435                 440                 445

Asn Thr Gln Gln Ser Leu Glu Leu Ala Phe Leu Val Ala Glu Met Leu
450                 455                 460

Arg Asn
465

<210> SEQ ID NO 11
<211> LENGTH: 1098
<212> TYPE: DNA
<213> ORGANISM: Corynebacterium glutamicum
<220> FEATURE:
<221> NAME/KEY: CDS
<222> LOCATION: (1)..(1095)

<400> SEQUENCE: 11 atg agc gca gcg cag att ttc aac acc gtc cac gtc aat gga tct tcc      48

```
Met Ser Ala Ala Gln Ile Phe Asn Thr Val His Val Asn Gly Ser Ser
1               5                   10                  15
```

| | |
|---|---:|
| ccc tat gat gtc cac att ggt tcc ggc ctc aac gag ctc att gtt cag<br>Pro Tyr Asp Val His Ile Gly Ser Gly Leu Asn Glu Leu Ile Val Gln<br>                20                      25                  30 | 96 |
| cgc gca gcg gaa tca ggc gcg gag cag gta gcg att ttg cac cag ccc<br>Arg Ala Ala Glu Ser Gly Ala Glu Gln Val Ala Ile Leu His Gln Pro<br>                35                      40                  45 | 144 |
| agc atg gat gac att gca tcc gag ttg gat gca gca cta gtc gct gct<br>Ser Met Asp Asp Ile Ala Ser Glu Leu Asp Ala Ala Leu Val Ala Ala<br>      50                      55                      60 | 192 |
| ggt ttg aag gtc ctg cac ctt aat gtt ccc gat gcg gaa aac ggc aag<br>Gly Leu Lys Val Leu His Leu Asn Val Pro Asp Ala Glu Asn Gly Lys<br>65                      70                      75                  80 | 240 |
| tcc ttg gaa gta gcg ggg cag tgc tgg gat gaa ttg ggt ggc gca gca<br>Ser Leu Glu Val Ala Gly Gln Cys Trp Asp Glu Leu Gly Gly Ala Ala<br>                        85                      90                  95 | 288 |
| ttc ggc cgc cgc gat atc gtc atc gga ctt ggt ggc ggt gct gcc aca<br>Phe Gly Arg Arg Asp Ile Val Ile Gly Leu Gly Gly Gly Ala Ala Thr<br>                  100                     105                 110 | 336 |
| gat ctc gcg gga ttc gtc gct gct gcg tgg atg cgt ggc gtg cgc gtc<br>Asp Leu Ala Gly Phe Val Ala Ala Ala Trp Met Arg Gly Val Arg Val<br>         115                     120                 125 | 384 |
| att cag gtt cca acc acc ttg ttg gcc atg gtg gac gct gcg gtg ggc<br>Ile Gln Val Pro Thr Thr Leu Leu Ala Met Val Asp Ala Ala Val Gly<br>130                     135                     140 | 432 |
| ggc aag act ggc atc aat acc gcc gca ggc aag aac ctt gtg ggc gcg<br>Gly Lys Thr Gly Ile Asn Thr Ala Ala Gly Lys Asn Leu Val Gly Ala<br>145                     150                     155                 160 | 480 |
| ttc cac gag cct gac gca gta ttc att gac acc gaa cgc cta gcc acc<br>Phe His Glu Pro Asp Ala Val Phe Ile Asp Thr Glu Arg Leu Ala Thr<br>                  165                     170                 175 | 528 |
| ctg cct gac gcg gaa atc atc gcg gga tcc gcc gaa atc atc aaa act<br>Leu Pro Asp Ala Glu Ile Ile Ala Gly Ser Ala Glu Ile Ile Lys Thr<br>             180                     185                 190 | 576 |
| ggt ttc atc gcc gac cca gaa atc ctg cgc ctt tac gaa act gat ccc<br>Gly Phe Ile Ala Asp Pro Glu Ile Leu Arg Leu Tyr Glu Thr Asp Pro<br>         195                     200                 205 | 624 |
| gca gcc tgc ctg aag aaa gaa gtc gaa ggc tcc cac cta cct gaa ctg<br>Ala Ala Cys Leu Lys Lys Glu Val Glu Gly Ser His Leu Pro Glu Leu<br>210                     215                     220 | 672 |
| att tgg cgc tcc gtc acc gtc aag ggc tcc gtg gtc ggc caa gac ctc<br>Ile Trp Arg Ser Val Thr Val Lys Gly Ser Val Val Gly Gln Asp Leu<br>225                     230                     235                 240 | 720 |
| aaa gaa tct agc ctg cgc gaa atc ctc aac tac gga cac acc ttt gcc<br>Lys Glu Ser Ser Leu Arg Glu Ile Leu Asn Tyr Gly His Thr Phe Ala<br>             245                     250                 255 | 768 |
| cac gcc gtc gaa ctc cgc gaa aac ttc cgc tgg cgc cac ggc aat gcc<br>His Ala Val Glu Leu Arg Glu Asn Phe Arg Trp Arg His Gly Asn Ala<br>         260                     265                 270 | 816 |
| gtt gca gtg ggc atg atg ttc atc gct aac ctc tcc cac aag ctc ggg<br>Val Ala Val Gly Met Met Phe Ile Ala Asn Leu Ser His Lys Leu Gly<br>             275                     280                 285 | 864 |
| ctt atc gac gcg ccc ctc ctc gag cgc cac cgc tca atc ctg gcg gcc<br>Leu Ile Asp Ala Pro Leu Leu Glu Arg His Arg Ser Ile Leu Ala Ala<br>290                     295                     300 | 912 |
| atc ggt ctg ccc act tcc tac gaa ggc gga gcc ttc gac gag ctt tac<br>Ile Gly Leu Pro Thr Ser Tyr Glu Gly Gly Ala Phe Asp Glu Leu Tyr<br>305                     310                     315                 320 | 960 |

```
gac ggc atg acc cgc gac aag aaa aac cgc gac ggc aac atc cgc ttc      1008
Asp Gly Met Thr Arg Asp Lys Lys Asn Arg Asp Gly Asn Ile Arg Phe
            325                 330                 335 gtc gca ctg acc gcc gtg ggc gag gtt acc cgc att gag ggg ccc tca      1056
Val Ala Leu Thr Ala Val Gly Glu Val Thr Arg Ile Glu Gly Pro Ser
            340                 345                 350 aaa caa gat tta cag agt gct tat gag gca atc agc cac taa              1098
Lys Gln Asp Leu Gln Ser Ala Tyr Glu Ala Ile Ser His
            355                 360             365

<210> SEQ ID NO 12
<211> LENGTH: 365
<212> TYPE: PRT
<213> ORGANISM: Corynebacterium glutamicum

<400> SEQUENCE: 12

Met Ser Ala Ala Gln Ile Phe Asn Thr Val His Val Asn Gly Ser Ser
1               5                   10                  15

Pro Tyr Asp Val His Ile Gly Ser Gly Leu Asn Glu Leu Ile Val Gln
            20                  25                  30

Arg Ala Glu Ser Gly Ala Glu Gln Val Ala Ile Leu His Gln Pro
        35                  40                  45

Ser Met Asp Asp Ile Ala Ser Glu Leu Asp Ala Ala Leu Val Ala Ala
    50                  55                  60

Gly Leu Lys Val Leu His Leu Asn Val Pro Asp Ala Glu Asn Gly Lys
65                  70                  75                  80

Ser Leu Glu Val Ala Gly Gln Cys Trp Asp Glu Leu Gly Gly Ala Ala
                85                  90                  95

Phe Gly Arg Arg Asp Ile Val Ile Gly Leu Gly Gly Ala Ala Thr
            100                 105                 110

Asp Leu Ala Gly Phe Val Ala Ala Trp Met Arg Gly Val Arg Val
            115                 120                 125

Ile Gln Val Pro Thr Thr Leu Leu Ala Met Val Asp Ala Ala Val Gly
        130                 135                 140

Gly Lys Thr Gly Ile Asn Thr Ala Ala Gly Lys Asn Leu Val Gly Ala
145                 150                 155                 160

Phe His Glu Pro Asp Ala Val Phe Ile Asp Thr Glu Arg Leu Ala Thr
                165                 170                 175

Leu Pro Asp Ala Glu Ile Ile Ala Gly Ser Ala Glu Ile Ile Lys Thr
            180                 185                 190

Gly Phe Ile Ala Asp Pro Glu Ile Leu Arg Leu Tyr Glu Thr Asp Pro
        195                 200                 205

Ala Ala Cys Leu Lys Lys Glu Val Glu Gly Ser His Leu Pro Glu Leu
    210                 215                 220

Ile Trp Arg Ser Val Thr Val Lys Gly Ser Val Val Gly Gln Asp Leu
225                 230                 235                 240

Lys Glu Ser Ser Leu Arg Glu Ile Leu Asn Tyr Gly His Thr Phe Ala
                245                 250                 255

His Ala Val Glu Leu Arg Glu Asn Phe Arg Trp Arg His Gly Asn Ala
            260                 265                 270

Val Ala Val Gly Met Met Phe Ile Ala Asn Leu Ser His Lys Leu Gly
        275                 280                 285

Leu Ile Asp Ala Pro Leu Leu Glu Arg His Arg Ser Ile Leu Ala Ala
    290                 295                 300

Ile Gly Leu Pro Thr Ser Tyr Glu Gly Gly Ala Phe Asp Glu Leu Tyr
305                 310                 315                 320
```

```
Asp Gly Met Thr Arg Asp Lys Lys Asn Arg Asp Gly Asn Ile Arg Phe
                325                 330                 335

Val Ala Leu Thr Ala Val Gly Glu Val Thr Arg Ile Glu Gly Pro Ser
            340                 345                 350

Lys Gln Asp Leu Gln Ser Ala Tyr Glu Ala Ile Ser His
        355                 360                 365

<210> SEQ ID NO 13
<211> LENGTH: 438
<212> TYPE: DNA
<213> ORGANISM: Corynebacterium glutamicum
<220> FEATURE:
<221> NAME/KEY: CDS
<222> LOCATION: (1)..(435)

<400> SEQUENCE: 13 atg ctt gga aaa att ctc ctc ctc aac ggc cca aac ctg aac atg ctg      48
Met Leu Gly Lys Ile Leu Leu Leu Asn Gly Pro Asn Leu Asn Met Leu
1               5                   10                  15 ggc aaa cgc gag cct gac att tac gga cac gac acc ttg gaa gac gtc      96
Gly Lys Arg Glu Pro Asp Ile Tyr Gly His Asp Thr Leu Glu Asp Val
                20                  25                  30 gtc gcg ctg gca acc gct gag gct gcg aag cac ggc ctt gag gtt gag     144
Val Ala Leu Ala Thr Ala Glu Ala Ala Lys His Gly Leu Glu Val Glu
            35                  40                  45 gcg ctg cag agc aat cac gaa ggt gag cta atc gat gcg ctg cac aac     192
Ala Leu Gln Ser Asn His Glu Gly Glu Leu Ile Asp Ala Leu His Asn
        50                  55                  60 gct cgc ggc acc cac atc ggt tgc gtg att aac ccc ggc ggc ctg act     240
Ala Arg Gly Thr His Ile Gly Cys Val Ile Asn Pro Gly Gly Leu Thr
65                  70                  75                  80 cac act tcg gtg gcg ctt ttg gat gcg gtg aag gcg tct gag ctt cct     288
His Thr Ser Val Ala Leu Leu Asp Ala Val Lys Ala Ser Glu Leu Pro
                85                  90                  95 acc gtt gag gtg cac att tcc aat ccg cat gcc cgt gaa gag ttc cgc     336
Thr Val Glu Val His Ile Ser Asn Pro His Ala Arg Glu Glu Phe Arg
                100                 105                 110 cac cat tct tac att tcc ctc gcc gcg tcc gtt atc gct ggc gct         384
His His Ser Tyr Ile Ser Leu Ala Ala Val Ser Val Ile Ala Gly Ala
            115                 120                 125 ggc atc cag ggt tac cgt ttc gcg gtc gat atc ctg gca aat ctc aaa     432
Gly Ile Gln Gly Tyr Arg Phe Ala Val Asp Ile Leu Ala Asn Leu Lys
        130                 135                 140 aag tag                                                             438
Lys
145

<210> SEQ ID NO 14
<211> LENGTH: 145
<212> TYPE: PRT
<213> ORGANISM: Corynebacterium glutamicum

<400> SEQUENCE: 14

Met Leu Gly Lys Ile Leu Leu Leu Asn Gly Pro Asn Leu Asn Met Leu
1               5                   10                  15

Gly Lys Arg Glu Pro Asp Ile Tyr Gly His Asp Thr Leu Glu Asp Val
                20                  25                  30

Val Ala Leu Ala Thr Ala Glu Ala Ala Lys His Gly Leu Glu Val Glu
            35                  40                  45

Ala Leu Gln Ser Asn His Glu Gly Glu Leu Ile Asp Ala Leu His Asn
```

```
                    50                  55                  60
Ala Arg Gly Thr His Ile Gly Cys Val Ile Asn Pro Gly Gly Leu Thr
 65                  70                  75                  80

His Thr Ser Val Ala Leu Leu Asp Ala Val Lys Ala Ser Glu Leu Pro
                 85                  90                  95

Thr Val Glu Val His Ile Ser Asn Pro His Ala Arg Glu Glu Phe Arg
            100                 105                 110

His His Ser Tyr Ile Ser Leu Ala Ala Val Ser Val Ile Ala Gly Ala
        115                 120                 125

Gly Ile Gln Gly Tyr Arg Phe Ala Val Asp Ile Leu Ala Asn Leu Lys
    130                 135                 140

Lys
145

<210> SEQ ID NO 15
<211> LENGTH: 1857
<212> TYPE: DNA
<213> ORGANISM: Corynebacterium glutamicum
<220> FEATURE:
<221> NAME/KEY: CDS
<222> LOCATION: (1)..(1854)

<400> SEQUENCE: 15 atg cgt aca tcc att gcc act gtt tgt ttg tcc gga act ctt gct gaa    48
Met Arg Thr Ser Ile Ala Thr Val Cys Leu Ser Gly Thr Leu Ala Glu
 1               5                  10                  15 aag ctg cgc gca gct gca gat gct gga ttt gat ggt gtg gaa atc ttc    96
Lys Leu Arg Ala Ala Ala Asp Ala Gly Phe Asp Gly Val Glu Ile Phe
            20                  25                  30 gag cag gac ttg gtg gtt tcc ccg cat tcg gca gag cag att cgt cag   144
Glu Gln Asp Leu Val Val Ser Pro His Ser Ala Glu Gln Ile Arg Gln
        35                  40                  45 cgg gct cag gat ttg gga tta acc ctg gat ctg ttc cag ccg ttt cga   192
Arg Ala Gln Asp Leu Gly Leu Thr Leu Asp Leu Phe Gln Pro Phe Arg
    50                  55                  60 gat ttc gaa ggt gtg gaa gaa gag cag ttt ctg aag aat ctg cac cgc   240
Asp Phe Glu Gly Val Glu Glu Glu Gln Phe Leu Lys Asn Leu His Arg
 65                  70                  75                  80 ttg gaa gag aag ttc aag ctg atg aac agg ctt ggc att gag atg atc   288
Leu Glu Glu Lys Phe Lys Leu Met Asn Arg Leu Gly Ile Glu Met Ile
                 85                  90                  95 ttg ttg tgt tcc aat gtg ggc acc gcg acc atc aat gat gat gac ctt   336
Leu Leu Cys Ser Asn Val Gly Thr Ala Thr Ile Asn Asp Asp Asp Leu
            100                 105                 110 ttc gtg gag cag ttg cat cgt gca gca gat ttg gct gag aag tac aac   384
Phe Val Glu Gln Leu His Arg Ala Ala Asp Leu Ala Glu Lys Tyr Asn
        115                 120                 125 gtc aag att gct tat gaa gcg ttg gcg tgg ggc aag ttt gtc aat gat   432
Val Lys Ile Ala Tyr Glu Ala Leu Ala Trp Gly Lys Phe Val Asn Asp
    130                 135                 140 ttt gag cat gcg cat gca ctt gtg gag aag gtg aat cac aag gcg ctg   480
Phe Glu His Ala His Ala Leu Val Glu Lys Val Asn His Lys Ala Leu
145                 150                 155                 160 gga acc tgc ttg gat acg ttc cat att ctt tcc cgt ggt tgg gaa acc   528
Gly Thr Cys Leu Asp Thr Phe His Ile Leu Ser Arg Gly Trp Glu Thr
                165                 170                 175 gac gag gtg gaa aac atc ccg gcg gag aag atc ttc ttt gtt cag ttg   576
Asp Glu Val Glu Asn Ile Pro Ala Glu Lys Ile Phe Phe Val Gln Leu
            180                 185                 190
```

```
gcg gat gca ccg aag ctg agc atg gac att ttg tcc tgg tcg cgt cac        624
Ala Asp Ala Pro Lys Leu Ser Met Asp Ile Leu Ser Trp Ser Arg His
        195                 200                 205 cac cgt gtt ttc cct ggt gaa ggc gat ttc gat ctg gtg aaa ttc atg        672
His Arg Val Phe Pro Gly Glu Gly Asp Phe Asp Leu Val Lys Phe Met
210                 215                 220 gtt cat ctg gcc aag acg ggt tat gat ggc ccg att tct ttg gag atc        720
Val His Leu Ala Lys Thr Gly Tyr Asp Gly Pro Ile Ser Leu Glu Ile
225                 230                 235                 240 ttc aac gat tcc ttc cgc aag gcc gag gtt ggt cgc acc gcg att gat        768
Phe Asn Asp Ser Phe Arg Lys Ala Glu Val Gly Arg Thr Ala Ile Asp
                245                 250                 255 ggg ttg cgt tct ttg cgt tgg ttg gaa gat cag acc tgg cat gcg cta        816
Gly Leu Arg Ser Leu Arg Trp Leu Glu Asp Gln Thr Trp His Ala Leu
            260                 265                 270 aat gct gag gat cgt cca agc gca cta gag ctg cgt gca ctt cct gag        864
Asn Ala Glu Asp Arg Pro Ser Ala Leu Glu Leu Arg Ala Leu Pro Glu
        275                 280                 285 gtc gcg gaa cct gaa ggc gtt gat ttc att gag atc gcc act gga cgt        912
Val Ala Glu Pro Glu Gly Val Asp Phe Ile Glu Ile Ala Thr Gly Arg
290                 295                 300 ttg ggt gag acc att cgg gtt ctt cat caa ttg ggt ttc cgc ttg ggt        960
Leu Gly Glu Thr Ile Arg Val Leu His Gln Leu Gly Phe Arg Leu Gly
305                 310                 315                 320 ggt cat cac tgc agt aag cag gat tac cag gta tgg acc cag ggc gat       1008
Gly His His Cys Ser Lys Gln Asp Tyr Gln Val Trp Thr Gln Gly Asp
                325                 330                 335 gtg cgc att gtg gtg tgt gat cgt ggg gcc acc ggg gct cca acc acg       1056
Val Arg Ile Val Val Cys Asp Arg Gly Ala Thr Gly Ala Pro Thr Thr
            340                 345                 350 atc tct gcg atg ggc ttt gac acc cct gat cca gaa gcc gcg cat gcc       1104
Ile Ser Ala Met Gly Phe Asp Thr Pro Asp Pro Glu Ala Ala His Ala
        355                 360                 365 cgt gcg gaa ttg ctg cgg gct cag aca att gat cgt ccc cac atc gag       1152
Arg Ala Glu Leu Leu Arg Ala Gln Thr Ile Asp Arg Pro His Ile Glu
370                 375                 380 ggt gaa gtt gac ctt aaa ggt gtg tac gcg ccg gat ggg gtg gag ctg       1200
Gly Glu Val Asp Leu Lys Gly Val Tyr Ala Pro Asp Gly Val Glu Leu
385                 390                 395                 400 ttt ttc gcg ggg ccg agc ccc gat gga atg ccc gag tgg ctg ccg gaa       1248
Phe Phe Ala Gly Pro Ser Pro Asp Gly Met Pro Glu Trp Leu Pro Glu
                405                 410                 415 ttc ggc gtc gaa aag caa gaa gct ggt ctc att gaa gcc atc gac cac       1296
Phe Gly Val Glu Lys Gln Glu Ala Gly Leu Ile Glu Ala Ile Asp His
            420                 425                 430 gtc aat ttc gcc cag cca tgg caa cat ttt gat gag gca gtg ctg ttt       1344
Val Asn Phe Ala Gln Pro Trp Gln His Phe Asp Glu Ala Val Leu Phe
        435                 440                 445 tac acc gcg ctg atg gcg tta gag act gtg cgt gag gat gag ttc ccg       1392
Tyr Thr Ala Leu Met Ala Leu Glu Thr Val Arg Glu Asp Glu Phe Pro
450                 455                 460 agc cca att ggt ttg gtg cgc aat cag gtg atg cgt tcg ccg aat gat       1440
Ser Pro Ile Gly Leu Val Arg Asn Gln Val Met Arg Ser Pro Asn Asp
465                 470                 475                 480 gcg gtg cgg ttg ctg ctc agc gtg gcg ccg gag gac ggt gag cag gga       1488
Ala Val Arg Leu Leu Leu Ser Val Ala Pro Glu Asp Gly Glu Gln Gly
                485                 490                 495 gat ttc ctc aac gcg gcc tac ccg gag cac att gcg ttg gcc acg gcg       1536
Asp Phe Leu Asn Ala Ala Tyr Pro Glu His Ile Ala Leu Ala Thr Ala
            500                 505                 510
```

```
gac atc gtg gcg gtg gct gaa cgt gcg cgc aaa cga ggc ctg gat ttc       1584
Asp Ile Val Ala Val Ala Glu Arg Ala Arg Lys Arg Gly Leu Asp Phe
            515                 520                 525 ttg ccc gtc cca gag aat tac tac gac gat gtg cag gcg cgt ttt gat       1632
Leu Pro Val Pro Glu Asn Tyr Tyr Asp Asp Val Gln Ala Arg Phe Asp
530                 535                 540 ttg ccg cag gaa ttc ttg gac aca ctc aag gaa aac cac ctg ctt tac       1680
Leu Pro Gln Glu Phe Leu Asp Thr Leu Lys Glu Asn His Leu Leu Tyr
545                 550                 555                 560 gac tgc gac gag aac ggc gaa ttc ctc cac ttt tac acc cgc acg ttg       1728
Asp Cys Asp Glu Asn Gly Glu Phe Leu His Phe Tyr Thr Arg Thr Leu
            565                 570                 575 ggc acg ctg ttc ttc gaa gtg gtg gaa cgc cgc ggt ggt ttt gca ggt       1776
Gly Thr Leu Phe Phe Glu Val Val Glu Arg Arg Gly Gly Phe Ala Gly
            580                 585                 590 tgg ggc gaa aca aac gct ccg gtg cgg tta gcg gcg cag tat cgt gag       1824
Trp Gly Glu Thr Asn Ala Pro Val Arg Leu Ala Ala Gln Tyr Arg Glu
            595                 600                 605 gtg cgg gac ctc gag cgg gga atc ccc aac tag                           1857
Val Arg Asp Leu Glu Arg Gly Ile Pro Asn
610                 615

<210> SEQ ID NO 16
<211> LENGTH: 618
<212> TYPE: PRT
<213> ORGANISM: Corynebacterium glutamicum

<400> SEQUENCE: 16

Met Arg Thr Ser Ile Ala Thr Val Cys Leu Ser Gly Thr Leu Ala Glu
1               5                   10                  15

Lys Leu Arg Ala Ala Ala Asp Ala Gly Phe Asp Gly Val Glu Ile Phe
            20                  25                  30

Glu Gln Asp Leu Val Val Ser Pro His Ser Ala Glu Gln Ile Arg Gln
        35                  40                  45

Arg Ala Gln Asp Leu Gly Leu Thr Leu Asp Leu Phe Gln Pro Phe Arg
    50                  55                  60

Asp Phe Glu Gly Val Glu Glu Gln Phe Leu Lys Asn Leu His Arg
65                  70                  75                  80

Leu Glu Glu Lys Phe Lys Leu Met Asn Arg Leu Gly Ile Glu Met Ile
                85                  90                  95

Leu Leu Cys Ser Asn Val Gly Thr Ala Thr Ile Asn Asp Asp Asp Leu
            100                 105                 110

Phe Val Glu Gln Leu His Arg Ala Ala Asp Leu Ala Glu Lys Tyr Asn
        115                 120                 125

Val Lys Ile Ala Tyr Glu Ala Leu Ala Trp Gly Lys Phe Val Asn Asp
    130                 135                 140

Phe Glu His Ala His Ala Leu Val Glu Lys Val Asn His Lys Ala Leu
145                 150                 155                 160

Gly Thr Cys Leu Asp Thr Phe His Ile Leu Ser Arg Gly Trp Glu Thr
                165                 170                 175

Asp Glu Val Glu Asn Ile Pro Ala Glu Lys Ile Phe Phe Val Gln Leu
            180                 185                 190

Ala Asp Ala Pro Lys Leu Ser Met Asp Ile Leu Ser Trp Ser Arg His
        195                 200                 205

His Arg Val Phe Pro Gly Glu Gly Asp Phe Asp Leu Val Lys Phe Met
    210                 215                 220
```

Val His Leu Ala Lys Thr Gly Tyr Asp Gly Pro Ile Ser Leu Glu Ile
225                 230                 235                 240

Phe Asn Asp Ser Phe Arg Lys Ala Glu Val Gly Arg Thr Ala Ile Asp
            245                 250                 255

Gly Leu Arg Ser Leu Arg Trp Leu Glu Asp Gln Thr Trp His Ala Leu
        260                 265                 270

Asn Ala Glu Asp Arg Pro Ser Ala Leu Glu Leu Arg Ala Leu Pro Glu
    275                 280                 285

Val Ala Glu Pro Glu Gly Val Asp Phe Ile Glu Ile Ala Thr Gly Arg
290                 295                 300

Leu Gly Glu Thr Ile Arg Val Leu His Gln Leu Gly Phe Arg Leu Gly
305                 310                 315                 320

Gly His His Cys Ser Lys Gln Asp Tyr Gln Val Trp Thr Gln Gly Asp
                325                 330                 335

Val Arg Ile Val Val Cys Asp Arg Gly Ala Thr Gly Ala Pro Thr Thr
                340                 345                 350

Ile Ser Ala Met Gly Phe Asp Thr Pro Asp Pro Glu Ala Ala His Ala
                355                 360                 365

Arg Ala Glu Leu Leu Arg Ala Gln Thr Ile Asp Arg Pro His Ile Glu
370                 375                 380

Gly Glu Val Asp Leu Lys Gly Val Tyr Ala Pro Asp Gly Val Glu Leu
385                 390                 395                 400

Phe Phe Ala Gly Pro Ser Pro Asp Gly Met Pro Glu Trp Leu Pro Glu
                405                 410                 415

Phe Gly Val Glu Lys Gln Glu Ala Gly Leu Ile Glu Ala Ile Asp His
                420                 425                 430

Val Asn Phe Ala Gln Pro Trp Gln His Phe Asp Glu Ala Val Leu Phe
        435                 440                 445

Tyr Thr Ala Leu Met Ala Leu Glu Thr Val Arg Glu Asp Glu Phe Pro
        450                 455                 460

Ser Pro Ile Gly Leu Val Arg Asn Gln Val Met Arg Ser Pro Asn Asp
465                 470                 475                 480

Ala Val Arg Leu Leu Leu Ser Val Ala Pro Glu Asp Gly Glu Gln Gly
                485                 490                 495

Asp Phe Leu Asn Ala Ala Tyr Pro Glu His Ile Ala Leu Ala Thr Ala
            500                 505                 510

Asp Ile Val Ala Val Ala Glu Arg Ala Lys Arg Gly Leu Asp Phe
        515                 520                 525

Leu Pro Val Pro Glu Asn Tyr Tyr Asp Val Gln Ala Arg Phe Asp
    530                 535                 540

Leu Pro Gln Glu Phe Leu Asp Thr Leu Lys Glu Asn His Leu Leu Tyr
545                 550                 555                 560

Asp Cys Asp Glu Asn Gly Glu Phe Leu His Phe Tyr Thr Arg Thr Leu
                565                 570                 575

Gly Thr Leu Phe Phe Glu Val Val Glu Arg Gly Gly Phe Ala Gly
            580                 585                 590

Trp Gly Glu Thr Asn Ala Pro Val Arg Leu Ala Ala Gln Tyr Arg Glu
        595                 600                 605

Val Arg Asp Leu Glu Arg Gly Ile Pro Asn
610                 615

<210> SEQ ID NO 17
<211> LENGTH: 852
<212> TYPE: DNA

<213> ORGANISM: Corynebacterium glutamicum
<220> FEATURE:
<221> NAME/KEY: CDS
<222> LOCATION: (1)..(849)

<400> SEQUENCE: 17

```
atg aac gac agt att ctc ctc ggc cta atc ggc cag ggc ctc gac cta      48
Met Asn Asp Ser Ile Leu Leu Gly Leu Ile Gly Gln Gly Leu Asp Leu
1               5                   10                  15 tcg cgc acc ccc gca atg cac gag gcg gaa ggc ctc gcg cag gga cgt      96
Ser Arg Thr Pro Ala Met His Glu Ala Glu Gly Leu Ala Gln Gly Arg
                20                  25                  30 gcg acc gtg tac agg cgc atc gac acg ctt ggg tcg cgt gct tcc ggg     144
Ala Thr Val Tyr Arg Arg Ile Asp Thr Leu Gly Ser Arg Ala Ser Gly
            35                  40                  45 caa gat tta aag acg ctt ctc gac gcc gcc ctc tac ctt ggc ttc aac     192
Gln Asp Leu Lys Thr Leu Leu Asp Ala Ala Leu Tyr Leu Gly Phe Asn
        50                  55                  60 ggc ctg aac atc act cac ccg tac aaa caa gca gta tta ccc ctg ctt     240
Gly Leu Asn Ile Thr His Pro Tyr Lys Gln Ala Val Leu Pro Leu Leu
65                  70                  75                  80 gac gaa gtc tcc gaa caa gcc acc caa ctc ggc gca gtg aat act gtc     288
Asp Glu Val Ser Glu Gln Ala Thr Gln Leu Gly Ala Val Asn Thr Val
                85                  90                  95 gtt atc gac gcc aac ggc cac acc acc ggc cac aac acc gac gtc tcc     336
Val Ile Asp Ala Asn Gly His Thr Thr Gly His Asn Thr Asp Val Ser
                100                 105                 110 gga ttt ggc cgc gga atg gaa gaa ggc ctc ccc aac gcc aag ctc gat     384
Gly Phe Gly Arg Gly Met Glu Glu Gly Leu Pro Asn Ala Lys Leu Asp
            115                 120                 125 tcc gtc gtg cag gtc ggc gcc ggc ggt gta gga aac gca gtg gca tac     432
Ser Val Val Gln Val Gly Ala Gly Gly Val Gly Asn Ala Val Ala Tyr
        130                 135                 140 gcc ctg gtc acc cat ggt gtg cag aaa ctt cag gtc gct gac ctc gac     480
Ala Leu Val Thr His Gly Val Gln Lys Leu Gln Val Ala Asp Leu Asp
145                 150                 155                 160 act tcc cgc gca cag gca tta gcg gat gtc atc aac aat gca gtc ggc     528
Thr Ser Arg Ala Gln Ala Leu Ala Asp Val Ile Asn Asn Ala Val Gly
                165                 170                 175 cgc gaa gct gtc gtg gga gta gac gcc cgc ggc atc gaa gac gtc atc     576
Arg Glu Ala Val Val Gly Val Asp Ala Arg Gly Ile Glu Asp Val Ile
                180                 185                 190 gca gcc gcc gac gga gta gtc aac gca acc ccc atg gga atg ccc gca     624
Ala Ala Ala Asp Gly Val Val Asn Ala Thr Pro Met Gly Met Pro Ala
            195                 200                 205 cac ccc ggc acc gcc ttt gat gtc agc tgc ctc acc aag gat cac tgg     672
His Pro Gly Thr Ala Phe Asp Val Ser Cys Leu Thr Lys Asp His Trp
        210                 215                 220 gtt ggc gac gtc gtg tac atg ccc atc gaa act gaa ctt ctc aag gcc     720
Val Gly Asp Val Val Tyr Met Pro Ile Glu Thr Glu Leu Leu Lys Ala
225                 230                 235                 240 gcc cgt gcc ctc ggc tgc gaa acc ctc gac gga acc cgc atg gca atc     768
Ala Arg Ala Leu Gly Cys Glu Thr Leu Asp Gly Thr Arg Met Ala Ile
                245                 250                 255 cac caa gcc gtc gat gcc ttc cgc ctg ttc acc ggc ctc gaa ccc gac     816
His Gln Ala Val Asp Ala Phe Arg Leu Phe Thr Gly Leu Glu Pro Asp
                260                 265                 270 gtc tcc cgc atg cgg gaa act ttc cta tcc ctc taa                     852
Val Ser Arg Met Arg Glu Thr Phe Leu Ser Leu
        275                 280
```

<210> SEQ ID NO 18
<211> LENGTH: 283
<212> TYPE: PRT
<213> ORGANISM: Corynebacterium glutamicum

<400> SEQUENCE: 18

```
Met Asn Asp Ser Ile Leu Leu Gly Leu Ile Gly Gln Gly Leu Asp Leu
1               5                   10                  15

Ser Arg Thr Pro Ala Met His Glu Ala Glu Gly Leu Ala Gln Gly Arg
            20                  25                  30

Ala Thr Val Tyr Arg Arg Ile Asp Thr Leu Gly Ser Arg Ala Ser Gly
        35                  40                  45

Gln Asp Leu Lys Thr Leu Leu Asp Ala Ala Leu Tyr Leu Gly Phe Asn
    50                  55                  60

Gly Leu Asn Ile Thr His Pro Tyr Lys Gln Ala Val Leu Pro Leu Leu
65                  70                  75                  80

Asp Glu Val Ser Glu Gln Ala Thr Gln Leu Gly Ala Val Asn Thr Val
                85                  90                  95

Val Ile Asp Ala Asn Gly His Thr Thr Gly His Asn Thr Asp Val Ser
            100                 105                 110

Gly Phe Gly Arg Gly Met Glu Glu Gly Leu Pro Asn Ala Lys Leu Asp
        115                 120                 125

Ser Val Val Gln Val Gly Ala Gly Gly Val Gly Asn Ala Val Ala Tyr
    130                 135                 140

Ala Leu Val Thr His Gly Val Gln Lys Leu Gln Val Ala Asp Leu Asp
145                 150                 155                 160

Thr Ser Arg Ala Gln Ala Leu Ala Asp Val Ile Asn Asn Ala Val Gly
                165                 170                 175

Arg Glu Ala Val Val Gly Val Asp Ala Arg Gly Ile Glu Asp Val Ile
            180                 185                 190

Ala Ala Ala Asp Gly Val Val Asn Ala Thr Pro Met Gly Met Pro Ala
        195                 200                 205

His Pro Gly Thr Ala Phe Asp Val Ser Cys Leu Thr Lys Asp His Trp
    210                 215                 220

Val Gly Asp Val Val Tyr Met Pro Ile Glu Thr Glu Leu Leu Lys Ala
225                 230                 235                 240

Ala Arg Ala Leu Gly Cys Glu Thr Leu Asp Gly Thr Arg Met Ala Ile
                245                 250                 255

His Gln Ala Val Asp Ala Phe Arg Leu Phe Thr Gly Leu Glu Pro Asp
            260                 265                 270

Val Ser Arg Met Arg Glu Thr Phe Leu Ser Leu
        275                 280
```

<210> SEQ ID NO 19
<211> LENGTH: 24
<212> TYPE: DNA
<213> ORGANISM: Artificial sequence
<220> FEATURE:
<223> OTHER INFORMATION: Synthetic primer

<400> SEQUENCE: 19
acgaagtgac tgctatcacc cttg                                      24

<210> SEQ ID NO 20
<211> LENGTH: 23
<212> TYPE: DNA
<213> ORGANISM: Artificial sequence

```
<220> FEATURE:
<223> OTHER INFORMATION: Synthetic primer

<400> SEQUENCE: 20
cagaacttta ctgcatccgc aca                                              23

<210> SEQ ID NO 21
<211> LENGTH: 36
<212> TYPE: DNA
<213> ORGANISM: Artificial sequence
<220> FEATURE:
<223> OTHER INFORMATION: Synthetic primer

<400> SEQUENCE: 21
gtggatgaga caggactatc tagagctaca gtgaca                                36

<210> SEQ ID NO 22
<211> LENGTH: 33
<212> TYPE: DNA
<213> ORGANISM: Artificial sequence
<220> FEATURE:
<223> OTHER INFORMATION: Synthetic primer

<400> SEQUENCE: 22
agaattgatc ttaggtcact aaaactaatt cag                                   33

<210> SEQ ID NO 23
<211> LENGTH: 25
<212> TYPE: DNA
<213> ORGANISM: Artificial sequence
<220> FEATURE:
<223> OTHER INFORMATION: Synthetic primer

<400> SEQUENCE: 23
gtaggtatca cccatgcaca agttg                                            25

<210> SEQ ID NO 24
<211> LENGTH: 23
<212> TYPE: DNA
<213> ORGANISM: Artificial sequence
<220> FEATURE:
<223> OTHER INFORMATION: Synthetic primer

<400> SEQUENCE: 24
cctagtatcg taaccccga ttc                                               23

<210> SEQ ID NO 25
<211> LENGTH: 21
<212> TYPE: DNA
<213> ORGANISM: Artificial sequence
<220> FEATURE:
<223> OTHER INFORMATION: Synthetic primer

<400> SEQUENCE: 25
gttttcccag tcacgacgtt g                                                21

<210> SEQ ID NO 26
<211> LENGTH: 24
<212> TYPE: DNA
<213> ORGANISM: Artificial sequence
<220> FEATURE:
<223> OTHER INFORMATION: Synthetic primer

<400> SEQUENCE: 26
actggcattg atgtcgatcc agca                                             24
```

```
<210> SEQ ID NO 27
<211> LENGTH: 23
<212> TYPE: DNA
<213> ORGANISM: Artificial sequence
<220> FEATURE:
<223> OTHER INFORMATION: Synthetic primer

<400> SEQUENCE: 27
ctgttgccaa tttgcgaagc tca                                          23
```

METHOD FOR PRODUCING POLYMER, METHOD FOR PRODUCING ORGANIC ACID, AND ORGANIC ACID-PRODUCING MICROORGANISM

CROSS-REFERENCE TO RELATED APPLICATION

This is a continuation of International Application PCT/JP2012/056935, filed on Mar. 16, 2012, and designated the U.S., (and claims priority from Japanese Patent Application 2011-061412 which was filed on Mar. 18, 2011), the entire contents of which are incorporated herein by reference.

TECHNICAL FIELD

The present invention relates to a method of producing a high-quality polymer with less coloration, a method of producing an organic acid for obtaining the polymer, an organic acid-producing microorganism used to produce the organic acid.

BACKGROUND ART

Biodegradable plastic materials, which are eventually decomposed into water and carbon dioxide by microorganisms, are used in a wide variety of applications such as food containers and agricultural materials.

At present, such polyesters are produced by polycondensation of a material derived from a fossil fuel resource; however, in view of recent environmental problems at a global scale such as concerns for depletion of fossil fuel resources and increase in the atmospheric carbon dioxide level, attention has been drawn upon a method of deriving a starting materials of these polymers from a biomass resource.

So far, there have been disclosed technologies for producing a dicarboxylic acid used as a starting material of a polyester, such as succinic acid or adipic acid, from glucose, sucrose or the like of a biomass resource origin by a fermentation method (see Patent Documents 1 and 2 and Non-patent Document 1).

In cases where a dicarboxylic acid is used as a starting material of a polymer, in order to maintain the polymerization activity and to thereby obtain a high-quality polymer with less coloration, a highly pure dicarboxylic acid is required. As a method of purifying a dicarboxylic acid produced by a fermentation method, there are disclosed, for example, a method in which an ion-exchange resin is used and a method in which electrodialysis is used (Patent Documents 3 and 4). Examples of a substance which causes coloration of a polymer include those impurities that exhibit absorption in the ultraviolet region of 250 to 300 nm, and it is described to be useful that such impurities be reduced to not higher than a specific amount (Patent Document 5).

PRIOR ART DOCUMENTS

Patent Documents

Patent Document 1: JP 11-113588A

Patent Document 2: JP 11-196888A

Patent Document 3: U.S. Pat. No. 6,284,904

Patent Document 4: JP 2-283289A

Patent Document 5: JP 2010-100617A

Non-Patent Documents

Non-patent Document 1: Journal of the American Chemical Society No. 116 (1994), 399-400

SUMMARY OF THE INVENTION

However, in these production methods described in Patent Documents 1 and 2 and Non-patent Document 1, the resulting acid compound may contain a variety of impurities such as organic acids other than the desired dicarboxylic acid that were produced as by-products, sugars that were left without being completely assimilated by a microorganism, compounds containing elemental nitrogen originated from a biomass resource and metal cations; therefore, a further improvement is necessary.

Furthermore, also in the dicarboxylic acids obtained by the purification processes according to Patent Documents 3 and 4, when the dicarboxylic acids are used as a starting material of a polymer, for example, coloration tends to occur in the resulting polymer; therefore, a further improvement is necessary.

Moreover, in Patent Document 5, the impurities causing coloration of a polymer were not identified and, from the practical standpoint, it is an important problem to attain removal of such impurities from a dicarboxylic acid by a more efficient and inexpensive method.

In view of the above, objects of the present invention are: to provide a method of producing a high-quality polymer with less coloration; to provide a method of producing an organic acid suitable for this purpose; and to provide a microorganism used to produce the organic acid.

In order to solve the above-described problems, the present inventors intensively studied and discovered that, among a variety of impurities that may be contained in an organic acid used as a starting material of a polymer, aromatic carboxylic acids such as protocatechuic acid are the substances that cause coloration of a polymer; and that aromatic carboxylic acids such as protocatechuic acid are not easily separated by purification. Furthermore, the present inventors produced an organic acid by allowing a microorganism modified so that the production of aromatic carboxylic acid such as protocatechuic acid is reduced, or a treated cell thereof, to act on an organic raw material and discovered that, by using such an organic acid to synthesize a polymer, coloration in the resulting polymer can be reduced, there by completed the present invention.

That is, according to the present invention, the following inventions are provided.

[1] A method of producing a polymer, which comprises the step of performing a polymerization reaction using, as a starting material, an organic acid obtained by allowing a microorganism or a treated cell of thereof to act on an organic raw material, wherein said microorganism has an ability to produce the organic acid and has been modified so as to produce less aromatic carboxylic acid as compared to an unmodified strain.

[2] The method according to [1], wherein said microorganism has been modified so that at least one enzyme activity selected from the group consisting of DAHP synthase activity, dehydroquinate synthase activity, dehydroquinate dehydratase activity and dehydroshikimate dehydratase activity is reduced as compared to an unmodified strain, and production of an aromatic carboxylic acid is thereby reduced.

[3] The method according to [1] or [2], wherein said organic acid is subjected to a crystallization treatment.
[4] The method according to any one of [1] to [3], wherein said aromatic carboxylic acid is a hydroxybenzene carboxylic acid.
[5] The method according to any one of [1] to [4], wherein said organic acid is succinic acid.
[6] The method according to [5], wherein said polymer is a polyester or a polyamide.
[7] A method of producing an organic acid, comprising the step of allowing a microorganism or a treated cell thereof to act on an organic raw material, wherein said microorganism has an ability to produce the organic acid and has been modified so as to produce less aromatic carboxylic acid as compared to an unmodified strain.
[8] The method according to [7], wherein said microorganism has been modified so that at least one enzyme activity selected from the group consisting of DAHP synthase activity, dehydroquinate synthase activity, dehydroquinate dehydratase activity and dehydroshikimate dehydratase activity is reduced as compared to an unmodified strain, and production of an aromatic carboxylic acid is thereby reduced.
[9] The method according to [7] or [8], wherein said microorganism or a treated cell thereof is allowed to act on said organic raw material in an anaerobic atmosphere.
[10] The method according to any one of [7] to [9], wherein said organic acid is succinic acid.
[11] The method according to any one of [7] to [10], further comprising the step of performing a crystallization treatment of said organic acid.
[12] The method according to any one of [7] to [11], wherein said aromatic carboxylic acid is a hydroxybenzene carboxylic acid.
[13] The method according to any one of [7] to [12], wherein said microorganism is at least one bacterium selected from the group consisting of coryneform bacteria, bacteria belonging to the genus *Mycobacterium*, bacteria belonging to the genus *Rhodococcus*, bacteria belonging to the genus *Nocardia* and bacteria belonging to the genus *Streptomyces*.
[14] A coryneform bacterium, which has an ability to produce an organic acid and has been modified so that at least one enzyme activity selected from the group consisting of dehydroquinate synthase activity, dehydroquinate dehydratase activity and dehydroshikimate dehydratase activity is reduced as compared to an unmodified strain, and the production of an aromatic carboxylic acid is thereby reduced.
[15] The coryneform bacterium according to [14], which has been modified so that the dehydroshikimate dehydratase activity is reduced.
[16] The coryneform bacterium according to [15], wherein said dehydroshikimate dehydratase activity is reduced by disrupting a gene encoding dehydroshikimate dehydratase or by introducing a mutation into said gene.
[17] The coryneform bacterium according to [16], wherein said gene encoding dehydroshikimate dehydratase is a DNA comprising the nucleotide sequence shown in SEQ ID NO:15 or a DNA which hybridizes with a complementary sequence of said nucleotide sequence shown in SEQ ID NO:15 under stringent conditions and encodes a protein having dehydroshikimate dehydratase activity.
[18] The coryneform bacterium according to any one of [14] to [17], wherein said aromatic carboxylic acid is a hydroxybenzene carboxylic acid.
[19] The coryneform bacterium according to [18], wherein said aromatic carboxylic acid is protocatechuic acid.

By the present invention, production of aromatic carboxylic acids which cause coloration of a polymer can be reduced, so that, by using the organic acid of the present invention as a starting material of a polymer, a high-quality polymer with less coloration can be obtained. By the present invention, the purification step of an organic acid can be simplified and the production cost can thus be reduced. Furthermore, the present invention can greatly contribute to solving the environmental problems and problems of depletion in fossil fuel resources and the like.

BRIEF DESCRIPTION OF THE DRAWINGS

FIG. 4 is a drawing of a crystallization apparatus.

EMBODIMENTS FOR CARRYING OUT THE INVENTION

Figure 1:
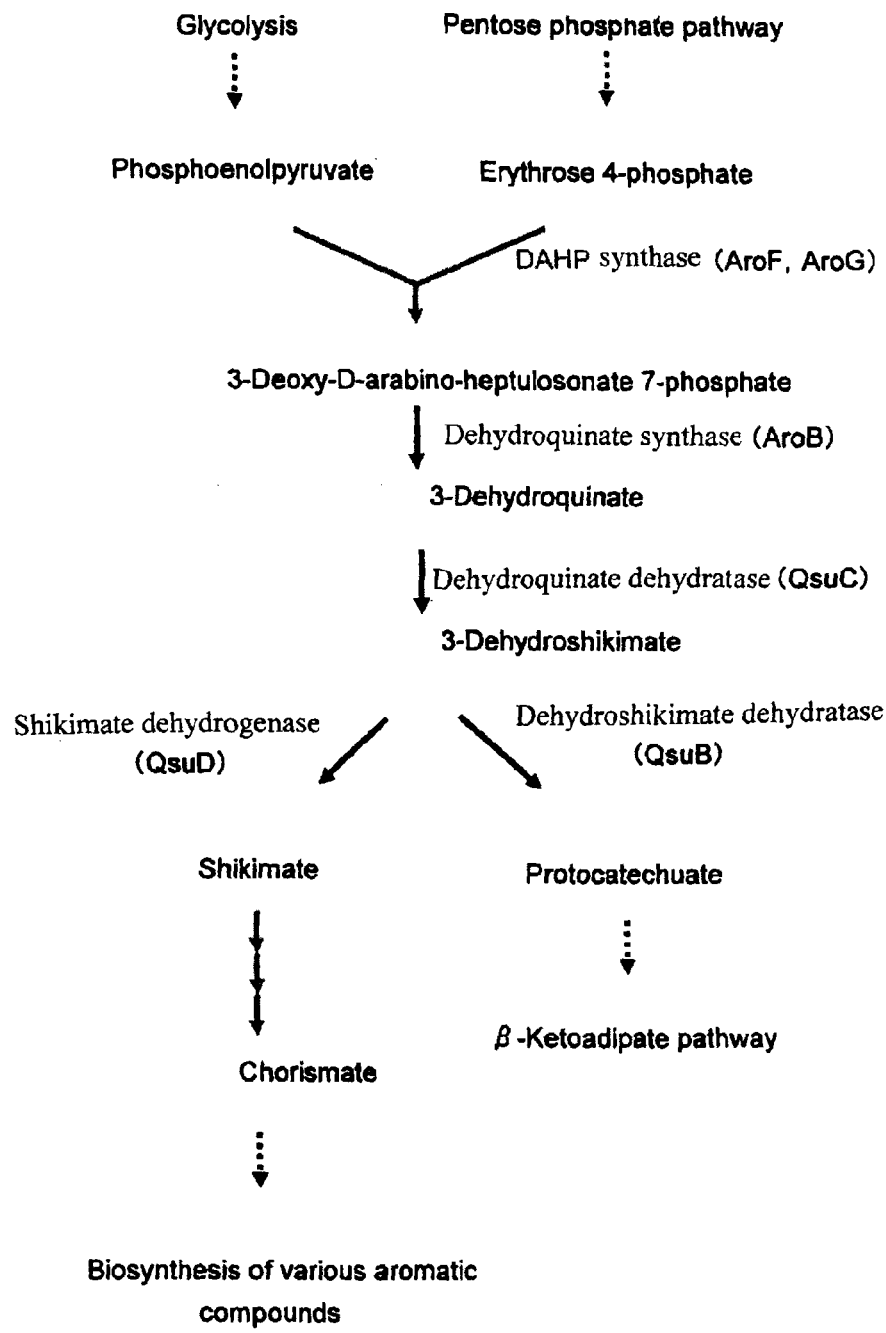
FIG. 1 is a diagram showing the synthetic pathway of protocatechuic acid.

The embodiments of the present invention will now be described in detail.
<Microorganism of the Present Invention>
The microorganism according to the present invention has an ability to produce an organic acid and has been modified so as to produce less aromatic carboxylic acid as compared to an unmodified strain. The expression "modified so as to produce less aromatic carboxylic acid as compared to an unmodified strain" encompasses a condition in which the activity of an enzyme relating to a biosynthetic pathway of an aromatic carboxylic acid is directly and indirectly reduced as compared to an unmodified strain; a condition in which, because of an increase in the activity of an enzyme of other biosynthetic pathway which shares a precursor with an aromatic carboxylic acid but branches from the biosynthetic pathway thereof, the flow of the precursor of the aromatic carboxylic acid to its biosynthetic pathway is reduced, so that the biosynthesis of the aromatic carboxylic acid is indirectly reduced; and a condition in which the activity of an enzyme relating to a decomposition pathway of an aromatic carboxylic acid is directly and indirectly increased as compared to an unmodified strain.

Specific examples of such microorganism include those which have been modified so that at least one enzyme activity selected from the group consisting of DAHP synthase activity, dehydroquinate synthase activity, dehydroquinate dehydratase activity and dehydroshikimate dehydratase activity is reduced as compared to an unmodified strain. Thereamong, the microorganism of the present invention is preferably a microorganism which has been modified so that at least one enzyme activity selected from the group consisting of dehydroquinate synthase activity, dehydroquinate dehydratase activity and dehydroshikimate dehydratase activity is reduced as compared to an unmodified strain, more preferably a microorganism which has been modified so that dehydroquinate dehydratase activity and/or dehydroshikimate dehydratase activity is/are reduced as compared to an unmodified strain, particularly preferably a microorganism which has been modified so that dehydroshikimate dehydratase activity is reduced as compared to an unmodified strain.

The term "having an ability to produce an organic acid" used herein means that, when the microorganism is cultured in a medium, the microorganism can produce and accumulate an organic acid in the medium.

The organic acid is not particularly restricted as long as it is an organic acid which is not an aromatic carboxylic acid, and it is preferably an amino acid or a carboxylic acid, more preferably a carboxylic acid, still more preferably an aliphatic carboxylic acid. Further, among these carboxylic acids, the organic acid is preferably a polycarboxylic acid, more preferably a dicarboxylic acid.

Examples of the organic acid which is not an aromatic carboxylic acid include lactic acid, succinic acid, malic acid, fumaric acid, oxaloacetic acid, citric acid, isocitric acid, 2-oxoglutaric acid, cis-aconitic acid, pyruvic acid, acetic acid and amino acids. Thereamong, the organic acid which is not an aromatic carboxylic acid is preferably a dicarboxylic acid, more preferably succinic acid, malic acid, fumaric acid, citric acid, isocitric acid, 2-oxoglutaric acid, cis-aconitic acid or pyruvic acid, still more preferably succinic acid, malic acid or fumaric acid, particularly preferably succinic acid.

Further, the term "an ability to produce an aromatic carboxylic acid" used herein refers to an ability of the microorganism of the present invention to produce and accumulate an aromatic carboxylic acid in a medium when the microorganism is cultured in the medium. The expression "a reduced ability to produce an aromatic carboxylic acid" means that the ability to produce an aromatic carboxylic acid is reduced as compared to an unmodified strain such as a wild-type strain. Here, the term "unmodified strain" encompasses wild-type strains and those strains which have an ability to produce an aromatic carboxylic acid at a level comparable to a wild-type strain, as well as those strains having DAHP synthase activity, dehydroquinate synthase activity, dehydroquinate dehydratase activity and dehydroshikimate dehydratase activity.

Examples of an aromatic carboxylic acid to be reduced during culturing include oxygen-containing heterocyclic aromatic carboxylic acids, nitrogen-containing heterocyclic aromatic carboxylic acids and benzene-based aromatic carboxylic acids.

Examples of the oxygen-containing heterocyclic aromatic carboxylic acids include those in which a carboxyl group is bound, directly or via a linking group, to an oxygen-containing heterocyclic ring having aromatic properties, and specific examples thereof include furan monocarboxylic acids such as furoic acid and pyromucic acid; and furan dicarboxylic acids such dehydromucic acid.

Examples of the nitrogen-containing heterocyclic aromatic carboxylic acids include those in which a carboxyl group is bound, directly or via a linking group, to a nitrogen-containing heterocyclic ring having aromatic properties, and specific examples thereof include pyridine monocarboxylic acids such as nicotinic acid, picolinic acid and isonicotinic acid; and hydroxypyridine carboxylic acids such as citrazinic acid; pyridine dicarboxylic acids such as quinolinic acid, lutidinic acid, isocinchomeronic acid, dipicolinic acid, cinchomeronic acid, dinicotinic acid and uvitonic acid; and pyridine tricarboxylic acids such as berberonic acid.

Examples of the benzene-based aromatic carboxylic acids include those in which a carboxyl group is bound to a benzene ring directly or via a linking group, and the benzene ring has preferably a plurality of substituents, more preferably three or more substituents. Thereamong, hydroxybenzene carboxylic acids having a hydroxyl group in addition to a carboxyl group are preferred and hydroxybenzene carboxylic acids having a plurality of carboxyl groups are more preferred. Further, hydroxybenzene carboxylic acids which have a hydroxy group and a plurality of carboxyl groups at the same time are particularly preferred. These hydroxybenzene carboxylic acids also include derivatives thereof which have a substituent in addition to a hydroxy group and a carboxyl group.

More specific examples of the benzene-based aromatic carboxylic acids include benzene monocarboxylic acids such as benzoic acid, toluic acid, xylic acid, α-toluic acid, cinnamic acid and hydrocinnamic acid; benzene dicarboxylic acids such as phthalic acid, isophthalic acid and terephthalic acid; benzene tricarboxylic acids such as hemimellitic acid, trimellitic acid and trimesic acid; hydroxybenzene carboxylic acids such as salicylic acid and creosotic acid; dihydroxybenzene carboxylic acids such as pyrocatechuic acid, protocatechuic acid, resorcylic acid and gentisic acid; and trihydroxybenzene carboxylic acids such as gallic acid.

Thereamong, it is preferred that a furan dicarboxylic acid such as dehydromucic acid; a hydroxypyridine carboxylic acid such as citrazinic acid; a pyridine dicarboxylic acid such as quinolinic acid, lutidinic acid, isocinchomeronic acid, dipicolinic acid, cinchomeronic acid, dinicotinic acid or uvitonic acid; a pyridine tricarboxylic acid such as berberonic acid; a benzene dicarboxylic acid such as phthalic acid, isophthalic acid or terephthalic acid; a benzene tricarboxylic acid such as hemimellitic acid, trimellitic acid or trimesic acid; a hydroxybenzene carboxylic acid such as salicylic acid or creosotic acid; a dihydroxybenzene carboxylic acid such as pyrocatechuic acid, protocatechuic acid, resorcylic acid or gentisic acid; or a trihydroxybenzene carboxylic acid such as gallic acid be reduced.

It is more preferred that a hydroxypyridine carboxylic acid such as citrazinic acid; a pyridine dicarboxylic acid such as quinolinic acid, lutidinic acid, isocinchomeronic acid, dipicolinic acid, cinchomeronic acid, dinicotinic acid or uvitonic acid; a benzene dicarboxylic acid such as phthalic acid, isophthalic acid or terephthalic acid; a benzene tricarboxylic acid such as hemimellitic acid, trimellitic acid or trimesic acid; a hydroxybenzene carboxylic acid such as salicylic acid or creosotic acid; or a dihydroxybenzene carboxylic acid such as pyrocatechuic acid, protocatechuic acid, resorcylic acid or gentisic acid be reduced.

It is still more preferred that a pyridine dicarboxylic acid such as quinolinic acid, lutidinic acid, isocinchomeronic acid, dipicolinic acid, cinchomeronic acid, dinicotinic acid or uvitonic acid; a hydroxybenzene carboxylic acid such as salicylic acid or creosotic acid; or a dihydroxybenzene carboxylic acid such as pyrocatechuic acid, protocatechuic acid, resorcylic acid or gentisic acid be reduced.

It is especially preferred that lutidinic acid, uvitonic acid, pyrocatechuic acid, protocatechuic acid, resorcylic acid or gentisic acid be reduced.

It is yet still more preferred that pyrocatechuic acid, protocatechuic acid, resorcylic acid or gentisic acid be reduced, and it is particularly preferred that protocatechuic acid be reduced.

Although the details of the mechanism are not clear, causes of coloration are speculated to be that, during the later-described polymer polymerization reaction, these aromatic carboxylic acids are cross-linked between the resulting polymers, or colored substances, in which these aromatic carboxylic acids are configured on a catalyst used in the polymer synthesis, are generated. Therefore, it is preferred that such coloration-causing aromatic carboxylic acid be reduced in the production of an organic acid since it allows the later-described purification process to be simplified and consequently, the production cost of an organic acid can be reduced.

The concentration of an aromatic carboxylic acid in the later-described culture medium or the resulting organic acid can be determined by measuring and analyzing the organic acid by conventionally known column chromatography.

The microorganism according to the present invention may be a microorganism which is obtained by modifying a microorganism intrinsically having an ability to produce an organic acid, or a microorganism imparted with an ability to produce an organic acid by breeding, so that the activity of at least one enzyme selected from the group consisting of DAHP synthase, dehydroquinate synthase, dehydroquinate dehydratase and dehydroshikimate dehydratase is reduced and the ability to produce an aromatic carboxylic acid is thereby reduced. Alternatively, the microorganism according to the present invention may also be a microorganism which has been modified as in the above so that the ability to produce an aromatic carboxylic acid is reduced and then imparted with an ability to produce an organic acid.

Examples of a means for imparting an ability to produce an organic acid by breeding include mutation treatments and gene recombination treatments. For each organic acid, a known method, such as enhancement of the expression of the respective biosynthetic enzyme genes, can be employed. For instance, when imparting an ability to produce succinic acid, a means for reducing the lactate dehydrogenase activity by modification, a means for enhancing the pyruvate carboxylate activity or the like may be employed.

The microorganism to be used in the present invention can be obtained by using a microorganism shown below as a parent strain and modifying the parent strain. The type of the parent strain is not particularly restricted as long as it is a microorganism capable of producing an organic acid and examples thereof include coryneform bacteria and those bacteria belonging to the genera *Mycobacterium, Rhodococcus, Nocardia* and *Streptomyces*; however, it is more preferably a coryneform bacterium.

The coryneform bacterium is not particularly restricted as long as it is classified into coryneform bacteria, and examples thereof include those bacteria belonging to the genera *Corynebacterium, Brevibacterium* and *Arthrobacter*. Among these, those bacteria belonging to the genera *Corynebacterium* and *Brevibacterium* are preferred, and more preferred examples include those bacteria classified as *Corynebacterium glutamicum, Brevibacterium flavum, Brevibacterium ammoniagenes* and *Brevibacterium lactofermentum*.

Particularly preferred specific examples of the parent strain of the microorganism to be used in the present invention include *Brevibacterium flavum* MJ-233 (FERM BP-1497), *Brevibacterium flavum* MJ-233 AB-41 (FERM BP-1498), *Brevibacterium ammoniagenes* ATCC6872, *Corynebacterium glutamicum* ATCC31831 and *Brevibacterium lactofermentum* ATCC13869. It is noted here that, since *Brevibacterium flavum* may currently be classified as *Corynebacterium glutamicum* (Lielbl, W., Ehrmann, M., Ludwig, W. and Schleifer, K. H., Int. J. Syst. Bacteriol., 1991, vol. 41, p 255-260), in the present invention, the *Brevibacterium flavum* MJ-233 strain and its mutant strain, MJ-233 AB-41 strain, are regarded as the same as *Corynebacterium glutamicum* MJ-233 strain and *Corynebacterium glutamicum* MJ-233 AB-41 strain, respectively.

*Brevibacterium flavum* MJ-233 has been deposited as of Apr. 28, 1975, with National Institute of Bioscience and Human Technology, Agency of Industrial Science and Technology, Ministry of International Trade and Industry (currently, International Patent Organism Depositary, National Institute of Advanced Industrial Science and Technology; Tsukuba Central 6, 1-1-1 Higashi, Tsukuba, Ibaraki 305-8566, Japan) under the accession No. FERM P-3068 and converted to an international deposit under the accession No. FERM BP-1497 as of May 1, 1981, under the Budapest Treaty.

Further, the above-described microorganisms to be used as a parent strain may be not only a wild-type strain, but also any of mutant strains obtained by a conventional mutation treatment such as UV irradiation or NTG treatment and recombinant strains induced by a genetic method such as cell fusion or genetic recombination.

In the following descriptions, the aromatic carboxylic acid is assumed to be protocatechuic acid.

Protocatechuic acid is synthesized from 3-dehydrosikimate via the shikimic acid pathway where a condensation reaction between phosphoenolpyruvate, which is an intermediate metabolite of the glycolytic pathway, and erythrose-4-phosphate, which is an intermediate metabolite of the pentose phosphate pathway, is catalyzed by enzymes such as DAHP synthase, dehydroquinate synthase, dehydroquinate dehydratase and dehydroshikimate dehydratase. The synthetic pathway of protocatechuic acid is shown in FIG. 1.

The microorganism to be used in the present invention can be obtained by modifying the above-described strain so that at least one enzyme activity selected from the group consisting of DAHP synthase activity, dehydroquinate synthase activity, dehydroquinate dehydratase activity and dehydroshikimate dehydratase activity is reduced as compared to an unmodified strain.

The term "DAHP synthase activity" refers to an activity to catalyze a reaction in which phosphoenolpyruvate and erythrose-4-phosphate are condensed to yield DAHP (3-deoxy-D-arabino-heptulosonate-7-phosphate) (EC: 2.5.1.54). The phrase "modified so that the DAHP synthase activity is reduced" means that the DAHP synthase activity is lower than that of an unmodified strain such as wild-type strain. The DAHP synthase activity is reduced to preferably not higher than 30%, more preferably not higher than 10% per unit cell weight, as compared to that of an unmodified strain. Further, the DAHP synthase activity may also be completely lost. A reduction in the DAHP synthase activity can be verified by measuring the DAHP synthase activity in accordance with a known method such as the one described in Liu, et al. (Liu Y. J., Li P. P., Zhao K. X., Wang B. J., Jiang C. Y., Drake H. L. and Liu S. J., Appl. Environ. Microbiol., 2008, vol. 74(14), p 5497-5503).

The term "dehydroquinate synthase activity" refers to an activity to catalyze a reaction in which 3-dehydroquinate is produced from DAHP (3-deoxy-D-arabino-heptulosonate-7-phosphate) (EC: 4.2.3.4). The phrase "modified so that the dehydroquinate synthase activity is reduced" means that the dehydroquinate synthase activity is lower than that of an unmodified strain such as wild-type strain. The dehydroquinate synthase activity is reduced to preferably not higher than 30%, more preferably not higher than 10% per unit cell weight, as compared to that of an unmodified strain. Further, the dehydroquinate synthase activity may also be completely lost. A reduction in the dehydroquinate synthase activity can be verified by measuring the dehydroquinate synthase activity in accordance with a known method such as the one described in de Mendonca, et al. (de Mendonca J. D., Ely F., Palma M. S., Frazzon J., Basso L. A. and Santos D. S., J. Bacteriol., 2007, vol. 189(17), p 6246-6252).

The term "dehydroquinate dehydratase activity" refers to an activity to catalyze a reaction in which 3-dehydroshikimate is produced from 3-dehydroquinate (EC: 4.2.1.10). The phrase "modified so that the dehydroquinate dehydratase activity is reduced" means that the dehydroquinate dehydratase activity is lower than that of an unmodified strain such as wild-type strain. The dehydroquinate synthase activity is reduced to preferably not higher than 30%, more preferably not higher than 10% per unit cell weight, as compared to that of an unmodified strain. Further, the dehydroquinate dehydratase activity may also be completely lost. A reduction in the dehydroquinate dehydratase activity can be verified by measuring the dehydroquinate dehydratase activity in accordance with a known method such as the one described in Elsemore, et al. (Elsemore D. A. and Ornston L. N., J. Bacteriol., 1995, vol. 177(20), p 5971-5978).

The term "dehydroshikimate dehydratase activity" refers to an activity to catalyze a reaction in which protocatechuic acid is produced from 3-dehydroshikimate (EC: 4.2.1.-). The phrase "modified so that the dehydroshikimate dehydratase activity is reduced" means that the dehydroshikimate dehydratase activity is lower than that of an unmodified strain such as wild-type strain. The dehydroshikimate dehydratase activity is reduced to preferably not higher than 30%, more preferably not higher than 10% per unit cell weight, as compared to that of an unmodified strain. Further, the dehydroshikimate dehydratase activity may be completely lost as well. A reduction in the dehydroshikimate dehydratase activity can be verified by measuring the dehydroshikimate dehydratase activity in accordance with a known method such as the one described in Elsemore, et al. (Elsemore D. A. and Ornston L. N., J. Bacteriol., 1995, vol. 177(20), p 5971-5978).

A strain which has been modified so that at least one enzyme activity selected from the group consisting of DAHP synthase activity, dehydroquinate synthase activity, dehydroquinate dehydratase activity and dehydroshikimate dehydratase activity is reduced as compared to an unmodified strain can be obtained by treating the above-described parent strain with a mutagenic agent normally used in a mutation treatment, such as N-methyl-N'-nitro-N-nitrosoguanidine (NTG) or nitrous acid, and then selecting a strain in which the enzyme activity of interest is reduced.

Alternatively, such a strain may also be obtained by modifying a parent strain with the genes encoding the respective enzymes. Specifically, this can be achieved by, for example, disrupting a gene on a chromosome or modifying a promoter or an expression control sequence such as Sine-Dalgarno (SD) sequence.

A DAHP synthase gene on a chromosome is not particularly restricted as long as it encodes a protein having DAHP synthase activity, and examples thereof include genes originated from *Corynebacterium glutamicum* MJ-233 strain which comprises the nucleotide sequence shown in SEQ ID NO:7 or 9 (hereinafter, also referred to as "the aroF gene" and "the aroG gene", respectively).

Further, a dehydroquinate synthase gene, a dehydroquinate dehydratase gene and a dehydroshikimate dehydratase gene are also not particularly restricted as long as they encode a protein having the respective enzyme activity, and examples thereof include genes originated from *Corynebacterium glutamicum* MJ-233 strain, each of which comprises the nucleotide sequence shown in SEQ ID NO:11, 13 or 15 (hereinafter, also referred to as "the aroB gene", "the qsuC gene" and "the qsuB gene", respectively).

Further, the aroF gene, aroG gene, aroB gene, qsuC gene and qsuB gene may also each be a gene which encodes a protein comprising the amino acid sequence as shown in SEQ ID NO:8, 10, 12, 14 or 16 except that one or several amino acids are substituted, deleted, inserted or added, as long as the resulting protein has the respective enzyme activity. Here, the term "several amino acids" usually means 2 or more, and not more than 20 amino acids, preferably not more than 10 amino acids, more preferably not more than 5 amino acids.

Further, in accordance with the type of the microorganism to be used as a host, it is also possible to use a DAHP synthase gene, a dehydroquinate synthase gene, a dehydroquinate dehydratase gene and a dehydroshikimate dehydratase gene that are originated from a bacterium other than coryneform bacterium or other microorganism. As the DAHP synthase gene, dehydroquinate synthase gene, dehydroquinate dehydratase gene and dehydroshikimate dehydratase gene that are originated from a microorganism, for example, genes whose nucleotide sequences have already been determined or genes encoding a protein having an activity of DAHP synthase, dehydroquinate synthase, dehydroquinate dehydratase or dehydroshikimate dehydratase, which are isolated from a chromosome of a microorganism based on the homology or the like to determine the nucleotide sequences thereof, may be used. In addition, once the nucleotide sequences are determined, genes that are synthesized in accordance with the thus determined nucleotide sequences may also be used. These genes can be obtained by amplifying a region containing the respective promoter thereof and an ORF region in accordance with a hybridization method or a PCR method.

A method of disrupting the qsuB gene in a coryneform bacterium will now be described. The qsuB gene can be acquired by, for example, synthesizing a synthetic oligonucleotide based on the above-described sequence and then cloning the thus obtained oligonucleotide by PCR using a chromosomal DNA of *Corynebacterium glutamicum* as a template. A chromosomal DNA can be prepared from a DNA donor bacterium by, for example, the method of Saito and Miura (see Saito H. and Miura K., Biochim Biophys Acta., 1963, vol. 72, p 619-629; Text for Bioengineering Experiments, edited by the Society for Biotechnology, Japan, p 97-98, Baifukan, 1992).

The qsuB gene prepared in the above-described manner or a part thereof can be used for gene disruption. It is noted here that, since the gene to be disrupted may be any gene as long as it has a homology (identity) at such a level that induces homologous recombination with the qsuB gene on a chromosomal DNA of the bacterium to be disrupted, a gene having a homology to the sequence shown in SEQ ID NO:15 can also be used. Here, the "homology at such a level that induces homologous recombination" is preferably not less than 80%, more preferably not less than 90%, particularly preferably not less than 95%. Further, homologous recombination may occur between any DNAs as long as they can hybridize with the above-described gene (complementary strand of SEQ ID NO:15) under stringent conditions. Here, the stringent conditions may be, for example, those where genes are hybridized under a washing condition of conventional Southern hybridization comprising the salt concentrations equivalent to 1×SSC and 0.1% SDS at 60° C., preferably a condition comprising the salt concentrations equivalent to 0.1×SSC and 0.1% SDS at 60° C.

Further, as the aroF gene, aroG gene, aroB gene and qsuC gene, genes having a homology to the sequences shown in SEQ ID NO:7, 9, 11 and 13 (DNAs which can hybridize with the complementary strands of SEQ ID NO:7, 9, 11 and 13 under stringent conditions) can be used, respectively.

Using the above-described gene, the qsuB gene on a chromosome can be disrupted by, for example, deleting a partial sequence of the qsuB gene to prepare a defective qsuB gene which has been modified not to produce normal QsuB protein; transforming a coryneform bacterium with a DNA containing the gene; and then allowing the gene on the chromosome to undergo recombination with the defective gene. Such gene disruption by gene substitution utilizing homologous recombination has already been established and examples thereof include a method in which a linear DNA is used and a method in which a plasmid containing a temperature-sensitive replication origin is used (U.S. Pat. No. 6,303,383 and JP H05-007491A). Further the above-described gene disruption by gene substitution utilizing homologous recombination can also be performed by using a plasmid which does not have replication capacity in a host. As such a plasmid which does not have replication capacity in a coryneform bacterium, a plasmid having replication capacity in *Escherichia coli* is preferred, and examples thereof include pHSG299 (manufactured by Takara Bio Inc.) and pHSG399 (manufactured by Takara Bio Inc.). In the above, a case where the qsuB gene is disrupted in a coryneform bacterium was described; however, disruption of the aroF gene, aroG gene, aroB gene or qsuC gene as well as disruption in other bacteria can also be achieved in the same manner as described above.

In order to obtain a microorganism having a reduced ability to produce an aromatic carboxylic acid such as protocatechuic acid, as described in the above, a microorganism modified so that the activity of at least one enzyme selected from the group consisting of DAHP synthase, dehydroquinate synthase, dehydroquinate dehydratase and dehydroshikimate dehydratase is reduced may be employed; however, a microorganism which has been modified so that the dehydroshikimate dehydratase activity is reduced is preferably used. The reason therefor is as follows. When the activity of DAHP synthase, dehydroquinate synthase or dehydroquinate dehydratase is reduced, not only the synthesis of protocatechuic acid, but also the synthesis of metabolites such as phenylalnine that are synthesized by the shikimic acid pathway and required for growth become difficult, so that growth tends to be suppressed. In fact, it is reported that the growth of a coryneform bacterium having a disruption in the gene encoding DAHP synthase was inhibited on a synthetic medium (Liu Y. J., Li P. P., Zhao K. X., Wang B. J., Jiang C. Y., Drake H. L., Liu S. J., Appl. Environ. Microbiol., 2008, vol. 74(14), p 5497-5503). Accordingly, in cases where the activities of these enzymes are reduced, it is required to add an aromatic amino acid such as phenylalanine in order to allow the microorganism to grow. Meanwhile, since the shikimic acid pathway is not blocked even when the dehydroshikimate dehydratase activity is reduced, it is believed that such deterioration in growth does not occur. Accordingly, a microorganism which has been modified so that the activity of dehydroshikimate dehydratase is reduced is preferred because the amount of aromatic amino acids such as phenylalanine or organic nitrogen containing an aromatic amino acid that are required to be added for growth may be small and, therefore, such a microorganism can be grown on a simple medium such as synthetic medium, which is economical.

In order to obtain a microorganism having a reduced ability to produce an aromatic carboxylic acid such as protocatechuic acid, as described in the above, either a microorganism which has been modified so that the activity of at least one enzyme selected from the group consisting of DAHP synthase, dehydroquinate synthase, dehydroquinate dehydratase and dehydroshikimate dehydratase is reduced or a microorganism which has been modified so that the activity of shikimate dehydrogenase is enhanced may be employed.

The term "shikimate dehydrogenase activity" refers to an activity to catalyze a reaction in which shikimate is produced from 3-dehydroshikimate (EC: 1.1.1.25, 1.1.1.282, 1.1.5.8). The phrase "modified so that the shikimate dehydrogenase activity is enhanced" means that the shikimate dehydrogenase activity is higher than that of an unmodified strain such as wild-type strain. The shikimate dehydrogenase activity is increased to preferably not less than 1.5 times, more preferably not less than 3 times per unit cell weight, as compared to that of an unmodified strain. An enhancement in the shikimate dehydrogenase activity can be verified by measuring the shikimate dehydrogenase activity in accordance with a known method such as the one described in Fonseca, et al. (Fonseca I. O., Magalhaes M. L., Oliveira J. S., Silva R. G., Mendes M. A., Palma M. S., Santos D. S, and Basso L. A., Protein Expr. Purif., 2006, vol. 46(2), p 429-437).

A strain in which the shikimate dehydrogenase activity is enhanced can be obtained by treating a parent strain with a mutagenic agent normally used in a mutation treatment, such as N-methyl-N'-nitro-N-nitrosoguanidine (NTG) or nitrous acid, and then selecting a strain having an increased shikimate dehydrogenase activity.

Alternatively, such a strain may also be obtained by modifying a parent strain with the gene encoding the shikimate dehydrogenase. Specifically, the shikimate dehydrogenase activity can be enhanced by increasing the copy number of the shikimate dehydrogenase gene, and the copy number can be increased by, for example, using a plasmid or increasing the number of copies on a chromosome by a known homologous recombination method. Further, an enhancement of the shikimate dehydrogenase activity can also be achieved by introducing a mutation to a promoter of the shikimate dehydrogenase gene on a chromosome or a plasmid or by allowing the shikimate dehydrogenase gene to be highly expressed by substitution or the like thereof into a stronger promoter.

The shikimate dehydrogenase gene is not particularly restricted as long as it encodes a protein having shikimate dehydrogenase activity, and examples thereof include a gene originated from *Corynebacterium glutamicum* MJ-233 strain which comprises the nucleotide sequence shown in SEQ ID NO:17 (hereinafter, also referred to as "the qsuD gene").

Further, the qsuD gene may also be, as long as it encodes a protein having shikimate dehydrogenase activity, a DNA which hybridizes with a DNA having a sequence complementary to the above-described nucleotide sequence under stringent conditions or a homolog such as a DNA which has a homology of not less than 80%, preferably not less than 90%, more preferably not less than 95%, particularly preferably not less than 99% to the above-described nucleotide sequence. Here, the stringent conditions may be, for example, those where genes are hybridized under a washing condition of conventional Southern hybridization comprising the salt concentrations equivalent to 1×SSC and 0.1% SDS at 60° C., preferably a condition comprising the salt concentrations equivalent to 0.1×SSC and 0.1% SDS at 60° C.

Further, the qsuD gene may also be a gene which encodes a protein comprising the amino acid sequence as shown in SEQ ID NO:18 except that one or several amino acids are substituted, deleted, inserted or added, as long as the resulting protein has the shikimate dehydrogenase activity. Here, the term "several amino acids" usually means 2 or more, but not more than 20 amino acids, preferably not more than 10 amino acids, more preferably not more than 5 amino acids.

Further, a shikimate dehydrogenase gene originated from a non-coryneform bacterium, other microorganism, an animal or a plant may also be used. As the shikimate dehydrogenase gene originated from other microorganism, an animal or a plant, for example, a gene whose nucleotide sequence has already been determined or a gene encoding a protein having shikimate dehydrogenase activity which is isolated from a chromosome of a microorganism, an animal or a plant based on the homology or the like to determine the nucleotide sequence thereof, may be used. In addition, once the nucleotide sequence is determined, a gene synthesized in accordance with the thus determined nucleotide sequence may also be used. These genes can be obtained by amplifying a region containing the respective promoter thereof and an ORF region in accordance with a hybridization method or a PCR method.

By inserting the thus isolated gene encoding shikimate dehydrogenase into a known expression vector so that the gene can be expressed, a shikimate dehydrogenase expression vector is provided. By performing transformation with this expression vector, a shikimate dehydrogenase activity-enhanced strain can be obtained. Alternatively, a shikimate dehydrogenase activity-enhanced strain can also be obtained by incorporating a DNA encoding shikimate dehydrogenase into a chromosomal DNA of a host bacterium by homologous recombination or the like so that the incorporated DNA can be expressed. These transformation and homologous recombination can be carried out in accordance with a conventional method known to those skilled in the art.

When introducing a shikimate dehydrogenase gene into a chromosome or a plasmid, an appropriate promoter and more preferably a terminator are incorporated into a 5'-upstream region and a 3'-downstream region of the gene, respectively. These promoter and terminator are not particularly restricted as long as they are known to function in a bacterium to be used as a host, and they may be the promoter and terminator of the shikimate dehydrogenase gene itself or may be replaced with other promoter and terminator. The vectors, promoters, terminators and the like that can be used in a variety of bacteria are described in detail in, for example, "Fundamental Microbiology (Biseibutsugaku Kiso-kouza) 8; Genetic Engineering, Kyoritsu Shuppan Co., Ltd.".

A method of enhancing the qsuD gene in a coryneform bacterium will now be described. In cases where a coryneform bacterium is used, a recombinant plasmid capable of enhancing the expression of the qsuD gene in the coryneform bacterium can be obtained by introducing a DNA fragment containing the qsuD gene into a plasmid vector which contains a gene regulating the replication and growth functions of a plasmid in the coryneform bacterium. By transforming a coryneform bacterium such as *Corynebacterium glutamicum* MJ-233 strain with the thus obtained recombinant vector, a coryneform bacterium having an enhanced expression of the qsuD gene can be obtained. This transformation can be carried out by, for example, an electric pulse method (Vertes A. A., Inui M., Kobayashi M., Kurusu Y. and Yukawa H., Res. Microbiol., 1993, vol. 144(3), p 181-185).

A plasmid vector capable of introducing a gene into a coryneform bacterium is not particularly restricted as long as it contains at least a gene which regulates the replication and growth functions in the coryneform bacterium. Specific examples of such plasmid vector include the plasmid pCRY30 described in JP H3-210184A; the plasmids pCRY21, pCRY2KE, pCRY2KX, pCRY31, pCRY3KE and pCRY3KX, which are described in JP H2-72876A and U.S. Pat. No. 5,185,262; the plasmids pCRY2 and pCRY3 which are described in JP H1-191686A; the plasmid pAM330 described in JP S58-67679A; the plasmid pHM1519 described in JP 558-77895A; the plasmids pAJ655, pAJ611 and pAJ1844, which are described in JP S58-192900A; the plasmid pCG1 described in JP S57-134500A; the plasmid pCG2 described in JP S58-35197A; and the plasmids pCG4 and pCG11 which are described in JP 557-183799A. Thereamong, as a plasmid vector to be used in a host-vector system of a coryneform bacterium, a plasmid vector which contains a gene regulating the replication and growth functions of a plasmid in the coryneform bacterium and a gene regulating the function of stabilizing the plasmid in the coryneform bacterium is preferred. For example, the plasmids pCRY30, pCRY21, pCRY2KE, pCRY2KX, pCRY31, pCRY3KE and pCRY3KX can be suitably employed.

In the above-described recombinant plasmid or incorporation into a chromosome, a promoter used to express the qsuD gene may be any promoter as long as it functions in the coryneform bacterium, and it may also be the promoter of the qsuD gene itself. The expression level of the qsuD gene can also be adjusted by appropriately selecting the promoter. In the above, a case where a coryneform bacterium is used was described; however, enhancement of the shikimate dehydrogenase activity in other bacteria can also be achieved in the same manner as described above.

The microorganism according to the present invention may also be a bacterium which is, in addition to being modified so that the ability to produce an aromatic carboxylic acid is reduced (modification by which the activity of at least one enzyme selected from the group consisting of DAHP synthase, dehydroquinate synthase, dehydroquinate dehydratase and dehydroshikimate dehydratase is reduced or the shikimate dehydrogenase activity is enhanced), modified so that the lactate dehydrogenase (hereinafter, also referred to as "LDH") activity is reduced. The term "LDH activity" used herein refers to an activity to catalyze a reaction in which pyruvate is reduced to yield lactate (EC: 1.1.1.27). The phrase "the LDH activity is reduced" means that the LDH activity is lower than that of an unmodified strain. The LDH activity is reduced to preferably not higher than 30%, more preferably not higher than 10% per unit cell weight, as compared to that of an unmodified strain. Further, the LDH activity may also be completely lost. A reduction in the LDH activity can be verified by measuring the LDH activity in accordance with a known method such as the one described in Kanarek, et al. (Kanarek L. and Hill R. L., J. Biol. Chem., 1964, vol. 239, p 4202-4206).

Specific examples of a method for preparing a strain in which the LDH activity is reduced include the method described in JP H11-206385A which utilizes homologous recombination on a chromosome and the method in which the sacB gene is used (Schafer A., Tauch A., Jager W., Kalinowski J., Thierbach G. and Puhler A., Gene, 1994, vol. 145(1), p 69-73). A bacterium in which the LDH activity and the ability to produce an aromatic carboxylic acid are both reduced can be obtained by, for example, preparing a bacterium whose ldh gene is disrupted and then modifying the bacterium so that the ability to produce an aromatic carboxylic acid is reduced. It is noted here, however, that whichever this modification operation for reducing the LDH activity or the modification operation for reducing the ability to produce an aromatic carboxylic acid may be performed first.

Further, the microorganism to be used in the present invention may also be a bacterium which is, in addition to being modified so that the ability to produce an aromatic carboxylic acid is reduced (modification by which the activity of at least one enzyme selected from the group consisting of DAHP synthase, dehydroquinate synthase, dehydroquinate dehydratase and dehydroshikimate dehydratase is reduced or the shikimate dehydrogenase activity is enhanced), modified so that the pyruvate carboxylase (hereinafter, also referred to as "PC") activity is enhanced. The term "PC activity" used herein refers to an activity to catalyze a reaction in which pyruvate is carboxylated to yield oxaloacetate (EC: 6.4.1.1). The phrase "the PC activity is enhanced" means that the PC activity is higher than that of an unmodified strain. The PC activity is increased to preferably not less than 1.5 times, more preferably not less than 3 times per unit bacterial weight, as compared to that of an unmodified strain. An enhancement in the PC activity can be verified by measuring the PC activity in accordance with a known method such as the one described in Fisher, et al. (Fisher S. H. and Magasanik B., J. Bacteriol., 1984, vol. 158(1), p 55-62).

A strain in which the PC activity is enhanced can be prepared in the same manner as the above-described method of enhancing the shikimate dehydrogenase activity. More specifically, such a strain can be prepared by, for example, in the same manner as the method described in JP H11-196888A, introducing a pc gene into a coryneform bacterium to allow the gene to be highly expressed. As a specific pc gene, for example, the pc gene originated from *Corynebacterium glutamicum* (Peters-Wendisch P. G., Kreutzer C., Kalinowski J., Patek M., Sahm H. and Eikmanns B. J., Microbiology, 1998, vol. 144, p 915-927) may be used. Further, as the pc gene, a DNA which hybridizes with the pc gene originated from *Corynebacterium glutamicum* under stringent conditions or a DNA encoding a protein having PC activity which has a homology of not less than 80%, preferably not less than 90%, more preferably not less than 95%, particularly preferably not less than 99% to the nucleotide sequence of the pc gene can also be suitably used.

Moreover, a pc gene originated from a coryneform bacterium other than *Corynebacterium glutamicum* or other microorganism, or an animal/plant-derived pc gene can also be used. Particularly, the sequences of the pc genes originated from the following microorganisms, plants or animals are already known (references are provided below) and these pc genes can be obtained by performing hybridization in the same manner as described in the above or by amplifying the ORF region thereof by PCR.

Human [Biochem. Biophys. Res. Comm., 202, 1009-1014, (1994)]
Mouse [Proc. Natl. Acad. Sci. USA., 90, 1766-1779, (1993)]
Rat [GENE, 165, 331-332, (1995)]
Yeast; *Saccharomyces cerevisiae* [Mol. Gen. Genet., 229, 307-315, (1991)]
*Schizosaccharomyces pombe* [DDBJ Accession No. D78170]
*Bacillus stearothermophilus* [GENE, 191, 47-50, (1997)]
*Rhizobium etli* [J. Bacteriol., 178, 5960-5970, (1996)]

A bacterium in which the PC activity is enhanced and the ability to produce an aromatic carboxylic acid is reduced can be obtained by, for example, preparing a bacterium in which a pc gene is introduced and highly expressed and then modifying the bacterium so that the ability to produce an aromatic carboxylic acid is reduced. It is noted here, however, that whichever this modification operation for enhancing the PC activity or the modification operation for reducing the ability to produce an aromatic carboxylic acid may be performed first.

Further, the microorganism according to the present invention may also be a bacterium which is, in addition to being modified so that the ability to produce an aromatic carboxylic acid is reduced (modification by which the activity of at least one enzyme selected from the group consisting of DAHP synthase, dehydroquinate synthase, dehydroquinate dehydratase and dehydroshikimate dehydratase is reduced or the shikimate dehydrogenase activity is enhanced), modified so that the activity of at least one enzyme selected from the group consisting of acetate kinase (hereinafter, also referred to as "ACK") and phosphotransacetylase (hereinafter, also referred to as "PTA") is reduced.

The term "PTA activity" refers to an activity to catalyze a reaction in which phosphate is transferred to acetyl-CoA to yield acetyl phosphate (EC: 2.3.1.8). The phrase "modified so that the PTA activity is reduced" means that the PTA activity is lower than that of an unmodified strain. The PTA activity is reduced to preferably not higher than 30%, more preferably not higher than 10% per unit cell weight, as compared to that of an unmodified strain. Further, the PTA activity may also be completely lost. A reduction in the PTA activity can be verified by measuring the PTA activity in accordance with a known method such as the one described in Klotzsch (Klotzsch H. R., Meth. Enzymol., 1969, vol. 12, p 381-386).

The term "ACK activity" refers to an activity to catalyze a reaction in which acetic acid is produced from acetyl phosphate and ADP (EC: 2.7.2.1). The phrase "modified so that the ACK activity is reduced" means that the ACK activity is lower than that of an unmodified strain. The ACK activity is reduced to preferably not higher than 30%, more preferably not higher than 10% per unit cell weight, as compared to that of an unmodified strain. Further, the ACK activity may be completely lost as well. A reduction in the ACK activity can be verified by measuring the ACK activity in accordance with a known method such as the one described in Ramponi (Ramponi G., Meth. Enzymol., 1975, vol. 42, p 409-426).

The activity of only either one of PTA and ACK may be reduced; however, in order to efficiently reduce the by-production of acetic acid, it is more preferred that the activities of both enzymes be reduced.

It is noted here that, in *Corynebacterium glutamicum* (including those bacteria classified as *Brevibacterium flavum*), as described in Microbiology. 1999 February; 145(Pt 2):503-13, since both enzymes of PTA and ACK are encoded by the pta-ack operon (GenBank Accession No. X89084), the activities of both enzymes can be reduced by disrupting the pta gene.

A strain in which the activities of PTA and ACK are reduced can be obtained by disrupting the genes of these enzymes in accordance with a known method such as a method which utilizes homologous recombination or the method in which the sacB gene is used (Schafer A., Tauch A., Jager W., Kalinowski J., Thierbach G. and Puhler A., Gene, 1994, vol. 145(1), p 69-73). Specifically, such a strain can be obtained by the method disclosed in JP 2006-000091A. As the pta gene and the ack gene, in addition the above-described gene having the nucleotide sequence of GenBank Accession No. X89084, a gene having a homology at such a level that induces homologous recombination with the pta gene and the ack gene on the host chromosome can also be used. Here, the "homology at such a level that induces homologous recombination" is preferably not less than 80%, more preferably not less than 90%, particularly preferably not less than 95%. Further, homologous recombination may occur between any DNAs as long as they can hybridize with the above-described genes under stringent conditions.

A bacterium in which the activity of at least one enzyme selected from the group consisting of PTA and ACK as well as the ability to produce an aromatic carboxylic acid are both reduced can be obtained by, for example, preparing a bacterium whose pta gene and ack gene are disrupted and then modifying the bacterium so that the ability to produce an aromatic carboxylic acid is reduced. It is noted here, however, that whichever this modification operation for reducing the activities of PTA and ACK or the modification operation for reducing the ability to produce an aromatic carboxylic acid may be performed first.

Further, the microorganism used in the present invention may also be a bacterium which is obtained by performing two or more of the above-described modifications in combination with the modification for reducing the ability to produce an aromatic carboxylic acid (modification by which the activity of at least one enzyme selected from the group consisting of DAHP synthase, dehydroquinate synthase, dehydroquinate dehydratase and dehydroshikimate dehydratase is reduced or the shikimate dehydrogenase activity is enhanced). When plural modifications are performed, their order is not particularly restricted.

<Method of Producing Organic Acid>

The method of producing an organic acid according to the present invention comprises the step of allowing the above-described microorganism or a treated cell thereof to act on an organic raw material to produce an organic acid. Particularly, it is preferred that an organic acid be produced by allowing the above-described microorganism or a treated cell thereof to act on an organic raw material and then the resulting organic material be recovered.

Examples of the types of organic acids that can be produced and examples of preferred organic acids are as described in the above.

In cases where the above-described microorganism is used in the production of an organic acid, the microorganism may be cultured on a solid slant medium such as an agar medium and then directly used for the reaction; however, it is preferred that the microorganism be cultured in advance in a liquid medium (seed culture) and then used. The medium used for the seed culture may be any conventional medium used for culturing a microorganism. For example, a common culture medium which is prepared by adding natural nutrient sources, such as meat extract, yeast extract and peptone, to a composition composed of inorganic salts such as ammonium sulfate, potassium phosphate and magnesium sulfate can be employed. After the seed culture, it is preferred that the resulting bacterial cells be recovered by centrifugation, membrane separation or the like and then used for the reaction to produce an organic acid. An organic acid may be produced by allowing the seed-cultured microorganism to react with an organic raw material while allowing the microorganism to grow in a medium containing the organic raw material. Alternatively, an organic acid may also be produced by allowing the bacterial cells obtained by culturing in advance to react with an organic raw material in a reaction solution containing the organic raw material.

In the present invention, it is also possible to use a treated cell of a microorganism. Examples of the treated cell include bacterial cells immobilized with acrylamide, carrageenan or the like; a homogenate prepared by pulverizing bacterial cells; a centrifugation supernatant thereof; and a fraction obtained by partially purifying the supernatant with ammonium sulfate or the like.

The organic raw material to be used in the production method according to the present invention is not particularly restricted as long as it is a carbon source which can be assimilated by the microorganism of the present invention to produce succinic acid. As the organic raw material, usually, a fermentable sugar, for example, a carbohydrate such as galactose, lactose, glucose, fructose, glycerol, sucrose, saccharose, starch or cellulose or a polyalcohol such as glycerin, mannitol, xylitol or ribitol is used. Thereamong, glucose, sucrose or fructose is preferably used, and glucose or sucrose is particularly preferably used.

Further, a saccharified starch solution, molasses or the like, which contains the above-described fermentable sugar, may also be used, and specifically, a sugar solution collected from a plant such as sugarcane, sugar beet or sugar maple is preferred.

These sugars may be used individually or in combination. The concentration at which the above-described sugar is used is not particularly restricted; however, it is advantageous to increase the concentration as much as possible within the range which does not inhibit the production of succinic acid. The concentration of the above-described sugar is, with respect to the reaction solution, usually not lower than 5% (W/V), preferably not lower than 10% (W/V), and on another front, usually not higher than 30% (W/V), preferably not higher than 20% (W/V). Further, the above-described sugar may also be further added in response to a decrease thereof associated with the progression of the reaction.

The reaction solution containing the above-described organic raw material is not particularly restricted and it may be, for example, a medium for culturing a microorganism or a buffer solution such as phosphate buffer. The reaction solution is preferably an aqueous solution containing a nitrogen source, an inorganic salt and the like. Here, the nitrogen source is not particularly restricted as long as it can be assimilated by the microorganism of the present invention to produce succinic acid, and specific examples of such nitrogen source include a variety of organic and inorganic nitrogen compounds such as ammonium salts, nitrates, urea, soybean hydrolysates, casein digests, peptone, yeast extracts, meat extracts and corn steep liquors. As the inorganic salt, a variety of phosphates, sulfates and metal salts of magnesium, potassium, manganese, iron, zinc and the like may be used. Further, a growth-promoting factor(s) such as vitamins (e.g., biotin, pantothenic acid, inositol and nicotinic acid), nucleotides and amino acids may be added as required. Moreover, in order to suppress foam formation during reaction, it is desired to add an appropriate amount of a commercially available antifoaming agent to the reaction solution.

The reaction solution also contains a carbonate ion, bicarbonate ion or carbon dioxide gas in addition to the above-described organic raw material, nitrogen source and inorganic salt. The carbonate ion or the bicarbonate ion is supplied from magnesium carbonate, sodium carbonate, sodium bicarbonate, potassium carbonate, potassium bicarbonate or the like, which can also be used as a neutralizing agent; however, as required, the ion may also be supplied from carbonic acid or bicarbonic acid, or a salt thereof, or carbon dioxide gas. Specific examples of the salt of carbonic acid or bicarbonic acid include magnesium carbonate, ammonium carbonate, sodium carbonate, potassium carbonate, ammonium bicarbonate, sodium bicarbonate and potassium bicarbonate. Further, the carbonate ion or bicarbonate ion is added at a concentration of usually not lower than 1 mM, preferably not lower than 2 mM, more preferably not lower than 3 mM, and on another front, usually not higher than 500 mM, preferably not higher than 300 mM, more preferably not higher than 200 mM. In cases where carbon dioxide gas is added, it is contained in an amount of usually not less than 50 mg, preferably not less than 100 mg, more preferably not less than 150 mg, and on another front, usually not more than 25 g, preferably not more than 15 g, more preferably not more than 10 g, per 1 L of the solution.

The pH of the reaction solution can be adjusted by adding thereto, for example, sodium carbonate, sodium bicarbonate, potassium carbonate, potassium bicarbonate, magnesium carbonate, sodium hydroxide, calcium hydroxide, magnesium hydroxide or ammonia. The pH of the reaction is usually not lower than 5, preferably not lower than 5.5, more preferably not lower than 6, and on another front, not higher than 10, preferably not higher than 9.5, more preferably not higher than 9.0. Thus, during the reaction as well, the pH of the reaction solution is adjusted as required within the above-described range by adding thereto an alkaline substance, carbonate, urea or the like.

The optimum growth temperature of the microorganism to be used in the present reaction is not particularly restricted as long as it is a temperature at which the microorganism grows optimally; however, it is usually not lower than 25° C. but usually not higher than 35° C., preferably not higher than 32° C., particularly preferably not higher than 30° C. The term "optimum growth temperature" refers to a temperature at which the fastest growth rate is attained under the conditions used for the production of succinic acid.

Further, as a method of preparing bacterial cells more suitable for the production of succinic acid, the method described in JP 2008-259451A, in which culturing is performed by alternately repeating depletion and replenishment of a carbon source at short intervals, can also be employed.

The amount of the microorganism to be used in the reaction is not particularly restricted; however, in terms of the wet cell weight, the microorganism is used in an amount of usually not less than 1 g/L, preferably not less than 10 g/L, more preferably not less than 20 g/L, and on another front, usually not more than 700 g/L, preferably not more than 500 g/L, more preferably not more than 400 g/L. The reaction time is not particularly restricted; however, it is usually not short than 1 hour, preferably not shorter than 3 hours, and usually not longer than 168 hours, preferably not longer than 72 hours.

During the seed culturing of a microorganism, it is required that oxygen be supplied by aeration and stirring. On the other hand, although the reaction for producing an organic acid such as succinic acid may be carried out with aeration and stirring, it may also be carried out under an anaerobic atmosphere where aeration is not performed and oxygen is thus not supplied. Here, the condition "under an anaerobic atmosphere" can be attained by, for example, a method in which the reaction is carried out in a closed container with no aeration, a method in which the reaction is carried out with supply of an inert gas such as nitrogen gas or a method in which the reaction is carried out while aerating the system with a carbon dioxide-containing inert gas.

By such a microbial reaction as described in the above, an organic acid such as succinic acid, fumaric acid, malic acid or pyruvic acid is produced and accumulated in the reaction solution.

The amount of generated protocatechuic acid is, with respect to the amount of succinic acid produced in the culture medium after the reaction performed by allowing the microorganism of the present invention or a treated cell thereof to act on an organic raw material, usually not more than 500 ppm, preferably not more than 300 ppm, more preferably not more than 150 ppm, still more preferably not more than 75 ppm, particularly preferably not more than 50 ppm. There is no particular restriction with regard to the lower limit.

Further, the amount of generated uvitonic acid is, with respect to the amount of succinic acid produced in the culture medium after the reaction performed by allowing the microorganism of the present invention or a treated cell thereof to act on an organic raw material, usually not more than 500 ppm, preferably not more than 300 ppm, more preferably not more than 150 ppm, still more preferably not more than 75 ppm, particularly preferably not more than 50 ppm. There is no particular restriction with regard to the lower limit.

It is noted here that, also in cases where an organic acid other than succinic acid is produced, the concentration of protocatechuic acid and that of uvitonic acid are each, with respect to the organic acid of interest in the culture medium after the reaction, usually not more than 500 ppm, preferably not more than 300 ppm, more preferably not more than 150 ppm, still more preferably not more than 75 ppm, particularly preferably not more than 50 ppm.

The organic acid accumulated in the reaction solution (culture medium) can be recovered therefrom in accordance with a conventional method. The method of recovering from an organic acid from the reaction solution is not particularly restricted as long as a composition containing the desired organic acid can be obtained. By removing the microorganism, water and/or impurities from the reaction solution, an organic acid can be recovered.

The method of removing the microorganism, water and/or impurities is not particularly restricted and the removal can be achieved by a known method such as concentration, extraction, crystallization, an activated carbon treatment, a hydrogenation treatment or an ion-exchange column treatment or by an arbitrary combination of these known methods.

In the method of producing an organic acid according to the present invention, since the production of an aromatic carboxylic acid which is conventionally difficult to be removed by a crystallization treatment is reduced, it is preferred that the process of recovering an organic acid includes a crystallization treatment.

One example of such method of recovering an organic acid which includes crystallization is a method in which a microorganism is removed from a reaction solution and then, after concentrating the resulting reaction solution and extracting an organic acid as required, the resultant is subjected to crystallization, solid-liquid separation and drying. After the solid-liquid separation, for example, an activated carbon treatment, a hydrogenation treatment and/or an ion-exchange column treatment may also be performed.

A method of obtaining an organic acid, succinic acid, will now be described. However, the method of obtaining succinic acid is not restricted to the following description.

<Concentration>

In the present invention, a fermentation liquid obtained after the microbial reaction may also be concentrated as appropriate in consideration of the operability and efficiency in the subsequent purification step. The concentration method is not particularly restricted and examples thereof include a method in which an inert gas is allowed to circulate; a method in which water is distilled away by heating; a method in which water is distilled away under reduced pressure; and a combination of these methods. Further, the concentration operation may be performed in either a batch system or a continuous system.

<Removal of Microorganism>

In cases where a fermentation liquid is used in the method of the present invention, it is preferred that the fermentation liquid be one obtained after the removal of microorganism. The method of removing a microorganism is not particularly restricted and, for example, sedimentation separation, centrifugation, filtration separation and a method in which these techniques are combined can be employed. Industrially, the removal of microorganism is carried out by a method such as centrifugation or a membrane-filtration separation. As for the centrifugation, for example, centrifugal sedimentation or centrifugal filtration can be used. In the centrifugation, the operating conditions thereof are not particularly restricted; however, the separation is usually performed at a centrifugal force of 100 G to 100,000 G. Further, the operation may be performed in either a batch system or a continuous system.

Further, in the membrane-filtration separation, for example, microfiltration and/or ultrafiltration can be employed. The material of the membrane is not particularly restricted and, for example, an organic film of polyolefin, polysulfin, polyacrylonitrile, polyvinylidene fluoride or the like, or a membrane made of an inorganic material such as ceramic can be used. Further, the operation method may either be a dead-end type or a cross-flow type. In the membrane-filtration separation, since a microorganism often causes clogging of the membrane, for example, a method in which membrane filtration is performed after roughly removing the microorganism by centrifugation or the like may be employed as well.

In the production method according to the present invention, in cases where a neutralizing agent is used in the microbial reaction as described in the above, a salt of succinic acid is obtained, which is then converted into the desired succinic acid. This conversion into succinic acid may also be performed by a reactive crystallization method which utilizes a weakly acidic organic acid having an acid dissociation constant (pKa) higher than that of the desired succinic acid. Examples of such organic acid include acetic acid.

Further, alternatively, an inorganic acid may be used to convert the salt of succinic acid obtained in the above-described manner into succinic acid. Examples of the inorganic acid to be used in this method include sulfuric acid, hydrochloric acid, carbonic acid, phosphoric acid and nitric acid. More specifically, in the case of succinic acid fermentation, when fermentation is carried out while neutralizing the produced succinic acid with ammonia or magnesium hydroxide, ammonium succinate or magnesium succinate is produced in the resulting fermentation liquid. By treating such a fermentation liquid containing ammonium succinate or magnesium succinate with sulfuric acid or the like, a succinic acid-containing aqueous solution can be obtained.

In the present invention, the term "succinic acid-containing solution" or "succinic acid-containing aqueous solution" refers to a solution or an aqueous solution which mainly contains succinic acid derived from a biomass resource. Accordingly, a solution or an aqueous solution which mainly contains the above-described salt of succinic acid, such as ammonium succinate or magnesium succinate, is indicated as "succinate-containing solution" or "succinate-containing aqueous solution". The term "mainly contain" used herein refers to a condition in which the solution or the aqueous solution contains the subject component in an amount of usually not less than 50% by weight, preferably not less than 60% by weight, more preferably not less than 70% by weight, particularly preferably not less than 90% by weight, with respect to the total weight of all components except the solvent.

<Extraction>

In the present invention, from an aqueous solution which contains succinic acid obtained by conversion with the above-described inorganic acid, succinic acid may be extracted by using, but not particularly limited to, an organic solvent.

The organic solvent to be used in this method is usually an organic solvent which has an inorganic value/organic value ratio (I/O value) of 0.2 to 2.3 and a boiling point of not lower than 40° C. at normal pressure, more preferably an organic solvent which has an I/O value of 0.3 to 2.0 and a boiling point of not lower than 40° C. at normal pressure, still more preferably an organic solvent which has an I/O value of 0.3 to 2.0 and a boiling point of not lower than 60° C. at normal pressure. By using such an organic solvent, succinic acid can be selectively extracted and efficiently separated from sugars and amino acids. Further, by using an organic solvent having a boiling point of not lower than 40° C. at normal pressure, it becomes possible to avoid the risk of the solvent being vaporized and ignited and a problem of a decrease in the efficiency of succinic acid extraction due to vaporization of the solvent as well as a problem of difficulty to recycle the solvent.

The inorganic value and the organic value are proposed by Organic Conceptual Diagram ("Systematic Organic Qualitative Analysis", Fujita A., Kazamashobo Co., Ltd. (1974)). The ratio of the inorganic value and the organic value is determined by calculating the respective values based on the numerical values predetermined for the functional groups constituting the organic compound of interest.

Examples of the organic solvent which has an I/O value of 0.2 to 2.3 and a boiling point of not lower than 40° C. at normal pressure include ketone-based solvents such as methyl ethyl ketone, methyl isobutyl ketone and acetone; ether-based solvents such as tetrahydrofuran and dioxane; ester-based solvents such as ethyl acetate; nitrile-based solvents such as acetonitrile; and alcohols having a carbon chain of 3 or more carbon atoms, such as propanol, butanol and octanol.

The I/O value and boiling point of each solvent are shown below.

|  | I | O | I/O | Boiling point |
|---|---|---|---|---|
| Tetrahydrofuran | 30 | 80 | 0.375 | 66.0 |
| Methyl ethyl ketone | 65 | 60 | 1.083 | 79.6 |
| Methyl isobutyl ketone | 65 | 120 | 0.542 | 94.2 |
| Acetone | 65 | 40 | 1.625 | 56.1 |
| Acetonitrile | 70 | 40 | 1.750 | 81.1 |
| Ethyl acetate | 85 | 80 | 1.063 | 77.2 |
| Propanol | 100 | 60 | 1.667 | 97.2 |
| Isobutanol | 100 | 70 | 1.429 | 108.0 |
| Octanol | 100 | 160 | 0.625 | 179.8 |
| Dioxane | 40 | 80 | 0.500 | 101.3 |

In the extraction step, the organic solvent is added in a volume of, with respect to 1 volume of the succinic acid-containing aqueous solution, usually not less than 0.5, preferably not less than 1 and usually not more than 5, preferably not more than 3.

The temperature of the extraction step may be any temperature as long as it is a temperature at which succinic acid can be extracted; however, it is usually not lower than 10° C., preferably not lower than 20° C., while normally not higher than 90° C., preferably not higher than 85° C.

By the extraction step, succinic acid is recovered in the organic solvent and impurities such as sugars, elemental nitrogen originated from fermentation, ammonia originated from the fermentative bacterium, sulfur-containing impurities and metal cations are separated to some extent. Here, in order to extract succinic acid more efficiently, the extraction treatment with an organic solvent may be repeated a plurality of times, or countercurrent extraction may be performed.

<Removal of Impurities>

It is important that, in addition to the elemental nitrogen contained in the biomass resource, the amount of many impurities such as elemental nitrogen and ammonia originated from the fermentative bacterium, sulfur-containing impurities and metal cations be reduced from the succinic acid-containing fermentation liquid by purification. Further, it is also important to reduce the amount of impurities showing absorption in the ultraviolet region of 250 to 300 nm, particularly the amount of impurities containing an aromatic carboxylic acid, to a level where an average absorbance of 0.05 or lower is attained (see JP 2010-100617A).

In order to reduce the impurities contained in succinic acid that show absorbance in the ultraviolet region of 250 to 300 nm, particularly aromatic dicarboxylic acids, to a level where the average absorbance becomes 0.05 or lower, it is usually required to subject the succinic acid produced in the above-described manner to a combination of purification treatments such as a crystallization treatment, an activated carbon treatment, a hydrogenation treatment and a drying treatment. However, since the succinic acid-containing solution obtained by the fermentation method (organic acid production method) according to the present invention contains a markedly small amount of the above-described impurities as compared to a solution obtained by a conventional fermentation method (organic acid production method), the purification step of a crystallization treatment, an activated carbon treatment and the like can be reduced and the conditions thereof can be relaxed, so that the cost of producing an organic acid such as succinic acid can be reduced and the yield thereof can be improved, which are preferred.

<Crystallization>

In the present invent, succinic acid may also be recovered by crystallization from the succinic acid-containing solution obtained by the reaction. By performing a crystallization operation, the amount of aromatic carboxylic acids such as protocatechuic acid can be further reduced. In addition, in cases where crystallization is performed, as compared to a case where a conventional microorganism is employed, the number of crystallization operations can be reduced, which is useful.

In the present invention, the term "succinic acid crystallization" refers to an operation in which crystals of succinic acid are formed from a succinic acid-containing solution by changing the solubility of succinic acid with an application of a modification of some sort to the succinic acid-containing solution. For the succinic acid crystallization, any method may be employed as long as it is an operation which allows crystals of succinic acid to be formed from a succinic acid-containing fluid. More specifically, examples of such method include a cooling crystallization method in which succinic acid is precipitated by changing the temperature of a succinic acid-containing solution to utilize the temperature dependency of the solubility of succinic acid; a concentration-crystallization method in which succinic acid is precipitated out by evaporating a solvent from a solution by heating, pressure reduction or the like to thereby increase the concentration of succinic acid in the solution; a poor solvent crystallization method in which succinic acid is precipitated out by adding a third component (poor solvent), which reduces the solubility of succinic acid, to a succinic acid-containing solution; and a combination of these methods.

Further, in cases where the succinic acid-containing solution also contains a salt of succinic acid, crystals of succinic acid can be formed by adding a strong acid such as sulfuric acid or hydrochloric acid to the succinic acid-containing solution so as to convert the salt of succinic acid into succinic acid of non-dissociated form and then performing the above-described methods, such as cooling, concentration and addition of a poor solvent, in combination.

As for the cooling crystallization, examples of its cooling method include a method in which a succinic acid-containing solution is cooled by allowing it to circulate through an external heat exchanger or the like; a method in which a tube (inner coil) through which a coolant passes through is put into a succinic acid-containing solution; and a method in which the internal pressure of an apparatus is reduced to allow a solvent contained in a solution to be vaporized and cool the solution by means of the vaporization heat of the solvent. Thereamong, the method in which the internal pressure of an apparatus is reduced to allow a solvent contained in a solution to be vaporized and cool the solution by means of the vaporization heat of the solvent is preferred because not only inhibition of heat transfer, which is caused by succinic acid precipitating at the heat exchange interface, can be prevented, but also succinic acid can be concentrated in the solution. This method is preferred also from the standpoint of crystallization yield.

The concentration of succinic acid contained in the succinic acid-containing solution to be supplied to a crystallization bath is preferably 10% by weight to 45% by weight, more preferably 15% by weight to 40% by weight, particularly preferably 20% by weight to 35% by weight.

As a crystallization solvent, for example, water; an organic acid such as acetic acid or propionic acid; an ester such as ethyl acetate; an alcohol such as methanol, ethanol, propanol, isopropanol, butanol, 2-ethyl-1-hexanol or isobutanol; an ether such as diethyl ether, di-n-butyl ether, diisopropyl ether, di-n-butyl ether, tetrahydrofuran or dioxane; a ketone such as acetone, methyl ethyl ketone or diethyl ketone; a nitrile such as acetonitrile; or a mixture of these solvents can be employed. Thereamong, water is most preferred. As water, for example, deionized water, distilled water, river water, well water or tap water is usually used.

The temperature of a succinic acid-containing fluid in the crystallization bath at the time of crystallization (hereinafter, may be referred to as "the crystallization temperature") is set to be a temperature at which succinic acid is crystallized from the succinic acid-containing fluid and it is usually 5° C. to 60° C., preferably 10° C. to 50° C. When the crystallization temperature is lower than 5° C., although succinic acid can be obtained in a high yield, an extremely large equipment is required for cooling. In addition, in a method where cooling is performed by circulating a coolant through a jacket or an inner coil, the difference in the temperature between succinic acid slurry and the coolant becomes excessively large at the heat-transfer surface to cause severe scaling, which is not desired. Thus, in the method where cooling is performed by circulating a coolant through a jacket or an inner coil, from the standpoint of preventing scaling, it is desired that the difference in the temperature between the succinic acid slurry and the coolant at the heat-transfer surface be set to be usually not larger than 20° C., preferably not larger than 10° C.

Further, the internal pressure of the crystallization bath to be used in the method in which crystallization is performed under reduced pressure is determined in accordance with the desired crystallization temperature, and it is usually 0.5 kPa to 20 kPa, preferably 1 kPa to 15 kPa, particularly preferably 1.5 kPa to 10 kPa. When the pressure is low, the temperature inside the crystallization bath can be further lowered and the crystallization efficiency can thus be improved; however, depending on the concentration of the succinic acid-containing fluid to be supplied, the slurry concentration in the crystallization bath may become excessively high, so that the handling thereof and/or pressure control may become difficult. Furthermore, the equipment to be used for pressure reduction is limited and the equipment cost is thus increased in general, which is not economically preferred. For example, in cases where steam ejectors are used for pressure reduction, an increase in the degree of pressure reduction leads to an increase in the equipment cost due to, for example, the necessity for increasing the number of the steam ejectors. On the other hand, when the pressure is high, the temperature inside the crystallization bath becomes high, so that the slurry concentration in the crystallization bath becomes excessively low to impair the crystallization efficiency. A vacuum-generating device can be selected from known means in accordance with the desired pressure as well as the presence or absence of a solvent to be evaporated with water, the type of the solvent and the like. Examples of the known means include those which are described in Design and Operation Series No. 3, revised, Crystallization (Sekkei-Sosa Series No. 3, kaitei, Shoseki; Kagaku Kogaku Sha, p. 292-293), such as water, steam ejectors and oil-sealed rotary vacuum pumps.

The crystallization operation may be performed in a batch system where, after loading the total amount of the succinic acid-containing fluid to be crystallized into the crystallization bath, the fluid is subjected to crystallization and then the total amount of the resulting fluid is recovered. Alternatively, the crystallization operation may be performed in a continuous system where, in order to prevent the crystallization bath from being emptied during the crystallization operation, the succinic acid-containing fluid is supplied and removed as appropriate while performing the crystallization operation.

In cases where crystallization is performed in a continuous system, in order to prevent the crystallization bath from being emptied, the supply of the succinic acid-containing fluid to the crystallization bath is carried out by, for example, a method in which the fluid is continuously or intermittently supplied with pressure by utilizing a liquid feed pump or a pressure difference. The succinic acid solution is usually supplied at such a rate at which the average residence time thereof in the crystallization bath is 0.5 hour to 10 hours. When the residence time in the crystallization bath is short, the supersaturation degree of succinic acid in the bath is increased, so that microcrystals are formed in a large amount. In addition, since the slurry is removed from the crystallization bath while maintaining a degree of supersaturation, there may arise problems of scaling and the like in the subsequent steps. Meanwhile, an excessively long residence time is also inefficient since it requires an unnecessarily large crystallization bath.

In cases where crystallization is performed in a continuous system, usually, the resulting succinic acid is recovered from the crystallization bath in the form of a slurry along with the succinic acid-containing fluid. In this case, the recovery is carried out by, for example, a method in which a slurry is, by means of pressurized transfer or the like which utilizes a pressure difference, continuously or intermittently recovered into a receiver tank having a pressure lower than that of the slurry pump or crystallization bath, while appropriately comparing the recovered amount and the supplied amount of the succinic acid-containing fluid so that the crystallization bath does not become empty.

In order to supply and recover the succinic acid-containing fluid to and from the crystallization bath in such a manner that the crystallization bath does not become empty, for example, a method in which the amount of supply and that of recovery are controlled to be the same or a method in which a fluid level sensor or the like is used to repeat an operation of supplying the fluid when the fluid level in the crystallization bath has declined to a certain level and an operation of removing the fluid when the fluid level has risen to a certain level can be employed.

In the crystallization operation, in order to control the particle size distribution of the resulting succinic acid crystals, it is desired that nucleation and crystal growth of succinic acid be controlled. The nucleation and crystal growth of succinic acid is usually controlled by adjusting the supersaturation degree of succinic acid in the bath and, for this purpose, a method in which the crystallization time is controlled is usually employed. The crystallization time is usually 0.5 hour to 10 hours, preferably 1 hour to 5 hours. For example, in cases where cooling crystallization operation is performed in a batch system, it is desired that the succinic acid-containing fluid be cooled to a prescribed temperature over a period of 0.5 hour to 5 hours and then aged for a period of 0.1 hour to 5 hours. In this process, the rate at which the succinic acid-containing fluid is cooled is usually 0.05° C./min to 2° C./min, preferably 0.1° C./min to 1.5° C./min, particularly preferably 0.2° C./min to 1° C./min. Further, in the cases where cooling crystallization operation is performed in a continuous system, it is desired that the average residence time of the succinic acid-containing fluid be 0.5 hour to 10 hours, preferably 1 hour to 5 hours. When the crystallization time or the average residence time is short, the supersaturation degree of succinic acid in the bath is increased and the nucleation rate becomes high, so that microcrystals are formed in a large amount. In addition, since the slurry is removed from the crystallization bath while maintaining a degree of supersaturation, there may arise problems of scaling and the like in the subsequent steps. Meanwhile, an excessively long crystallization time is also inefficient since it requires an unnecessarily large crystallization bath.

(Crystallization Bath)

The constitution of the crystallization bath is not particularly restricted as long as it is a vessel equipped with a stirring device. As the crystallization bath, a vessel having a conventionally known stirring device may be employed; however, a cylindrical vessel having a bottom is preferably employed. Further, in order to attain efficient shearing of the slurry, it is preferred that baffle plates be arranged inside the bath. Moreover, in order to control the flow inside the crystallization bath, a vessel having a cylindrical guide such as a guide called "draft tube" can also be employed.

The shape of the vessel is not particularly restricted; however, in order to make the slurry more uniform in the apparatus and to attain more efficient shearing of the slurry, the vessel has a ratio between the diameter and the height (L/D) of usually 0.5 to 3, preferably 0.7 to 2.5, particularly preferably 1 to 2.

(Stirring Device)

As a stirring device, one which is equipped with a stirring blades is employed. The stirring blade is not required to be a special blade and any known stirring blade can be used. The stirring blade is selected from, for example, shearing-type blades such as paddle blades and turbine blades; and discharge-type blades such as sweep-back blades, Pfaudler impellers, Maxblend Blade (registered trademark; Sumitomo Heavy Industries, Ltd.) and Fullzone Blade (registered trademark; Shinko Pantec Co., Ltd.).

The size of the stirring blade is also not particularly restricted, and another stirring device which circulates the fluid may also be used in combination of the stirring device equipped with a stirring blade.

As such stirring device, for example, a device which allows the succinic acid-containing solution transferred from the crystallization bath to be circulated back to the crystallization bath by means of a fluid transfer pump such as a centrifugal pump can be employed.

The stirring of the crystallization bath is not particularly restricted as long as the crystals of succinic acid are kept flowing without settling in the crystallization bath. From the standpoints that the purity of the resulting succinic acid can be improved and that succinic acid crystals having a more uniform particle size can be obtained, crystallization is performed under such stirring conditions where the power required for stirring a unit volume of the succinic acid-containing solution (hereinafter, may be abbreviated as "Pv") is 0.2 kW/m$^3$ to 5 kW/m$^3$, preferably 0.4 kW/m$^3$ to 3 kW/m$^3$.

(Solid-Liquid Separation)

After the crystallization, the resulting succinic acid slurry can be subjected to a solid-liquid separation treatment in accordance with a known method to separate succinic acid crystals from the mother liquor. The separation method is not particularly restricted and examples thereof include filtration separation and sedimentation separation. Further, the separation operation may be performed either batchwise or continuously. Examples of an efficient solid-liquid separator include continuous-type centrifugal filtration apparatuses and centrifugal settlers such as decanters. In addition, depending on the desired purity of succinic acid, a wet cake recovered by the solid-liquid separation may be rinsed with cold water or the like.

(Drying)

The succinic acid recovered by crystallization can be dried by a conventional method depending on the application thereof. Generally, the succinic acid is dried to a water content of usually not less than 0.1% by weight, preferably not less than 0.2% by weight, and on another front, usually not higher than 2% by weight, preferably not higher than 1%. The drying method is not particularly restricted and, for example, a convection heating-type dryer such as a band dryer or a fluidized-bed dryer, or a conductive heat transfer-type dryer such as a drum dryer can be employed. A fluidized-bed dryer is particularly preferred since it is capable of performing a continuous treatment in a large quantity and the breakage of crystals in the process of drying treatment is limited. Further, when a fluidized-bed dryer is used, from the standpoint of preventing the succinic acid from causing dust explosion, it is preferred that the drying be performed under nitrogen supply and that the atmosphere be controlled to have an oxygen concentration of not higher than 12%. Moreover, since succinic anhydride may be generated as a result of intramolecular dehydration, the succinic acid is dried so that the temperature thereof during the drying process is maintained at preferably not higher than 100° C., more preferably not higher than 90° C., still more preferably not higher than 80° C.

Specific examples of a crystallization apparatus include the one shown in FIG. 4 which comprises an aqueous succinic acid solution feed tank; a crystallization bath having two rows of four baffle plates and four inclined paddle blades (stirring blades); a slurry recovery tank and the like.

<Activated Carbon Treatment>

In cases where an activated carbon treatment is performed, as the activated carbon to be used, any known activated carbon such as a coal-based activated carbon, a wood-based activated carbon, a coconut shell-based activated carbon or a resin-based activated carbon can be employed. In addition, activated carbons that are obtained by activating a variety of these material activated carbons, such as coal-based, wood-based, coconut shell-based and resin-based activated carbons, in accordance with a method such as a gas activation method, a steam activation method or a chemical activation method using zinc chloride, phosphoric acid or the like, can also be used.

Specific examples of such activated carbon include Calgon CPG, Calgon CAL, Calgon SGL, Diasorb W, Diahope MS10, Diahope M010, Diahope MS16, Diahope 6MD, Diahope 6MW, Diahope 8ED, Diahope ZGN4 and Centur, all of which are manufactured by Calgon-Mitsubishi Chemical Corporation; GAC, GAC PLUS, GCN PLUS, C GRAN, RO, ROX, DARCO, CN, SX, SXPLUS, SA, SX, PK and W, all of which are manufactured by Norit Japan Co., Ltd.; GW, GWH, GLC, 4GC, KW, PW and PK, all of which are manufactured by Kuraray Chemical Co., Ltd.; HC-30S, GL-30S, 4G-3S, PA and PC, all of which are manufactured by Tsurumicoal Co., Ltd.; P, W, CW, SG, SGP, S, GB, CA and K, all of which are manufactured by Futamura Chemical Co., Ltd.; Shirasagi KL, Shirasagi W2C, Shirasagi WH2C, Shirasagi W5C, Shirasagi WH5C, Shirasagi WH5X, Shirasagi XS7100H-3, Carboraffin, Shirasagi A, Shirasagi C and Shirasagi M, all of which are manufactured by Japan EnviroChemicals Ltd.; and Hokuetsu CL-K, Hokuetsu HS and Hokuetsu KS, all of which are manufactured by Ajinomoto Fine-Techno Co., Inc.

Among these activated carbons, coconut shell-based activated carbons and wood-based activated carbons are preferred since they are capable of efficiently removing impurities showing absorption in the ultraviolet region of 250 to 300 nm that are contained in succinic acid. Meanwhile, from the standpoint of efficiently removing a color component of succinic acid, activated carbons that are obtained by a method such as a gas activation method, a steam activation method or a chemical activation method using zinc chloride, phosphoric acid or the like are preferred. Thereamong, activated carbons that are obtained by a steam activation method or a chemical activation method using zinc chloride, phosphoric acid or the like are more preferred and activated carbons that are activated with a chemical agent such as zinc chloride or phosphoric acid are particularly preferred. The shape of the activated carbon to be used may take any of a powder form, a crushed form, a molded form and a fibrous form. In cases where the activated carbon is loaded into a column, from the standpoint of controlling the column pressure, the activated carbon is preferably in the form of particles or granules.

As a method of the activated carbon treatment, either a method in which a succinic acid-containing solution is mixed with an activated carbon in a batchwise manner and the resulting mixture is then separated by filtration or a method in which the solution is passed through a packed bed of an activated carbon can be employed. In cases where a batch system is used, the treatment time is usually not shorter than 5 minutes, preferably not shorter than 10 minutes, and on another front, usually not longer than 5 hours, preferably not longer than 2 hours. In cases where a packed bed system is used, the treatment time is, in terms of SV (space velocity), usually 0.1 $hr^{-1}$ to 20 $hr^{-1}$. The treatment temperature is usually 20° C. to 90° C. As described in the above, the type of impurities to be removed is different depending on the type of the activated carbon; therefore, as a method of removing the impurities, for example, a method in which a plural types of activated carbons are used in combination or a method in which an activated carbon treatment is performed in combination with the above-described crystallization treatment, the below-described hydrogenation treatment and/or the below-described ion-exchange column treatment can be employed.

Further, in cases where water is used as a solvent, a succinic acid solution derived from fermentation may contain a component insoluble to water. Inclusion of such an insoluble component causes a reduction in the efficiency of removing the above-described impurities by an activated carbon and the subsequent purification step; therefore, it is preferred that such an insoluble component be removed in advance. Removal of the insoluble component is preferably carried out by a method in which, in-between the step of deriving succinic acid from a generated salt of succinic acid by a fermentation method and the step of performing an activated carbon treatment, the insoluble component is removed from a succinic acid solution originated from fermentation by subjecting the solution to a known membrane permeation treatment. Alternatively, a method in which the permeability of a membrane permeation treatment is improved by allowing the insoluble component to be adsorbed under the coexistence of powder-form activated carbon or a method in which an appropriate powder-form activated carbon is used to adsorb and remove the insoluble component simultaneously with the above-described impurities can also be suitably employed.

Further, in the present invention, in cases where removal of impurities is carried out by performing a crystallization treatment and/or an activated carbon treatment in combination with a hydrogenation treatment, for example, but not particularly limited to, a process in which the step of crystallization and/or activated carbon treatment is carried out prior to the <Hydrogenation Treatment>

Succinic acid obtained by a microbial reaction usually contains an odor component. It is preferred that the amount of the odor component in the succinic acid be reduced.

As a method for removing an odor component, there are known, for example, a deodorization method which utilizes an adsorbent such as an activated carbon; a method in which an odor component is removed by washing with an organic solvent; a crystallization method; and an aeration method. For removal of an odor component, a hydrogenation treatment in the presence of a catalyst is particularly effective. Meanwhile, a succinic acid-containing solution derived from a biomass resource by fermentation or the like may contain a small amount of fumaric acid.

When a succinic acid-containing solution derived from a biomass resource by fermentation or the like is subjected to a hydrogenation treatment, not only the odor component contained in succinic acid can be easily removed, but also, in cases where the solution contains fumaric acid as described above, succinic acid is generated from fumaric acid and the yield of succinic acid can thus be improved at the same time; therefore, as a method for deodorizing succinic acid, such hydrogenation treatment method is an exceptional technique as compared to conventional methods. It is preferred that the purification process include the step of subjecting a succinic acid-containing solution derived from fermentation to a hydrogenation treatment in the presence of a catalyst.

The hydrogenation treatment may take either a batchwise reaction system or a continuous reaction system and can be performed in accordance with a conventionally known method. Specific examples of the hydrogenation treatment method include a method in which, after allowing a succinic acid-containing solution and a hydrogenation catalyst to coexist in a pressurized reactor and subjecting this mixture to a hydrogenation treatment with stirring by introducing a hydrogen gas thereto, the thus treated succinic acid-containing reaction solution is separated from the hydrogenation catalyst and recovered from the reactor; a method in which a hydrogenation treatment is performed using a fixed-bed multi-tubular reactor or a single-tubular reactor while circulating a succinic acid-containing solution and hydrogen gas from a lower section of the reactor and the thus treated succinic acid-containing reaction solution is then recovered; and a method in which a hydrogenation treatment is performed by introducing a hydrogen gas from a lower section of a reactor and circulating a succinic acid-containing solution from an upper section of the reactor and the thus treated succinic acid-containing reaction solution is then recovered.

As the hydrogenation catalyst, a known homogeneous or heterogeneous noble metal-containing hydrogenation catalyst can be employed. Specific examples of such hydrogenation catalyst include, but not particularly limited to, those hydrogenation catalysts containing a noble metal such as ruthenium, rhodium, palladium or platinum. Thereamong, hydrogenation catalysts containing palladium or platinum, particularly palladium, are preferred.

These hydrogenation catalysts may be used as-is in the form of a compound containing the above-described noble metal or may be used in a form in which a ligand such as organic phosphine is allowed to coexist; however, from the standpoint of the easiness of catalyst separation, a heterogeneous noble metal-containing catalyst is preferred.

Further, a hydrogenation treatment can be performed by using such a noble metal-containing compound in coexistence with a metal oxide such as silica, titania, zirconia or activated alumina, a complex metal oxide thereof or an activated carbon. This method is preferred because, not only an odor component contained in succinic acid derived from fermentation, but also color components and organic impurities can be simultaneously adsorbed and removed, so that efficient removal of impurities can be achieved. The same effects can be attained also by using a catalyst prepared by supporting the above-described noble metal on a carrier such as a metal oxide (e.g., silica, titania, zirconia or activated alumina), a complex metal oxide thereof or an activated carbon; therefore, a method in which such a supported catalyst is used can also be suitably employed. The amount of the noble metal to be supported is usually 0.1 to 10% by weight of the carrier. The carrier is not particularly restricted; however, it is preferably silica or an activated carbon, particularly preferably an activated carbon, since the amount of the metal eluting therefrom during the hydrogenation treatment is small.

Accordingly, in the present invention, the embodiment in which a hydrogenation treatment is performed with a hydrogenation catalyst prepared by supporting a noble metal on a carrier such as a metal oxide (e.g., silica, titania, zirconia or activated alumina), a complex metal oxide thereof or an activated carbon is included in the definition of an embodiment in which a hydrogenation treatment is performed with a hydrogenation catalyst in the presence of an adsorbent selected from the group consisting of metal oxides, silica and activated carbons.

As a solvent into which succinic acid derived from a biomass resource is incorporated at the time of the hydrogenation treatment, water; an organic acid such as acetic acid or propionic acid; an ester such as ethyl acetate; an alcohol such as methanol, ethanol, propanol, isopropanol, butanol, 2-ethyl-1-hexanol or isobutanol; an ether such as diethyl ether, di-n-butyl ether, diisopropyl ether, di-n-butyl ether, tetrahydrofuran or dioxane; a ketone such as acetone, methyl ethyl ketone or diethyl ketone; a nitrile such as acetonitrile; or a mixture of these solvents can be employed. Thereamong, water is most preferred. As water, for example, deionized water, distilled water, river water, well water or tap water is usually used. As required, a solution, which is obtained as a result of the step of crystallizing succinic acid from a succinic acid-containing reaction solution after hydrogenation reaction and the subsequent filtration, can also be repeatedly used. The solution may have any succinic acid concentration as long as it is not higher than the saturation solubility at the solution temperature.

The hydrogen gas to be used may be pure hydrogen; however, hydrogen diluted with an inert gas such as nitrogen, helium or argon can also be used. In consideration of the effect on the efficiency of the hydrogenation treatment, the concentration of carbon monoxide in the hydrogen gas is usually not higher than 10,000 ppm, preferably not higher than 2,000 ppm, more preferably not higher than 1,000 ppm.

As for the hydrogen pressure in the hydrogenation treatment, when it is excessively low, the reaction rate becomes slow, so that a long time is required to complete the reaction. Meanwhile, when the hydrogen pressure is excessively high, depending on the catalyst and reaction conditions, hydrides of succinic acid such as butanediol and tetrahydrofuran are generated as by-products. Therefore, the hydrogen pressure in the hydrogenation treatment is usually not lower than 0.1 MPa, and the upper limit thereof is usually not higher than 5 MPa, preferably not higher than 3 MPa, more preferably not higher than 1 MPa.

As for the temperature of the hydrogenation treatment, when it is excessively low, the reaction rate becomes slow, so that a long time is required to complete the reaction. Meanwhile, when the temperature is excessively high, hydrides of succinic acid are generated as by-products and the amount of by-products such as malic acid is increased when water is used as the solvent. Therefore, the temperature of the hydrogenation treatment is usually not lower than 30° C., preferably not lower than 50° C., and the upper limit thereof is usually not higher than 150° C., preferably not higher than 120° C.

<Ion-Exchange Column Treatment>

Further, in the present invention, in order to remove impurities contained in succinic acid, a purification operation such as an ion-exchange column treatment may also be performed in combination.

The term "ion-exchange column treatment" used herein refers to a process of removing an ion by treating the liquid to pass through a column loaded with an ion-exchange resin. The ion-exchange resin should be selected in accordance with the ions contained in the liquid to be treated and the required purity of succinic acid. For example, in order to remove an anion such as sulfate ion or chloride ion, an anion-exchange resin (OH-type) can be employed and, in order to remove a cation such as a metal ion or ammonium ion, a cation-exchange resin (H-type) can be employed. These ion-exchange resins may also be used in combination as required.

Ion-exchange resins are classified into strongly acidic cation-exchange resins, weakly acidic cation-exchange resins, strongly basic anion-exchange resins and weakly basic anion-exchange resins, based on the strength of the functional group as an acid or a base. Further, based on the form thereof, ion-exchange resins are also classified into gel-type and porous-type. In the present invention, the ion-exchange resin to be used is not particularly restricted. However, taking into consideration the ion exchange efficiency, it is preferred to use a strongly acidic cation-exchange resin having a higher strength as an acid and/or a strongly basic anion-exchange resin having a higher strength as a base. Moreover, since there is no particular reason that the ion-exchange resin has to be a porous-type, it is desired to use a more versatile and inexpensive gel-type ion-exchange resin. Specific examples of such cation-exchange resin include Diaion SK1B (H-type) and specific examples of such anion-exchange resin include Diaion SA10A.

The ion-exchange column treatment can be performed within the temperature range which is not lower than the temperature at which succinic acid is dissolved in the liquid to be treated but lower than the heat-resistant temperature of the ion-exchange resin. That is, in cases where a cation-exchange resin is used, the ion-exchange column treatment is usually performed at a temperature of 20 to 100° C., although this is variable depending on the concentration of succinic acid in the liquid to be treated. Meanwhile, since an anion-exchange resin has a lower heat resistance as compared to a cation-exchange resin, in cases where an anion-exchange resin is used, the ion-exchange column treatment is usually performed at a temperature of 10 to 80° C. From the standpoint of the treatment temperature, in cases where an anion-exchange column treatment is performed, it is desired that a step in which a column treatment can be performed at a low succinic acid concentration and a low temperature be adopted.

Further, the method of allowing a liquid to pass through a column for treatment is not particularly restricted. When the throughput rate is excessively high, the pressure loss before and after the column is increased and the ion exchange is not sufficiently performed, while when the throughput rate is needlessly slow, an unnecessarily large column is required. Therefore, the treatment is usually performed at a space velocity (SV) of 0.1 to 10 $hr^{-1}$ and a superficial velocity of 1 to 20 m/hr.

Usually, in a column treatment, the ion concentration is measured at the column outlet at all times or at regular intervals and, if ion leakage were detected at the column outlet, the ion-exchange resin is subjected to a regeneration treatment. Regeneration of the ion-exchange resin can be carried out in accordance with a conventional method by using an acid such as sulfuric acid or hydrochloric acid in the case of a cation-exchange resin or an alkali such as caustic soda in the case of an anion-exchange resin.

The organic acid such as succinic acid obtained by the production method of the present invention contains a small amount of the above-described impurities such as an aromatic carboxylic acid, and the organic acid has an average absorbance of preferably not higher than 0.05, more preferably not higher than 0.03, particularly preferably not higher than 0.01, in the ultraviolet region of 250 to 300 nm. When succinic acid having a high average absorbance is used as a starting material of a polyester, a markedly colored polymer is produced.

In the present invention, the term "absorbance" refers to a value which is obtained by measuring a 3.0%-by-weight aqueous succinic acid solution placed in a quartz cell of 1 cm in optical path length by using an ultraviolet-visible absorption spectrophotometer. The measurement of absorbance can be performed by using a commercially available ultraviolet-visible absorption spectrophotometer.

The term "absorbance (A)" used herein means an absorbance measured at an optical path length of 1 cm and it is calculated in accordance with the following definition.

$$A = \log 10(I_0/I)$$

(wherein, $I_0$ represents the intensity of incident light; and I represents the intensity of transmitted light.)

Further, the term "average absorbance in the ultraviolet region of 250 to 300 nm" means a value which is obtained by dividing the sum of absorbances measured at 1 nm intervals in the wavelength range of 250 to 300 nm by 51.

Average absorbance=(Sum of absorbances measured at 1 nm intervals in the wavelength region of 250 to 300 nm)/51

The concentration of protocatechuic acid is, with respect to the succinic acid obtained by the production method of the present invention, preferably not higher than 80 ppm, more preferably not higher than 30 ppm, still more preferably not higher than 15 ppm, yet still more preferably not higher than 10 ppm, further still more preferably not higher than 5 ppm, particularly preferably not higher than 3 ppm. When the concentration of protocatechuic acid is high, the coloration of the resulting polymer is increased. Further, in order to control the concentration of protocatechuic acid at a low level, an excessive purification treatment is required; however, its polymer coloration-improving effect is limited and not efficient.

The concentration of uvitonic acid is, with respect to the succinic acid obtained by the production method of the present invention, preferably not higher than 300 ppm, more preferably not higher than 150 ppm, still more preferably not higher than 100 ppm, yet still more preferably not higher than 30 ppm, particularly preferably not higher than 10 ppm. When the concentration of uvitonic acid is high, the coloration of the resulting polymer is increased. Further, in order to control the concentration of protocatechuic acid at a low level, an excessive purification treatment is required; however, its polymer coloration-improving effect is limited and not efficient.

Here, also in cases where an organic acid other than succinic acid is produced, the concentration of protocatechuic acid is, with respect to the organic acid of interest obtained by the production method of the present invention, preferably not higher than 80 ppm, more preferably not higher than 30 ppm, still more preferably not higher than 15 ppm, yet still more preferably not higher than 10 ppm, further still more preferably not higher than 5 ppm, particularly preferably not higher than 3 ppm. Moreover, the concentration of uvitonic acid is, with respect to the organic acid of interest obtained by the production method of the present invention, preferably not higher than 300 ppm, more preferably not higher than 150 ppm, still more preferably not higher than 100 ppm, yet still more preferably not higher than 30 ppm, particularly preferably not higher than 10 ppm.

Further, it is usually preferred that the succinic acid produced in the present invention have a low absorbance in the visible light region and a low level of coloration. As for the yellowness (Y.I. value) of the succinic acid, the upper limit thereof is usually not higher than 50, preferably not higher than 30, more preferably not higher than 20, still more preferably not higher than 10, yet still more preferably not higher than 6, particularly preferably not higher than 4, while the lower limit thereof is, though not particularly restricted, usually not lower than −10, preferably not lower than −5, more preferably not lower than −1. When succinic acid showing a high Y.I. value is used as a starting material of a polymer, there is a drawback that a markedly colored polymer is produced. Meanwhile, succinic acid showing a low Y.I. value is a more preferred mode; however, from the economical standpoint, such succinic acid has disadvantages in that, for example, the production thereof requires a huge investment to be made in equipments and is considerably time-consuming. In the present invention, the Y.I. value is measured by the method according to JIS K7105.

The organic acid such as succinic acid obtained by the production method of the present invention may contain, as an impurity, elemental nitrogen which is originated from a biomass resource or generated by a fermentation treatment or a purification treatment including a step of performing neutralization with an acid. More specifically, the organic acid obtained by the production method of the present invention may contain elemental nitrogen originated from an amino acid, a protein, an ammonium salt, urea, a fermentative bacterium or the like.

The upper limit of the nitrogen atom content in the organic acid such as succinic acid obtained by the production method of the present invention is, in terms of the amount of atoms, usually not higher than 2,000 ppm, preferably not higher than 1,000 ppm, more preferably not higher than 100 ppm, most preferably not higher than 20 ppm. The lower limit of the nitrogen atom content is usually not less than 0.01 ppm, preferably not less than 0.05 ppm, and from the standpoint of economical efficiency of the purification step, more preferably not less than 0.1 ppm, still more preferably not less than 1 ppm.

The nitrogen atom content is measured by a known method such as an elemental analysis method or a method in which, after separating an amino acid or ammonia from a sample under a biological amino acid separation condition using an amino acid analyzer, the thus separated amino acid or ammonia is subjected to ninhydrin coloration and then detected.

In cases where succinic acid having a nitrogen atom content in the above-described range is used as a starting material of a polyester, the coloration of the resulting polyester is reduced, which is advantageous. In addition, the use of such succinic acid also has an effect of inhibiting a delay in the polymerization reaction of polyester.

Further, the organic acid such as succinic acid obtained by the production method of the present invention may also contain a sulfur atom generated by, for example, a purification treatment which includes a step of performing neutralization with an acid. Specific examples of impurities containing a sulfur atom include sulfuric acid, sulfates, sulfurous acid, organic sulfonic acids and organic sulfonates.

The sulfur atom content in the organic acid such as succinic acid obtained by the production method of the present invention is not particularly restricted; however, when it is excessively high, the use of the organic acid as a starting material of a polyester tends to cause, for example a delay in the polymerization reaction, partial gelation of the generated polymer and a reduction in the stability of the generated polymer. On the other hand, an excessively low sulfur atom content makes the purification step complicated. Therefore, the upper limit of the sulfur atom content in a dicarboxylic acid is, in terms of the amount of atoms, usually not higher than 100 ppm, preferably not higher than 20 ppm, more preferably not higher than 10 ppm, particularly preferably not higher than 5 ppm, most preferably not higher than 0.5 ppm. Meanwhile, the lower limit of the sulfur atom content is usually not less than 0.001 ppm, preferably not less than 0.01 ppm, more preferably not less than 0.05 ppm, particularly preferably not less than 0.1 ppm. Here, the sulfur atom content is measured by a known elemental analysis method.

The organic acid such as succinic acid obtained by the production method of the present invention may contain an alkali metal element. When the alkali metal content in an aliphatic dicarboxylic acid is excessively high, the use thereof as a starting material of a polymer not only reduces the thermal stability and hydrolysis resistance, but also causes a severe inhibition of polymerization during polymerization, so that a polymer of a high polymerization degree which has practically sufficient mechanical characteristics may not be obtained. Therefore, the alkali metal content is usually not higher than 50 ppm, preferably not higher than 30 ppm, more preferably not higher than 10 ppm, particularly preferably not higher than 5 ppm.

<Method of Producing Polymer>

Further, in the present invention, after producing an organic acid such as succinic acid in accordance with the above-described method, by performing a polymerization reaction using the thus obtained organic acid as a starting material, an organic acid-containing polymer can be produced. In recent years, with an increasing number of environment-friendly industrial products, polymers prepared from a material of plant origin have been drawing attention. Particularly, the succinic acid produced in the present invention can be processed into known polymers that are produced by using a dicarboxylic acid component, preferably an aliphatic dicarboxylic acid as a starting material, such as polyesters, polyamides and polyurethanes. Specific examples of succinic acid unit-containing polymers include polyesters that are obtained by polymerization between a diol such as butanediol or ethylene glycol and succinic acid; and polyamides that are obtained by polymerization between a diamine such as hexamethylenediamine and succinic acid.

As one example of the method of producing a polymer, a method of producing a polyester will now be described.

<Method of Producing Polyester>

In the present invention, as a method of producing a polyester, a conventionally known method can be employed. For example, a polyester can be produced by a commonly used melt-polymerization method in which an esterification reaction and/or a transesterification reaction is carried out between an aliphatic dicarboxylic acid component containing the above-described succinic acid and a diol component and the resultant is then subjected to a polycondensation reaction under reduced pressure or by a known solution-heating dehydration condensation method in which an organic solvent is used; however, from the standpoint of economical efficiency and simplicity of the production process, a method in which a polyester is produced by melt polymerization in the absence of solvent.

<Dicarboxylic Acid Component>

The dicarboxylic acid component is not particularly restricted as long as it contains the succinic acid obtained by the above-described method of producing an organic acid. The dicarboxylic acid component may contain an aliphatic and/or aromatic dicarboxylic acid derived from a fossil resource; however, it is preferred that the dicarboxylic acid component contain the succinic acid obtained by the above-described method of producing an organic acid.

<Diol Component>

The diol component is not particularly restricted; however, it is preferably an aliphatic diol.

The aliphatic diol is not particularly restricted as long as it is an aliphatic or alicyclic compound having two OH groups, and examples thereof include aliphatic diols in which the lower limit of the number of carbon atoms is not less than 2 and the upper limit is usually not more than 10, preferably not more than 6.

Specific examples of such aliphatic diol include ethylene glycol, 1,3-propylene glycol, neopentylglycol, 1,6-hexamethylene glycol, decamethylene glycol, 1,4-butanediol and 1,4-cyclohexanedimethanol. These aliphatic diols may be used individually, or two or more thereof may be used in combination as a mixture.

Thereamong, ethylene glycol, 1,4-butanediol, 1,3-propylene glycol and 1,4-cyclohexanedimethanol are preferred and ethylene glycol, 1,4-butanediol and a mixture thereof are more preferred. Further, an aliphatic diol containing 1,4-butanediol as a main component or 1,4-butanediol is particularly preferred. The term "main component" means that the amount of the component is, with respect to the total amount of diol units, usually not less than 50 mol %, preferably not less than 60 mol %, more preferably not less than 70 mol %, particularly preferably not less than 90 mol %.

Further, a polyether terminated with a hydroxy group at both ends may also be used in combination with the above-described aliphatic diol. In the polyether terminated with a hydroxy group at both ends, the lower limit of the number of carbon atoms is usually not less than 4, preferably not less than 10, and the upper limit is usually not more than 1,000, preferably not more than 200, more preferably not more than 100.

Specific examples of such polyether terminated with a hydroxy group at both ends include diethylene glycol, triethylene glycol, polyethylene glycol, polypropylene glycol, polytetramethylene glycol, poly-1,3-propanediol and poly-1,6-hexamethylene glycol. Further, for example, a copolymer polyester composed of polyethylene glycol and polypropylene glycol can also be used. The amount of the polyether terminated with a hydroxy group at both ends to be used is, in terms of the content in the resulting polyester, a calculated amount of usually not more than 90% by weight, preferably not more than 50% by weight, more preferably not more than 30% by weight.

<Other Copolymer Component>

In the production of a polyester according to the present invention, in addition to the above-described diol component and dicarboxylic acid component, a copolymer component may be added as well.

Specific examples of the copolymer component include at least one polyfunctional compound selected from the group consisting of bifunctional oxycarboxylic acids, unsaturated dicarboxylic acids, tri- or higher functional polyhydric alcohols for forming a cross-linked structure, tri- or higher functional polycarboxylic acids or anhydrides thereof and tri- or higher functional oxycarboxylic acids. When these copolymer components are added, an effect of considerably improving the polymerization rate in the polyester production is exerted. Among these copolymer components, an oxycarboxylic acid is suitably employed since it tends to allow a polyester having a high polymerization degree to be easily produced.

Specific examples of the bifunctional oxycarboxylic acids include lactic acid, glycolic acid, hydroxybutyric acid, hydroxycaproic acid, 2-hydroxy-3,3-dimethylbutyric acid, 2-hydroxy-3-methylbutyric acid and 2-hydroxyisocaproic acid, and these may also be in the form of an ester or lactone of an oxycarboxylic acid or a derivative of an oxycarboxylic acid polymer or the like. Further, these oxycarboxylic acids may be used individually, or two or more thereof may be used in combination as a mixture. In cases where these oxycarboxylic acids have optical isomers, they may also be any of a D-isomer, an L-isomer and a racemic body. Moreover, these oxycarboxylic acids may be in the form of a solid, a liquid or an aqueous solution. Thereamong, readily available lactic acid and glycolic acid are particularly preferred. As for the form thereof, a 30 to 95% aqueous solution is preferred since such an aqueous solution is readily available. In this case, the lower limit of the amount of the oxycarboxylic acid to be used is, with respect to the amount of the material monomer, usually not less than 0.02 mol %, preferably not less than 0.5 mol %, more preferably not less than 1.0 mol %, while the upper limit thereof is usually not more than 30 mol %, preferably not more than 20 mol %, more preferably not more than 10 mol %.

Examples of the unsaturated dicarboxylic acids include itaconic acid, aconitic acid, fumaric acid and maleic acid. These unsaturated dicarboxylic acids may be used individually, or two or more thereof may be used in combination as a mixture. Since an unsaturated dicarboxylic acid causes generation of a gel, the amount of the unsaturated dicarboxylic acid to be used is, with respect to the total amount of monomer units constituting the polyester, usually not more than 5 mol %, preferably not more than 0.5 mol %, more preferably not more than 0.05 mol %.

Specific examples of the tri- or higher functional polyhydric alcohols include glycerin, trimethylolpropane and pentaerythritol. These tri- or higher functional polyhydric alcohols may be used individually, or two or more thereof may be used in combination as a mixture.

Specific examples of the tri- or higher functional polycarboxylic acids or anhydrides thereof include propanetricarboxylic acids, pyromellitic acid anhydrides, benzophenonetetracarboxylic acid anhydrides and cyclopentatetracarboxylic acid anhydrides, and these may be used individually, or two or more thereof may be used in combination as a mixture.

Specific examples of the tri- or higher functional oxycarboxylic acids include malic acid, hydroxyglutaric acid, hydroxymethylglutaric acid, tartaric acid, citric acid, hydroxyisophthalic acid and hydroxyterephthalic acid. These tri- or higher functional oxycarboxylic acids may be used individually, or two or more thereof may be used in combination as a mixture. In particular, from the standpoint of availability, malic acid, tartaric acid and citric acid are preferred.

Since the above-described tri- or higher functional compounds cause generation of a gel, the amount thereof to be used is, with respect to the total amount of monomer units constituting the polyester, usually not more than 5 mol %, preferably not more than 0.5 mol %, more preferably not more than 0.2 mol %.

For the conditions of temperature, time, pressure and the like, conventionally known ranges can be adopted.

With regard to the temperature of the esterification reaction and/or the transesterification reaction performed between a succinic acid-containing aliphatic dicarboxylic acid component and a diol component, the lower limit is usually not lower than 150° C., preferably not lower than 180° C., and the upper limit is usually not higher than 260° C., preferably not higher than 250° C. As for the reaction atmosphere, these reactions are usually performed under an inert gas atmosphere such as nitrogen or argon. The reaction pressure is usually in normal pressure to 10 kPa, preferably normal pressure.

The reaction time is usually not shorter than 1 hour and the upper limit thereof is usually not longer than 10 hours, preferably not longer than 4 hours.

In the subsequent polycondensation reaction, when the pressure at the time of producing a polyester by polymerization is excessively high, the time required for the production is extended and, as a result, a reduction in the molecular weight and coloration of the resulting polyester are caused by thermal decomposition, so that it tends to become difficult to produce a polyester which exhibits practically sufficient characteristics. Meanwhile, from the standpoint of improving the polymerization rate, a method in which a polyester is produced by using an ultra-high vacuum polymerization equipment is a preferred embodiment; however, not only a huge investment needs to be made into equipments, but also the time required for a polyester to be produced by polymerization still tends to be long; therefore, there are concerns for a reduction in the molecular weight and coloration of the resulting polyester that are caused by thermal decomposition. Accordingly, the polycondensation reaction is performed at a vacuum degree of, as the lower limit, usually not lower than $0.01 \times 10^3$ Pa, preferably not lower than $0.01 \times 10^3$ Pa and, as the upper limit, usually not higher than $1.4 \times 10^3$ Pa, preferably not higher than $0.4 \times 10^3$ Pa.

As for the reaction temperature, when it is excessively low, the rate of polymerization reaction becomes extremely slow, so that not only the time required for the production of a polyester having a high polymerization degree is extended, but also a high-power stirring machine becomes necessary; therefore, the use of such a low reaction temperature is economically disadvantageous. Meanwhile, when the reaction temperature is excessively high, although the polymerization rate is improved, thermal decomposition of the polymer is also induced during the production, making it difficult to produce a polyester having a high polymerization degree. Accordingly, the lower limit of the reaction temperature is usually not lower than 150° C., preferably not lower than 180° C., while the upper limit thereof is usually not higher than 280° C., preferably not higher than 260° C.

As for the reaction time, when it is excessively short, the reaction proceeds insufficiently to yield a polyester having a low polymerization degree. The resulting polyester exhibits a low tensile elongation at break and has a large amount of terminal carboxyl group, which often causes considerable deterioration in the tensile elongation at break. Meanwhile, when the reaction time is excessively long, since the molecular weight of the resulting polyester is markedly reduced due to thermal decomposition, not only the tensile elongation at break may be impaired, but also the amount of terminal carboxyl group, which affects the durability of polymer, may be increased due to thermal decomposition. Accordingly, the lower limit of the reaction time is usually not shorter than 2 hours, while the upper limit thereof is usually not longer than 15 hours, preferably not longer than 8 hours, more preferably not longer than 6 hours.

In the present invention, with regard to the molar ratio of the diol component and the aliphatic dicarboxylic acid component required for obtaining a polyester having a desired polymerization degree, the preferred range thereof is variable depending on the purpose thereof and the types of the starting materials; however, the lower limit of the amount of the diol component is, per 1 mol of acid component, usually not less than 0.8 mol, preferably not less than 0.9 mol, while the upper limit thereof is usually not more than 3.0 mol, preferably not more than 2.7 mol, particularly preferably not more than 2.5 mol.

Further, in the present invention, it is preferred that the polycondensation reaction be carried out in the presence of a polymerization catalyst. The timing of adding the polymerization catalyst is not particularly restricted as long as it is before the polycondensation reaction. The polymerization catalyst may be added at the time of feeding the starting materials or at the start of pressure reduction.

Examples of the polymerization catalyst generally include those compounds other than hydrogen and carbon that contain a metal element belonging to the Groups 1 to 14 in the periodic table. Specific examples thereof include organic group-containing compounds such as carboxylates, alkoxy salts, organic sulfonates and β-diketonates, which contain at least one metal selected from the group consisting of titanium, zirconium, tin, antimony, cerium, germanium, zinc, cobalt, manganese, iron, aluminum, magnesium, calcium, strontium, sodium and potassium; inorganic compounds such as oxides and halides of the above-described metals; and mixtures of these compounds. Because of the above-described reason, these catalyst components may be contained in the polyester starting material derived from a biomass resource. In this a case, the starting material does not have to be particularly purified and may be used as-is in the form of a starting material containing a metal. However, depending on the polyester to be produced, there are cases where the lower is the content of a metal atom of the Group 1 such as sodium or potassium in the polyester starting material, the easier is it to produce a polyester having a high polymerization degree. In such a case, a starting material which is purified to such an extent that it does not substantially contain a metal element of the Group 1 is suitably employed.

Among the above-described polymerization catalysts, metal compounds containing titanium, zirconium, germanium, zinc, aluminum, magnesium or calcium and mixtures of these metal compounds are preferred. Thereamong, titanium compounds, zirconium compounds and germanium compounds are particularly preferred. Further, the catalyst is preferably in the form of a liquid or a compound soluble to an ester low polymer or polyester at the time of polymerization because the polymerization rate is increased when the catalyst is in a molten or dissolved state at the time of polymerization.

As the titanium compound, tetraalkyl titanate is preferred, and specific examples thereof include tetra-n-propyl titanate, tetraisopropyl titanate, tetra-n-butyl titanate, tetra-t-butyl titanate, tetraphenyl titanate, tetracyclohexyl titanate, tetrabenzyl titanate and mixed titanates thereof. In addition, titanium (oxy)acetylacetonate, titanium tetraacetylacetonate, titanium (diisopropoxide)acetylacetonate, titanium bis(ammonium lactate)dihydroxide, titanium bis(ethylacetoacetate) diisopropoxide, titanium (triethanolaminate)isopropoxide, polyhydroxytitanium stearate, titanium lactate, titanium triethanolaminate, butyl titanate dimer and the like can be suitably used as well. Moreover, titanium oxide and complex oxides containing titanium and silicon can also be suitably used.

Among these titanium compounds, tetra-n-propyl titanate, tetraisopropyl titanate, tetra-n-butyl titanate, titanium(oxy)acetylacetonate, titanium tetraacetylacetonate, titanium bis(ammonium lactate)dihydroxide, polyhydroxytitanium stearate, titanium lactate, butyl titanate dimer, titanium oxide and titania/silica complex oxides are preferred, and tetra-n-butyl titanate, titanium (oxy)acetylacetonate, titanium tetraacetylacetonate, polyhydroxytitanium stearate, titanium lactate, butyl titanate dimer and titania/silica complex oxides are more preferred. Further, tetra-n-butyl titanate, polyhydroxytitanium stearate, titanium (oxy)acetylacetonate, titanium tetraacetylacetonate and titania/silica complex oxides are particularly preferred.

Specific examples of the zirconium compounds include zirconium tetraacetate, zirconium acetate hydroxide, zirconium tris(butoxy)stearate, zirconyl diacetate, zirconium oxalate, zirconyl oxalate, zirconium potassium oxalate, polyhydroxyzirconium stearate, zirconium ethoxide, zirconium tetra-n-propoxide, zirconium tetraisopropoxide, zirconium tetra-n-butoxide, zirconium tetra-t-butoxide, zirconium tributoxyacetylacetonate and mixtures thereof. Further, zirconium oxide and complex oxides containing zirconium and silicon can also be suitably used.

Among these zirconium compounds, zirconyl diacetate, zirconium tris(butoxy)stearate, zirconium tetraacetate, zirconium acetate hydroxide, zirconium ammonium oxalate, zirconium potassium oxalate, polyhydroxyzirconium stearate, zirconium tetra-n-propoxide, zirconium tetraisopropoxide, zirconium tetra-n-butoxide and zirconium tetra-t-butoxide are preferred, and zirconyl diacetate, zirconium tetraacetate, zirconium acetate hydroxide, zirconium tris(butoxy)stearate, zirconium ammonium oxalate, zirconium tetra-n-propoxide and zirconium tetra-n-butoxide are more preferred. Further, zirconium tris(butoxy)stearate is particularly preferred since it allows a colorless polyester having a high polymerization degree to be easily obtained.

Specific examples of the germanium compounds include inorganic germanium compounds such as germanium oxide and germanium chloride; and organic germanium compounds such as tetraalkoxygermanium. From the standpoints of price, availability and the like, for example, germanium oxide, tetraethoxygermanium and tetrabutoxygermanium are preferred, and germanium oxide is particularly preferred.

In cases where a metal compound is used as the polymerization catalyst, when the amount of the catalyst is excessively large, not only is it economically disadvantageous, but also the thermal stability of the resulting polymer is reduced. On the other hand, when the amount of the catalyst is excessively small, the polymerization activity is decreased, so that the polymer becomes more likely to be decomposed during the production. Accordingly, the lower limit of the amount of the catalyst to be used is, in terms of the amount of the metal with respect to that of the resulting polyester, usually not less than 5 ppm, preferably not less than 10 ppm, while the upper limit thereof is usually not more than 30,000 ppm, preferably not more than 1,000 ppm, more preferably not more than 250 ppm, particularly preferably not more than 130 ppm.

<Polyester and Use Thereof>

A polyester produced by the method of the present invention is generally characterized in that the amount of terminal carboxylic acid, which markedly deteriorates the thermal stability of a polymer, is small; therefore, the polyester has characteristic features that it has excellent thermal stability and a reduction in the quality at the time of molding is thus small, that is, occurrence of side reactions such as breakage of the terminal group and main chain is limited at the time of melt molding. Accordingly, in a preferred polyester produced in the present invention, the number of terminal COOH groups is, although it varies depending on the polymerization degree of the polyester, usually not more than 100 equivalents/ton (hereinafter, may be abbreviated as "eq/ton"), preferably not more than 60 eq/ton, more preferably not more than 40 eq/ton, particularly preferably not more than 30 eq/ton. Meanwhile, when the amount of terminal carboxyl group is excessively small, the polymerization rate becomes extremely slow, so that a polymer having a high-polymerization degree cannot be produced. For this reason, the lower limit of the number of terminal COOH groups in the polyester is usually not less than 0.1 eq/ton, more preferably not less than 1 eq/ton.

It is usually preferred that the polyester produced in the present invention be one having limited coloration. The upper limit of the yellowness (Y.I. value) of the polyester is usually not higher than 50, preferably not higher than 30, more preferably not higher than 20, still more preferably not higher than 15, particularly preferably not higher than 10. Meanwhile, the lower limit thereof is not particularly restricted; however, it is usually not lower than −20, preferably not lower than −10, more preferably not lower than −5, particularly preferably not lower than −3, most preferably not lower than −1. A polyester showing a high Y.I. value has a drawback in that the use of a film, a sheet or the like thereof is restricted. Meanwhile, a polyester showing a low Y.I. value is a more preferred embodiment; however, it is economically disadvantageous in that, for example, the production of such a polymer requires complex production processes as well as an extremely large investment in the equipments. In the present invention, the Y.I. value is measured by the method according to JIS K7105.

In the polyester produced in the present invention, from the standpoint of attaining practically sufficient mechanical characteristics, the reduced viscosity ($\eta sp/C$) value is not less than 0.5, more preferably not less than 1.6, still more preferably not less than 2.0, particularly preferably not less than 2.3. From the standpoint of operability such as the easiness of recovering the resulting polyester after the polymerization reaction and the moldability thereof, the upper limit of the reduced viscosity ($\eta sp/C$) value is usually not higher than 6.0, preferably not higher than 5.0, still more preferably not higher than 4.0.

In the present invention, the reduced viscosity is measured under the following measurement conditions.

[Conditions for Measuring Reduced Viscosity ($\eta sp/C$)]

Viscosity tube: Ubbelohde's viscosity tube
Measuring temperature: 30° C.
Solvent: phenol/tetrachloroethane (1:1 weight ratio) solution
Polyester concentration: 0.5 g/dl In the method of producing a polyester according to the present invention, a variety of additives, such as a heat stabilizer, an antioxidant, a nucleating agent, a flame retardant, an antistatic agent, a mold releasing agent and/or an ultraviolet absorber, may also be added to the reaction system at the time of performing polymerization or to the resulting polyester in such a range which does not adversely affect the properties of the polyester.

Further, in addition to the above-described various additives, at the time of molding, a reinforcing agent and a filler, such as a glass fiber, a carbon fiber, a titanium whisker, mica, talc, $CaCO_3$, $TiO_2$ and silica, may also be added to perform molding.

The polyester obtained by the production method of the present invention has excellent heat resistance and color tone as well as excellent hydrolysis resistance and biodegradability and can be produced inexpensively; therefore, it is suitably used in a variety of film applications and applications of injection-molded articles.

A molded article can be produced by molding the polyester obtained by the production method of the present invention. As a molding method, any conventional method can be employed. Examples of the molded article which can be obtained are shown below along with the applications thereof. Specific examples of the application include injection-molded articles (e.g., trays used for fresh foods, containers of fast foods and outdoor leisure products), extrusion-molded articles (e.g., films, sheets, fishing lines, fishing nets, vegetation nets and water-holding sheets) and blow-molded articles (e.g., bottles). In addition, the polyester can also be utilized in, for example, agricultural films, coating materials, fertilizer coating materials, laminated films, plates, stretched sheets, monofilaments, multifilaments, nonwoven fabrics, flat yarns, staples, crimped fibers, striated tapes, split yarns, composite fibers, blow bottles, foamed articles, shopping bags, trash bags, compost bags, cosmetic containers, detergent containers, bleach containers, ropes, tying materials, surgical sutures, sanitary cover stock materials, cooler boxes, cushioning films and synthetic papers.

EXAMPLES

The present invention will now be described in more detail by way of examples thereof; however, the present invention is not restricted thereto.
<Method of Quantifying Organic Acid>
The amount of organic acid was measured by quantitative analysis using HPLC under the following conditions.
Column: Ultron PS-80H (8.0 mm I.D.×300 mm), manufactured by Shinwa Chemical Industries Ltd.
Eluent: water (perchloric acid) (60% aqueous perchloric acid solution, 1.8 ml/1 L-$H_2O$)
Temperature: 60° C.
Detection: RI, UV (210 nm)
<Method of Quantifying Ammonium Ion>
The amount of ammonium ion was measured by quantitative analysis using ion chromatography under the following conditions.
Column: GL-IC-C75 (4.6 mm I.D.×150 mm)
Eluent: 3.5 mmol/L sulfuric acid
Column temperature: 40° C.
<Method of Quantifying Aromatic Carboxylic Acid>
In Experimental Examples 1 to 3, the amount of aromatic carboxylic acid was measured by quantitative analysis using HPLC under the following conditions. In Example 2 and Comparative Example 2, the measurement was carried out under the same conditions as in the above-described method of quantifying organic acid.

Column: Develosil C30-UG (3 μm, 4.6 mm I.D.×100 mm), manufactured by Nomura Chemical Co., Ltd.
Eluent: 0.02% aqueous formic acid solution, 1.0 mL/min
Temperature: 40° C.
Detector: UV (280 nm)
<Polymer Evaluation Method>
Yellow Index (Hereinafter, May be Abbreviated as "Y.I.")
In accordance with the method prescribed in JIS K7105, a chip of the obtained polymer was placed in a cell and the Y.I. thereof was measured 4 times by a reflection method using Color Meter ZE-6000 (manufactured by Nippon Denshoku Industries Co., Ltd.). The average value thereof was used as the Y.I. value of the polymer.
Reduced Viscosity
The obtained polyester was dissolved in phenol/tetrachloroethane (1/1 (mass ratio) mixture) to a concentration of 0.5 g/dl. Then, in a 30° C. thermostat bath of the resulting solution, the time (t: seconds) required for a viscosity tube to fall was measured. Further, the time required for the viscosity tube to fall in the bath of the solvent alone ($t_0$: seconds) was measured to calculate the reduced viscosity at 30° C. ($\eta_{sp}/C = (t-t_0)/t_0 \cdot C$; C represents the concentration of the solution).
Amount of Terminal Carboxyl Group
The obtained polyester was dissolved in benzyl alcohol and the resulting solution was titrated with 0.1N NaOH to determine the amount of terminal carboxyl group as an equivalent amount of terminal acid group per $1 \times 10^6$ g of the polyester.

Example 1

Preparation of *Brevibacterium flavum* MJ233/ΔQsuB/PC-4/ΔLDH] (Preparation of QsuB-Disrupted Strain)

(A) Extraction of Genomic DNA from MJ233 Strain
In 10 mL of a seed culture medium [2 g of urea, 7 g of $(NH_4)_2SO_4$, 0.5 g of $KH_2PO_4$, 0.5 g of $K_2HPO_4$, 0.5 g of $MgSO_4 \cdot 7H_2O$, 6 mg of $FeSO_4 \cdot 7H_2O$, 6 mg of $MnSO_4 \cdot 4$-$5H_2O$, 200 μg of biotin, 100 μg of thiamine, 1 g of yeast extract, 1 g of casamino acid and 20 g of glucose; dissolved in 1 L of distilled water], the *Brevibacterium flavum* MJ-233 strain was cultured until the late stage of logarithmic growth phase, and the resulting bacterial cells were collected by centrifugation (10,000 g, 5 minutes). The thus obtained bacterial cells were suspended in 0.15 mL of a 10 mM NaCl/20 mM Tris buffer (pH 8.0)/1 mM EDTA.2Na solution containing lysozyme at a concentration of 10 mg/mL. Then, proteinase K was added to the thus obtained suspension to a final concentration of 100 μg/mL and the resultant was incubated at 37° C. for 1 hour. Thereafter, sodium dodecyl sulfate was further added to a final concentration of 0.5% and the resultant was incubated at 50° C. for 6 hours to perform bacteriolysis. To the resulting lysate, an equivalent amount of a phenol/chloroform solution was added. After gently shaking the resultant at room temperature for 10 minutes, the whole amount thereof was centrifuged (5,000 G, 20 minutes, 10 to 12° C.) and a supernatant fraction was recovered. Then, after adding sodium acetate to the thus recovered fraction to a concentration of 0.3 M, a double amount of ethanol was further added and the resultant was mixed. The resulting mixture was centrifuged (15,000 G, 2 minutes) to recover precipitates, which were then washed with 70% ethanol and air-dried. To the thus obtained DNA, 5 mL of a 10 mM Tris buffer (pH 7.5)/1 mM EDTA.2Na solution was added, and the resultant was left to stand at 4° C. overnight and then used as a template DNA in the later PCR.

(B) Construction of Plasmid for Disruption of QsuB Gene

Figure 3:
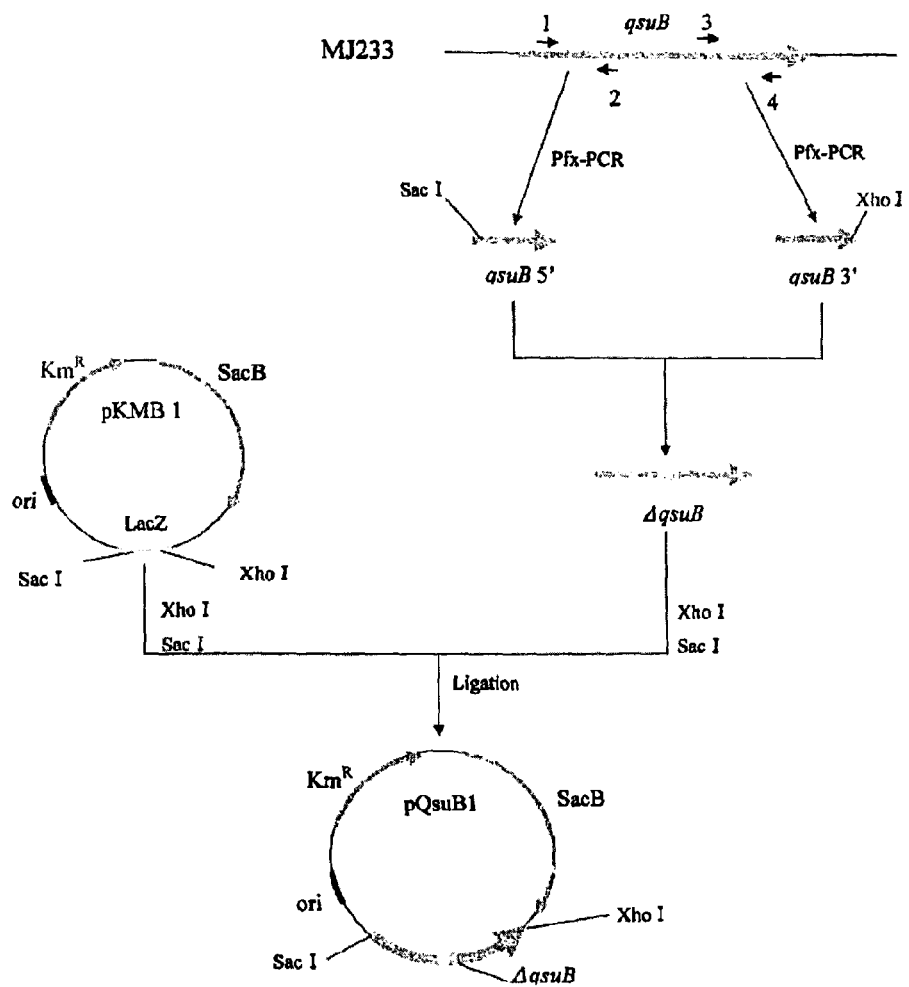
FIG. 3 is a diagram illustrating the procedures for constructing a plasmid pQsuB1.

A DNA fragment of the qsuB gene originated from the *Brevibacterium flavum* MJ233 strain in which an internal sequence thereof was deleted was obtained by performing crossover PCR using the DNA prepared in the above-described (A) as a template and synthetic DNAs (SEQ ID NOs: 1, 2, 3 and 4) which were designed based on a sequence of the vicinity of the qsuB gene of the *Corynebacterium glutamicum* ATCC13032 strain whose entire genomic sequence has been reported (GenBank Accession No. BA000036). PCR of the DNA fragment containing the 5'-end region of the qsuB gene was performed using the synthetic DNAs shown in SEQ ID NOs:1 and 2 as primers, while PCR of the DNA fragment containing the 3'-end region of the qsuB gene was performed using the synthetic DNAs shown in SEQ ID NOs:3 and 4 as primers. The composition of the reaction solution was as follows: 1 μL of the template DNA, 0.5 μL of PfxDNA polymerase (manufactured by Invitrogen Corporation), 1-fold concentration of the attached buffer, 0.4 μM of each primer, 1 mM MgSO$_4$ and 0.2 μM dNTPs were mixed and the total volume was adjusted to 50 μL. The reaction temperature conditions were as follows: a DNA thermal cycler (PTC-200, manufactured by MJ Research Inc.) was used and a cycle of 94° C. for 15 seconds, 55° C. for 30 seconds and 68° C. for 45 seconds was repeated 35 times. It is noted here, however, that the reaction solution was retained at 94° C. for 2 minutes in the first cycle and at 68° C. for 3 minutes in the final cycle. Then, PCR was further carried out using the resulting two amplification products as templates and the synthetic DNAs shown in SEQ ID NOs:1 and 4 as primers. Here, the composition of the reaction solution was as follows: 1 μL of the template DNAs, 0.5 μL of PfxDNA polymerase (manufactured by Invitrogen Corporation), 1-fold concentration of the attached buffer, 0.4 μM of each primer, 1 mM MgSO$_4$ and 0.2 μM dNTPs were mixed and the total volume was adjusted to 50 μL. The reaction temperature conditions were as follows: a DNA thermal cycler (PTC-200, manufactured by MJ Research Inc.) was used and a cycle of 94° C. for 15 seconds, 55° C. for 30 seconds and 68° C. for 1 minute and 20 seconds was repeated 35 times. It is noted here, however, that the reaction solution was retained at 94° C. for 2 minutes in the first cycle and at 68° C. for 3 minutes in the final cycle. The thus obtained DNA fragment in which the internal sequence of the qsuB gene was deleted was purified using ChargeSwitch PCR Clean-Up Kit (manufactured by Invitrogen Corporation) and then digested with restriction enzymes XhoI and SacI. After separating the resulting DNA fragment of about 1.2 kb by 0.9% agarose gel electrophoresis (SeaKem GTG agarose; manufactured by FMC BioProducts), the DNA fragment was detected by visualizing it with ethidium bromide staining and then recovered from the gel using Zymoclean Gel DNA Recovery Kit (manufactured by Zymo Research Corporation). The thus obtained DNA was mixed with a DNA prepared by digesting the plasmid pKMB1 (JP 2005-95169A) with restriction enzymes XhoI and SacI, and these DNAs were ligated with each other using Ligation Kit ver. 2 (manufactured by Takara Bio Inc.). Using the thus obtained plasmid DNA, *Escherichia coli* (DH5α strain) was transformed and then spread onto an LB agar medium containing 50 μg/mL of kanamycin and 50 μg/mL of X-Gal. A clone which formed a white colony on this medium was cultured in a liquid medium by a conventional method and a plasmid DNA was then purified. The thus obtained plasmid DNA was digested with restriction enzymes XhoI and SacI. As a result, an insert fragment of about 1.2 kb was detected and this was named "pQsuB1". The construction process of the pQsuB1 is shown in FIG. 3.

(C) Preparation of QsuB-Disrupted Strain

As a sample strain for preparing a QsuB-disrupted strain, the *Brevibacterium flavum* MJ233/PC-4/ΔLDH strain prepared in the later-described Reference Example 1 was employed. A plasmid DNA to be used for transformation of the *Brevibacterium flavum* MJ233/PC-4/ΔLDH strain was prepared from *Escherichia coli* JM110 strain which was transformed with the pQsuB1 plasmid constructed in the above-described (B). The transformation of the *Brevibacterium flavum* MJ233/PC-4/ΔLDH strain was carried out by an electric pulse method (Vertes A. A., Inui M., Kobayashi M., Kurusu Y. and Yukawa H., Res. Microbiol., 1993, vol. 144 (3), p 181-185), and the resulting transformant was spread onto an LBG agar medium containing 50 μg/mL of kanamycin [10 g of tryptone, 5 g of yeast extract, 5 g of NaCl, 20 g of glucose and 15 g of ager; dissolved in 1 L of distilled water]. In the strain that grew on this medium, since the pQsuB1 is a plasmid which cannot be replicated in the cells of the *Brevibacterium flavum* MJ233 strain, as a result of homologous recombination between the qsuB gene of the plasmid and the qsuB gene on the genome of the *Brevibacterium flavum* MJ-233 strain, a kanamycin-resistant gene originated from the plasmid is expected to have been inserted in the genome. Whether or not the kanamycin-resistant strain obtained in this manner carries such gene derived by homologous recombination between the qsuB gene existing on its genome and the qsuB gene existing on the plasmid pQsuB1 was verified by performing colony PCR using the synthetic DNAs shown in SEQ ID NOs:1 and 5 and SEQ ID NOs:4 and 6 as primers. The template DNA was prepared in the form of a supernatant which was obtained by suspending the formed colonies in 50 μL of sterilized water and boiling the resulting suspension for 5 minutes. The composition of the reaction solution was as follows: 1 μL of the template DNA, 0.2 μL of Ex-Taq DNA polymerase (manufactured by Takara Bio Inc.), 1-fold concentration of the attached buffer, 0.2 μM of each primer and 0.2 μM dNTPs were mixed and the total volume was adjusted to 20 μL. The reaction temperature conditions were as follows: a DNA thermal cycler (PTC-200, manufactured by MJ Research Inc.) was used and a cycle of 98° C. for 10 seconds, 55° C. for 20 seconds and 72° C. for 2 minutes was repeated 35 times. It is noted here, however, that the reaction solution was retained at 95° C. for 2 minutes in the first cycle and at 72° C. for 3 minutes in the final cycle. As a result of analyzing the kanamycin-resistant strain by the above-described method, a strain which yields a PCR amplification product of 1,256 bp with the combination of SEQ ID NOs:1 and 5 and a PCR amplification product of 1,866 bp with the combination of SEQ ID NOs:4 and 6 was selected, and this strain was named "*Brevibacterium flavum* MJ233/ΔQsuB/PC-4/ΔLDH".

(Evaluation of Growth of QsuB-Disrupted Strain on Synthetic Medium)

A MM medium [4 g of urea, 14 g of $(NH_4)_2SO_4$, 0.5 g of $KH_2PO_4$, 0.5 g of $K_2HPO_4$, 0.5 g of $MgSO_4.7H_2O$, 20 mg of $FeSO_4.7H_2O$, 20 mg of $MnSO_4.H_2O$, 200 μg of D-biotin and 200 μg of thiamine hydrochloride; dissolved in 1 L of distilled water] in an amount of 100 mL was placed in a 500-mL Erlenmeyer flask and heat-sterilized at 120° C. for 20 minutes. The medium was then cooled to room temperature and 6 mL of 50% aqueous glucose solution which had been sterilized in advance and 50 μL of filter-sterilized 5% aqueous kanamycin solution were added thereto. The *Brevibacterium flavum* MJ233/ΔQsuB/PC-4/ΔLDH strain was inoculated to the resulting medium to an absorbance (OD$_{660}$) of 1.0 and cultured at 30° C. with stirring at 160 rpm. At 1.5 hours, 3.1 hours, 5.0 hours, 7.0 hours, 9.0 hours, 11.0 hours and 23.5 hours after the start of the culture, the absorbance ($OD_{660}$) of the culture medium was measured. The measurement results are shown in Table 1.

Reference Example 1

Preparation of *Brevibacterium flavum* MJ233/PC-4/ΔLDH Strain (Preparation of Pyruvate Carboxylase (PC)-Enhanced Strain)
(A) Extraction of Genomic DNA from *Brevibacterium flavum* MJ233 Strain In 10 mL of A medium [2 g of urea, 7 g of $(NH_4)_2SO_4$, 0.5 g of $KH_2PO_4$, 0.5 g of $K_2HPO_4$, 0.5 g of $MgSO_4.7H_2O$, 6 mg of $FeSO_4.7H_2O$, 6 mg of $MnSO_4.4-5H_2O$, 200 μg of biotin, 100 μg of thiamine, 1 g of yeast extract, 1 g of casamino acid and 20 g of glucose; dissolved in 1 L of distilled water], *Brevibacterium flavum* MJ-233 strain was cultured until the late stage of logarithmic growth phase, and the resulting bacterial cells were collected by centrifugation (10,000 g, 5 minutes). The thus obtained bacterial cells were suspended in 0.15 mL of a 10 mM NaCl/20 mM Tris buffer (pH 8.0)/1 mM EDTA.2Na solution containing lysozyme at a concentration of 10 mg/mL. Then, proteinase K was added to the thus obtained suspension to a final concentration of 100 μg/mL and the resultant was incubated at 37° C. for 1 hour. Thereafter, sodium dodecyl sulfate was further added to a final concentration of 0.5% and the resultant was incubated at 50° C. for 6 hours to perform bacteriolysis. To the resulting lysate, an equivalent amount of a phenol/chloroform solution was added. After gently shaking the resultant at room temperature for 10 minutes, the whole amount thereof was centrifuged (5,000 G, 20 minutes, 10 to 12° C.) and a supernatant fraction was recovered. Then, after adding sodium acetate to the thus recovered fraction to a concentration of 0.3 M, a double amount of ethanol was further added and the resultant was mixed. The resulting mixture was centrifuged (15,000 G, 2 minutes) to recover precipitates, which were then washed with 70% ethanol and air-dried. To the thus obtained DNA, 5 mL of a 10 mM Tris buffer (pH 7.5)/1 mM EDTA.2Na solution was added, and the resultant was left to stand at 4° C. overnight and then used as a template DNA in the later PCR.
(B) Construction of Plasmid for Substitution of PC Gene Promoter A DNA fragment of the N-terminal region of the pyruvate carboxylase gene originated from the *Brevibacterium flavum* MJ233 strain was obtained by performing PCR using the DNA prepared in the above-described (A) as a template and synthetic DNAs (SEQ ID NOs:19 and 20) which were designed based on the sequence of the pyruvate carboxylase gene of the *Corynebacterium glutamicum* ATCC13032 strain whose entire genomic sequence has been reported (GenBank Accession No. BA000036). It is noted here that the DNA shown in SEQ ID NO:19 was phosphorylated at the 5'-end. The composition of the reaction solution was as follows: 1 μL of the template DNA, 0.2 μL of PfxDNA polymerase (manufactured by Invitrogen Corporation), 1-fold concentration of the attached buffer, 0.3 μM of each primer, 1 mM $MgSO_4$ and 0.25 μM dNTPs were mixed and the total volume was adjusted to 20 μL. The reaction temperature conditions were as follows: a DNA thermal cycler (PTC-200, manufactured by MJ Research Inc.) was used and a cycle of 94° C. for 20 seconds, 60° C. for 20 seconds and 72° C. for 1 minute was repeated 35 times. It is noted here, however, that the reaction solution was retained at 94° C. for 1 minute and 20 seconds in the first cycle and at 72° C. for 4 minutes in the final cycle. The resulting amplification products were verified by separating them by 0.75% agarose gel electrophoresis (SeaKem GTG agarose; manufactured by FMC BioProducts) and then visualizing with ethidium bromide staining. As a result, a fragment of about 0.9 kb was detected. The DNA fragment of interest was recovered from the gel using QIAQuick Gel Extraction Kit (manufactured by QIAGEN) as a PC gene N-terminal fragment.

Meanwhile, a TZ4 promoter fragment which is originated from the *Brevibacterium flavum* MJ233 strain and constitutively highly expressed was prepared by performing PCR using the plasmid pMJPC1 (JP 2005-95169A) as a template and the synthetic DNAs shown in SEQ ID NOs:21 and 22. It is noted here that the DNA shown in SEQ ID NO:22 was phosphorylated at the 5'-end. The composition of the reaction solution was as follows: 1 μL of the template DNA, 0.2 μL of PfxDNA polymerase (manufactured by Invitrogen Corporation), 1-fold concentration of the attached buffer, 0.3 μM of each primer, 1 mM $MgSO_4$ and 0.25 μM dNTPs were mixed and the total volume was adjusted to 20 μL. The reaction temperature conditions were as follows: a DNA thermal cycler (PTC-200, manufactured by MJ Research Inc.) was used and a cycle of 94° C. for 20 seconds, 60° C. for 20 seconds and 72° C. for 30 seconds was repeated 25 times. It is noted here, however, that the reaction solution was retained at 94° C. for 1 minute and 20 seconds in the first cycle and at 72° C. for 3 minutes in the final cycle. The resulting amplification products were verified by separating them by 1.0% agarose gel electrophoresis (SeaKem GTG agarose; manufactured by FMC BioProducts) and then visualizing with ethidium bromide staining. As a result, a fragment of about 0.5 kb was detected. The DNA fragment of interest was recovered from the gel using QIAQuick Gel Extraction Kit (manufactured by QIAGEN) as a TZ4 promoter fragment.

The thus obtained PC gene N-terminal fragment and TZ4 promoter fragment were mixed and ligated with each other using Ligation Kit ver. 2 (manufactured by Takara Shuzo Co., Ltd.). Then, the resultant was digested with a restriction enzyme PstI and the resulting fragments were separated by 1.0% agarose gel electrophoresis (SeaKem GTG agarose; manufactured by FMC BioProducts). A DNA fragment of about 1.0 kb was recovered by using QIAQuick Gel Extraction Kit (manufactured by QIAGEN) as TZ4 promoter::PC gene N-terminal fragment. Further, this DNA fragment was mixed with a DNA prepared by digesting *Escherichia coli* plasmid pHSG299 (manufactured by Takara Shuzo Co., Ltd.) with PstI and they were ligated with each other using Ligation Kit ver. 2 (manufactured by Takara Shuzo Co., Ltd.). Using the thus obtained plasmid DNA, *Escherichia coli* (DH5α strain) was transformed. The recombinant *Escherichia coli* obtained in this manner was then spread onto an LB agar medium containing 50 μg/mL of kanamycin and 50 μg/mL of X-Gal. A clone which formed a white colony on this medium was cultured in a liquid medium by a conventional method and a plasmid DNA was then purified. The thus obtained plasmid DNA was digested with a restriction enzyme PstI. As a result, an insert fragment of about 1.0 kb was detected and this plasmid was named "pMJPC17.1".

A DNA fragment of a 5'-upstream region of the pyruvate carboxylase gene originated from the *Brevibacterium flavum* MJ233 strain was obtained by performing PCR using the DNA prepared in the above-described (A) as a template and synthetic DNAs (SEQ ID NOs:23 and 24) which were designed based on the sequence of the pyruvate carboxylase gene of the *Corynebacterium glutamicum* ATCC 13032 strain whose entire genomic sequence has been reported (GenBank Accession No. BA000036). The composition of the reaction solution was as follows: 1 μL of the template DNA, 0.2 μL of PfxDNA polymerase (manufactured by Invitrogen Corporation), 1-fold concentration of the attached buffer, 0.3 µM of each primer, 1 mM MgSO$_4$ and 0.25 µM dNTPs were mixed and the total volume was adjusted to 20 µL. The reaction temperature conditions were as follows: a DNA thermal cycler (PTC-200, manufactured by MJ Research Inc.) was used and a cycle of 94° C. for 20 seconds, 60° C. for 20 seconds and 72° C. for 30 seconds was repeated 35 times. It is noted here, however, that the reaction solution was retained at 94° C. for 1 minute and 20 seconds in the first cycle and at 72° C. for 5 minutes in the final cycle. The resulting amplification products were verified by separating them by 1.0% agarose gel electrophoresis (SeaKem GTG agarose; manufactured by FMC BioProducts) and then visualizing with ethidium bromide staining. As a result, a fragment of about 0.7 kb was detected. The DNA fragment of interest was recovered from the gel using QIAQuick Gel Extraction Kit (manufactured by QIAGEN). The thus recovered DNA fragment was phosphorylated at the 5'-end with T4 Polynucleotide Kinase (manufactured by Takara Shuzo Co., Ltd.) and then ligated to the SmaI site of the *Escherichia coli* vector pUC119 (manufactured by Takara Shuzo Co., Ltd.) using Ligation Kit ver. 2 (manufactured by Takara Shuzo Co., Ltd.). Using the thus obtained plasmid DNA, *Escherichia coli* (DH5α strain) was transformed. The recombinant *Escherichia coli* obtained in this manner was then spread onto an LB agar medium containing 50 µg/mL of ampicillin and 50 µg/mL of X-Gal. A clone which formed a white colony on this medium was cultured in a liquid medium by a conventional method and a plasmid DNA was then purified. Thereafter, the thus obtained plasmid DNA was subjected to PCR using the synthetic DNAs shown in SEQ ID NOs:25 and 24 as primers. The composition of the reaction solution was as follows: 1 ng of the above-described plasmid, 0.2 µL of Ex-Taq DNA polymerase (manufactured by Takara Shuzo Co., Ltd.), 1-fold concentration of the attached buffer, 0.2 µM of each primer and 0.25 µM dNTPs were mixed and the total volume was adjusted to 20 µL. The reaction temperature conditions were as follows: a DNA thermal cycler (PTC-200, manufactured by MJ Research Inc.) was used and a cycle of 94° C. for 20 seconds, 60° C. for 20 seconds and 72° C. for 50 seconds was repeated 20 times. It is noted here, however, that the reaction solution was retained at 94° C. for 1 minute and 20 seconds in the first cycle and at 72° C. for 5 minutes in the final cycle. As a result of verifying the presence or absence of inserted DNA fragment in this manner, a plasmid which was found to contain an amplification product of about 0.7 kb was selected and named "pMJPC5.1".

Figure 2:
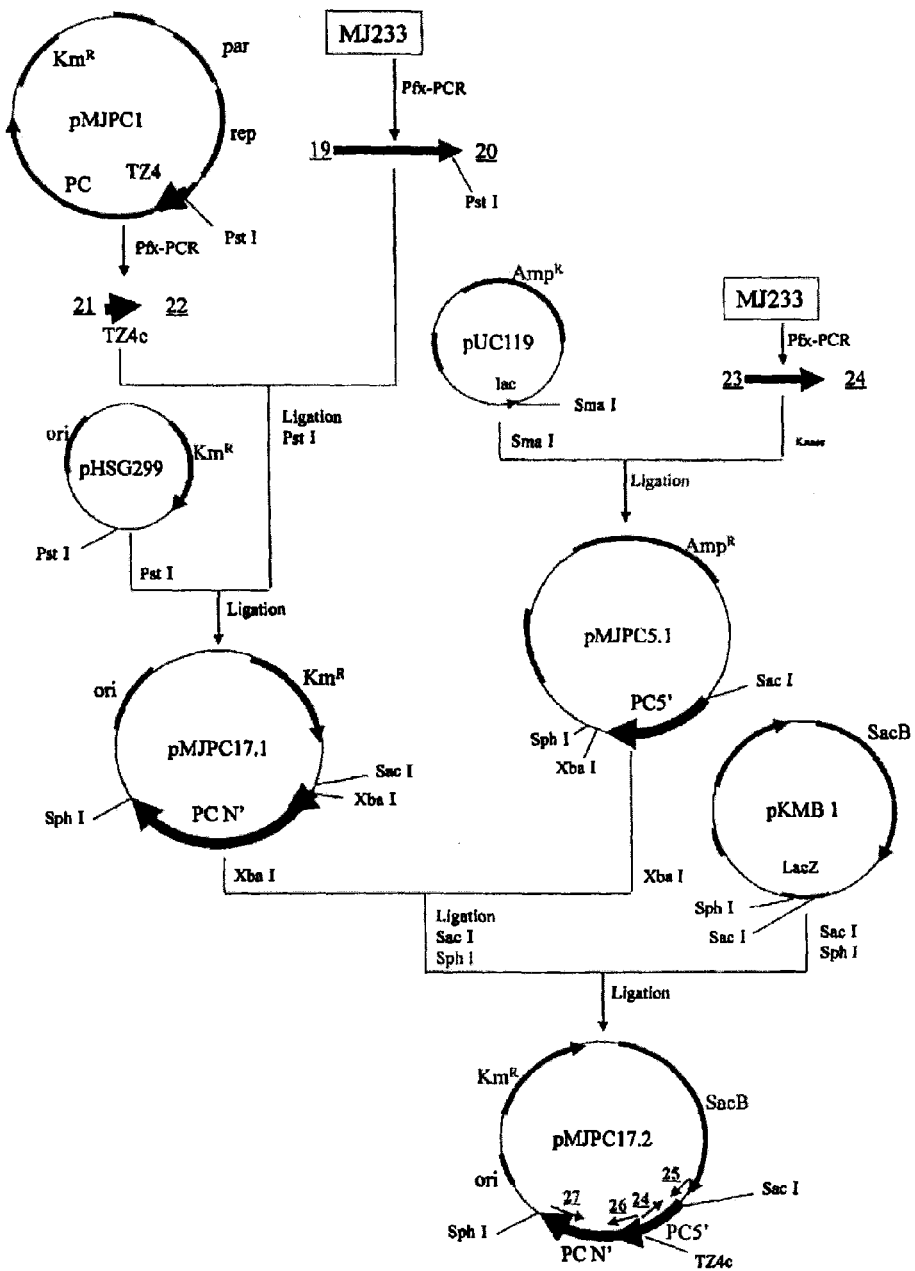
FIG. 2 is a diagram illustrating the procedures for constructing a plasmid pMJPC17.2. The underlined numbers indicate the primers having the sequence shown in the corresponding SEQ ID NOs.

Then, the thus obtained plasmids pMJPC17.1 and pMJPC5.1 were each digested with an enzyme XbaI. Thereafter, the resultants were mixed and ligated using Ligation Kit ver. 2 (manufactured by Takara Shuzo Co., Ltd.). Then, the resultant was digested with restriction enzymes SacI and SphI and the resulting fragments were separated by 0.75% agarose gel electrophoresis (SeaKem GTG agarose; manufactured by FMC BioProducts). A DNA fragment of about 1.75 kb was recovered by using QIAQuick Gel Extraction Kit (manufactured by QIAGEN). The thus obtained DNA fragment, in which the TZ4 promoter was inserted between the 5'-upstream region and the N-terminal region of the PC gene, was mixed with a DNA prepared by digesting the plasmid pKMB1 (JP 2005-95169A) containing sacB gene with restriction enzymes SacI and SphI, and these DNAs were ligated with each other using Ligation Kit ver. 2 (manufactured by Takara Shuzo Co., Ltd.). Using the thus obtained plasmid DNA, *Escherichia coli* (DH5a strain) was transformed. The recombinant *Escherichia coli* obtained in this manner was then spread onto an LB agar medium containing 50 µg/mL of kanamycin and 50 µg/mL of X-Gal. A clone which formed a white colony on this medium was cultured in a liquid medium by a conventional method and a plasmid DNA was then purified. The thus obtained plasmid DNA was digested with restriction enzymes SacI and SphI. As a result, an insert fragment of about 1.75 kb was detected and this plasmid was named "pMJPC17.2" (FIG. 2).

(C) Preparation of PC-Enhanced Strain

A plasmid DNA to be used for transformation of the *Brevibacterium flavum* MJ233/ΔLDH (lactate dehydrogenase gene-disrupted strain: JP 2005-95169A) was prepared once again from *Escherichia coli* JM 110 strain which was transformed with the plasmid DNA of pMJPC17.2 by a calcium chloride method (Journal of Molecular Biology, 53, p 159, 1970). The transformation of the *Brevibacterium flavum* MJ233/ΔLDH strain was carried out by an electric pulse method (Res. Microbiol., vol. 144, p. 181-185, 1993), and the resulting transformant was spread onto an LBG agar medium containing 25 µg/mL of kanamycin [10 g of tryptone, 5 g of yeast extract, 5 g of NaCl, 20 g of glucose and 15 g of ager; dissolved in 1 L of distilled water]. In the strain that grew on this medium, since the pMJPC17.2 is a plasmid which cannot be replicated in the cells of the *Brevibacterium flavum* MJ233 strain, as a result of homologous recombination between the PC gene of the plasmid and the PC gene on the genome of the *Brevibacterium flavum* MJ233 strain, a kanamycin-resistant gene and a sacB gene that are originated from the plasmid are expected to have been inserted in the genome. Then, the above-described homologous recombinant strain was cultured in a liquid LBG medium containing 25 µg/mL of kanamycin. This culture solution was then, in an amount corresponding to about 1,000,000 cells, spread onto 10% sucrose-containing LBG medium. As a result, several tens of strains, which were believed to have become sucrose-insensitive due to the loss of sacB gene caused by the second homologous recombination, were obtained. These strains obtained in this manner included those in which the TZ4 promoter originated from pMJPC17.2 was inserted in the upstream of the PC gene, as well as those which were converted back to be of a wild-type. Whether the PC gene is of a promoter-substituted type or a wild type can be easily verified by directly subjecting cells obtained by culturing in a liquid LBG medium to PCR and then detecting the PC gene. When the TZ4 promoter and the PC gene are analyzed by using the primers for PCR amplification (SEQ ID NOs: 26 and 27), a DNA fragment of 678 bp should be observed for the promoter-substituted type. As a result of analyzing the strain which was transformed to be sucrose-insensitive by the above-described method, a strain inserted with the TZ4 promoter was selected and this strain was named "*Brevibacterium flavum* MJ233/PC-4/ΔLDH".

(D) Measurement of Pyruvate Carboxylase Activity

The transformed *Brevibacterium flavum* MJ233/PC-4/ΔLDH strain obtained in the above-described (C) was cultured overnight in 100 mL of A medium containing 2% glucose. After recovering the resulting bacterial cells, the cells were washed with 50 mL of 50 mM potassium phosphate buffer (pH 7.5) and then resuspended in 20 mL of buffer having the same composition. This suspension was homogenized by using Sonifier 350 (manufactured by Branson Ultrasonics Corporation) and centrifuged to obtain a supernatant as a cell-free extract. Using the thus obtained cell-free extract, the activity of pyruvate carboxylase was measured. The measurement of the enzyme activity was carried out by allowing a reaction to take place at 25° C. in a reaction solution containing 100 mM Tris/HCl buffer (pH 7.5), 0.1 mg/10 ml biotin, 5 mM magnesium chloride, 50 mM sodium bicarbonate, 5 mM sodium pyruvate, 5 mM sodium adenosine triphosphate, 0.32 mM NADH, 20 units/1.5 ml malate dehydrogenase (manufactured by Wako Pure Chemical Industries, Ltd.; originated from yeast) and the enzyme. Here, "1 U" was defined as an amount of the enzyme required for catalyzing a 1-µmol reduction of NADH in a period of 1 minute. The cell-free extract in which the expression of pyruvate carboxylase was enhanced had a specific activity of 0.1 U/mg-protein. It is noted here that the cells obtained by culturing the parent strain, MJ233/ΔLDH strain, in the same manner had a specific activity of below the detection limit of this enzyme activity measuring method.

Comparative Example 1

Evaluation of Growth on Synthetic Medium

The evaluation was carried out in the same manner as in Example 1 except that the *Brevibacterium flavum* MJ233/PC-4/ΔLDH strain was used in place of the *Brevibacterium flavum* MJ233/ΔQsuB/PC-4/ΔLDH strain. It is noted here that kanamycin was not added during the culture. In the same manner as in Example 1, the absorbance ($OD_{660}$) of the culture medium was measured at 1.5 hours, 3.1 hours, 5.0 hours, 7.0 hours, 9.0 hours, 11.0 hours and 23.5 hours after the start of the culture. The measurement results are shown in Table 1.

TABLE 1

| Culturing time [h] | Example 1 $OD_{660}$ | Comparative Example 1 $OD_{660}$ |
|---|---|---|
| 1.5 | 1.16 | 1.30 |
| 3.1 | 1.82 | 2.03 |
| 5.0 | 2.98 | 3.42 |
| 7.0 | 4.55 | 4.85 |
| 9.0 | 6.88 | 7.20 |
| 11.0 | 8.27 | 8.29 |
| 23.5 | 9.01 | 8.75 |

From the results shown in Table 1, it was confirmed that the disruption of the qsuB gene does not adversely affect the growth on the synthetic medium.

Example 2

Production of Succinic Acid by QsuB-disrupted Strain

A medium [4 g of urea, 14 g of $(NH_4)_2SO_4$, 0.5 g of $KH_2PO_4$, 0.5 g of $K_2HPO_4$, 0.5 g of $MgSO_4·7H_2O$, 20 mg of $FeSO_4·7H_2O$, 20 mg of $MnSO_4·H_2O$, 200 µg of D-biotin, 200 µg of thiamine hydrochloride, 1 g of yeast extract and 1 g of casamino acid; dissolved in 1 L of distilled water] in an amount of 100 mL was placed in a 500-mL Erlenmeyer flask and heat-sterilized at 120° C. for 20 minutes. The medium was then cooled to room temperature and 8 mL of 50% aqueous glucose solution which had been sterilized in advance and 50 µL of filter-sterilized 5% aqueous kanamycin solution were added thereto. The QsuB-disrupted strain (*Brevibacterium flavum* MJ233/ΔQsuB/PC-4/ΔLDH) prepared in Example 1 was inoculated to the resulting medium to an absorbance ($OD_{660}$) of 1.0 and cultured at 30° C.

At 12 hours after the start of the culture, 3.16 g of ammonium bicarbonate was added and allowed to react with the cells with the mouth of the Erlenmeyer flask being tightly closed with a parafilm. After the reaction, the cells were removed by centrifugation at 10,000 G for 5 minutes and the organic acid concentration of the resulting supernatant was analyzed by the above-described measurement method. As a result, the amount of protocatechuic acid generated in the culture medium after the reaction was found to be 12 ppm with respect to the amount of the generated succinic acid. The succinic acid concentration of the culture medium after the reaction was 14.3 g/L.

Comparative Example 2

The evaluation was carried out in the same manner as in Example 2 except that the pyruvate carboxylase (PC)-enhanced strain (*Brevibacterium flavum* MJ233/PC-4/ΔLDH) prepared in Reference Example 1 was used in place of the QsuB-disrupted strain (*Brevibacterium flavum* MJ233/ΔQsuB/PC-4/ΔLDH) prepared in Example 1. It is also noted here that kanamycin was not added during the culture.

As a result of analyzing the organic acid concentration of the resulting culture medium in the same manner as in Example 2, the amount of protocatechuic acid generated in the culture medium after the reaction was found to be 564 ppm with respect to the amount of the generated succinic acid. The succinic acid concentration of the culture medium after the reaction was 14.5 g/L.

From these results, it was confirmed that the disruption of the qsuB gene markedly reduces the by-production of protocatechuic acid.

Experimental Example 1

Model Experiment: Production of Polymer Using Succinic Acid Obtained in Comparative Example 2

(Preparation of Succinic Acid-Containing Solution A)

A food additive-grade succinic acid (manufactured by Kawasaki Kasei Chemical Ltd.) and protocatechuic acid (manufactured by Wako Pure Chemical Industries, Ltd.) were dissolved in hot water of 80° C. to prepare a solution A having a succinic acid concentration of 35% by weight and a protocatechuic acid concentration of 197 ppm (succinic acid: 564 ppm).

(Crystallization)

The thus obtained succinic acid-containing solution A was stored in an aqueous succinic acid solution feed tank. The succinic acid-containing solution A was then fed to a crystallization bath, whose jacket temperature was controlled at 80° C. by a program-controlled circulation thermostat bath, by means of a stock solution feed pump until the liquid level reached a prescribed point. Once the liquid level reached the prescribed point, while stirring the solution with paddle blades at a rate of 500 rotation/minutes, the hot water being supplied to the jacket of the crystallization bath was cooled to 20° C. over a period of about one hour, thereby lowering the temperature inside the crystallization bath to 20° C. After the crystallization bath was cooled to 20° C., while maintaining this temperature, the stirring was continued for another one hour.

Thereafter, while controlling the temperature of the cold water being passed through the jacket so that the temperature inside the crystallization bath was maintained at 20° C., the succinic acid-containing solution A was continuously fed at a rate of 250 ml/minute and a solid succinic acid-containing slurry was intermittently removed into a slurry recovery tank once every 15 minutes or so in order to keep the volume of the succinic acid-containing slurry in the crystallization bath almost constant. The removed succinic acid-containing slurry was vacuum-filtered to be separated into a succinic acid wet cake and a crystallization mother liquor every time the slurry was removed.

This continuous crystallization operation was continued for 24 hours and succinic acid wet cakes that were obtained after 6 hours or later from the start of the continuous crystallization operation were recovered. The thus recovered succinic acid wet cakes were suspended and washed in a 5-times weight of 10° C. cold water. Thereafter, the resulting slurry was vacuum-filtered to obtain a succinic acid wet cake. This wet cake was then vacuum-dried at 80° C. to recover succinic acid.

The thus obtained succinic acid was dissolved in 80° C. hot water to a succinic acid concentration of 35% by weight and the resulting solution was once again subjected to continuous crystallization for 7 hours by the above-described crystallization operation. Succinic acid wet cakes that were obtained between 6 and 7 hours in the continuous crystallization operation were suspended and washed in a 5-times weight of 10° C. cold water. Thereafter, the resulting slurry was vacuum-filtered to obtain a succinic acid wet cake. This wet cake was then vacuum-dried at 80° C. to recover succinic acid in an amount of 55 g. As a result of quantifying the aromatic carboxylic acid contained in the thus obtained succinic acid, it was found that the succinic acid contained 3.6 ppm of protocatechuic acid.

(Production of Polymer)

To a reaction vessel equipped with a stirring device, a nitrogen inlet, a heating apparatus, a thermometer and a pressure reduction vent, 100 parts by weight of the succinic acid obtained by the above-described crystallization operation was fed as a starting material along with 99.2 parts by weight of industrial-grade 1,4-butanediol (manufactured by Mitsubishi Chemical Corporation) and 0.38 parts by weight of malic acid (a total amount of 0.33 mol % with respect to the amount of the succinic acid), and the inside of the system was replaced to be a nitrogen atmosphere with nitrogen under reduced pressure. Then, with stirring, the inside of the system was heated to 230° C. over a period of 1 hour and then reaction was performed at this temperature for 1 hour. To this reaction solution, a catalyst solution prepared by the below-described method was added in such an amount that the amount of titanium atom became 50 ppm with respect to the amount of the resulting polyester theoretically calculated based on the amount of the starting material used.

To a 500-cm$^3$ eggplant-shaped glass flask equipped with a stirring device, 62.0 g of magnesium acetate tetrahydrate was placed and 250 g of anhydrous ethanol (purity: not less than 99% by weight) was added thereto. Further, 35.8 g of ethyl acid phosphate (mixed weight ratio of monoester body and diester body=45:55) was added and the resulting mixture was stirred at 23° C. After 15 minutes, complete dissolution of magnesium acetate was confirmed and then 75.0 g of tetra-n-butyl titanate was added. The resulting mixture was stirred for another 10 minutes to obtain a uniform mixed solution. The thus obtained mixed solution was transferred to a 1,000-cm$^3$ eggplant-shaped flask, which was then placed in a 60° C. oil bath to concentrate the mixed solution under reduced pressure using an evaporator. After 1 hour, most of ethanol was distilled out, and a semi-transparent viscous liquid was remained. Then, the temperature of the oil bath was raised to 80° C. to further concentrate the semi-transparent viscous liquid under a reduced pressure of 5 Torr. The viscous liquid gradually changed into the form of powder from the surface and completely powderized after 2 hours. Thereafter, the system was brought back to normal pressure using nitrogen and cooled to room temperature, thereby obtaining a pale yellow powder in an amount of 108 g. The thus obtained catalyst was subjected to metal element analysis and, as a result, it was found that the catalyst contained 10.3% by weight of titanium atom, 6.8% by weight of magnesium atom and 7.8% by weight of phosphorus atom and the molar ratios thereof were: T/P=0.77 and M/P=1.0. Furthermore, this powder-form catalyst was dissolved in 1,4-butanediol so that the titanium atom content became 34,000 ppm.

After adding the resulting catalyst solution, the inner temperature of the reaction vessel was slowly raised to 250° C. and, at the same time, the pressure was reduced to 0.06×10$^3$ Pa over a period of 2 hours. The reaction was allowed to proceed for 2.5 hours at this reduced pressure, thereby producing a polyester. When the thus obtained polyester was evaluated in accordance with the above-described polymer evaluation method, it was found that the Y.I. value was 10, the reduced viscosity (ηsp/c) was 2.3 and the amount of terminal carboxyl group was 24 eq/ton.

Experimental Example 2

Model Experiment (1): Production of Polymer Using Succinic Acid Obtained in Example 2

(Preparation of Succinic Acid-Containing Solution B, Crystallization Thereof and Production of Polymer)

A food additive-grade succinic acid (manufactured by Kawasaki Kasei Chemical Ltd.) and protocatechuic acid (manufactured by Wako Pure Chemical Industries, Ltd.) were dissolved in hot water of 80° C. to prepare a solution B having a succinic acid concentration of 35% by weight and a protocatechuic acid concentration of 4.2 ppm (succinic acid: 564 ppm).

By performing the crystallization operation in the same manner as in Experimental Example 1 except that the thus obtained succinic acid-containing solution B was used, 54 g of succinic acid was recovered. As a result of quantifying the aromatic carboxylic acid contained in the thus obtained succinic acid, it was found that the succinic acid contained 0.1 ppm of protocatechuic acid.

Using the thus obtained succinic acid, a polyester was produced in the same manner as in Experimental Example 1. When this polyester was evaluated in accordance with the above-described polymer evaluation method, it was found that the Y.I. value was 5, the reduced viscosity (ηsp/c) was 2.3 and the amount of terminal carboxyl group was 24 eq/ton.

Experimental Example 3

Model Experiment (2): Production of Polymer Using Succinic Acid Obtained in Example 2

(Crystallization Using Succinic Acid-Containing Solution B and Production of Polymer)

The above-described succinic acid-containing solution B was stored in an aqueous succinic acid solution feed tank and subjected to continuous crystallization operation for 24 hours in the same manner as in Experimental Example 1. Succinic acid wet cakes that were obtained after 6 hours or later from the start of the continuous crystallization operation were recovered. The thus recovered succinic acid wet cakes were suspended and washed in a 5-times weight of 10° C. cold water. Thereafter, the resulting slurry was vacuum-filtered to obtain a succinic acid wet cake. This wet cake was then vacuum-dried at 80° C. to recover succinic acid. As a result of quantifying the aromatic carboxylic acid contained in the thus obtained succinic acid, it was found that the succinic acid contained 1 ppm of protocatechuic acid.

Using the thus obtained succinic acid, a polyester was produced in the same manner as in Experimental Example 1. When this polyester was evaluated in accordance with the above-described polymer evaluation method, it was found that the Y.I. value was 6, the reduced viscosity (ηsp/c) was 2.3 and the amount of terminal carboxyl group was 24 eq/ton.

Experimental Example 4

Preparation of Succinic Acid-Containing Solution C, Crystallization Thereof and Production of Polymer A food additive-grade succinic acid (manufactured by Kawasaki Kasei Chemical Ltd.) and diammonium succinate (manufactured by Wako Pure Chemical Industries, Ltd.) were dissolved in hot water of 80° C. to prepare a solution C having a succinic acid concentration of 35% by weight and an ammonium ion concentration of 175 ppm (succinic acid: 5,000 ppm).

By performing the crystallization operation in the same manner as in Experimental Example 1 except that the thus obtained succinic acid-containing solution C was used, 60 g of succinic acid was recovered. As a result of quantifying the ammonium ion contained in the thus obtained succinic acid, it was found that the succinic acid contained ammonium ion in an amount of not higher than the detection limit (0.1 ppm).

Using the thus obtained succinic acid, a polyester was produced in the same manner as in Experimental Example 1. When this polyester was evaluated in accordance with the above-described polymer evaluation method, it was found that the Y.I. value was 5, the reduced viscosity (ηsp/c) was 2.3 and the amount of terminal carboxyl group was 24 eq/ton.

From the results of Experimental Examples 1 to 4, it is understood that the method of producing a polymer according to the present invention can reduce the coloration of resulting polymers.

Experimental Example 5

With reference to the method described in the below-listed References, uvitonic acid was synthesized. That is, 10 ml (2 mol) of an ammonia-ethanol solution was placed in a 100-ml three-necked flask and, while stirring the solution with a magnetic stirrer under $N_2$, 0.91 g (0.01 mol) of pyruvic acid was added thereto dropwise at room temperature. The resulting solution slightly generated heat and white precipitates were formed after a few minutes. Then, the thus obtained white precipitates were washed with ethanol.

REFERENCES

1. J. Org. Chem., 50, 1688 (1985)
2. Biochimie, 54, 115 (1972)
3. Vegetable Physiology and Agriculture
4. J. Org. Chem., 47, 1148 (1982)

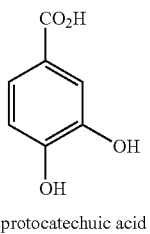
protocatechuic acid

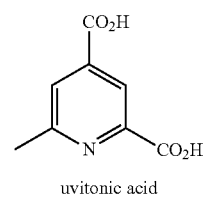
uvitonic acid

Using a food additive-grade succinic acid (manufactured by Kawasaki Kasei Chemical Ltd.), polyesters were produced in the same manner as in the above-described Experimental Example 1, except that protocatechuic acid (manufactured by Wako Pure Chemical Industries, Ltd.) or the uvitonic acid produced by the above-described method was added in the amount shown in Table 2. The Y.I. value of the thus obtained respective polyesters was measured in accordance with the above-described polymer evaluation method. The measurement results are shown in Table 2 below.

TABLE 2

| | Concentration of protocatechuic acid with respect to the amount of succinic acid at the time of feeding (ppm) | | |
|---|---|---|---|
| | 0 | 10 | 57 |
| Y.I. value | 5 | 17 | 40 |
| | Concentration of uvitonic acid with respect to the amount of succinic acid at the time of feeding (ppm) | | |
| | 0 | 27 | 76 |
| Y.I. value | 5 | 10 | 17 |

From the above results, it is understood that protocatechuic acid and uvitonic acid, which are aromatic carboxylic acids, are substances that cause coloration of a polymer.

INDUSTRIAL APPLICABILITY

In general, succinic acid is produced from a petrochemically-derived material and used in a wide variety of applications. For these applications, succinic acid derived from a bioresource can also be preferably used in the same manner. For example, such succinic acid can be used as: a raw material of 1,4-butanediol, 2-pyrrolidine, succinimide, maleic anhydride, itaconic acid, aspartic acid, maleic acid, fumaric acid, hydroxysuccinimide, maleimide, 4-aminobutyric acid, γ-aminobutyric acid, tetrahydrofuran, acrylic acid, succinic esters such as dimethyl succinate and diethyl succinate, pyrrolidone, N-methylpyrrolidone and the like; as a starting material of polymer compounds such as polyester, polyurethane and polyamide and products thereof; a food additive such as an acidulant, a flavoring agent, a brewing agent or a processed food additive; a bubble bath component; a synthetic material or component of pharmaceuticals and agricultural chemicals such as plant growth inhibitors, herbicides, antibacterial agents, pesticides and mosquito attractants; a material or component of mouthwash, cosmetics and the like; a material or component of products that are used for photographs and printings; a material or component of adhesives and sealants such as high-temperature welding fluxes and alumite-treated surface adhesives; a material or component for metal processing such as powder nickel production, steel grinding bath, metal processing and washing solvents and binders for metal sintering; a material or component of solders and welding fluxes; a material or component of auxiliary agents that are used in the production of ceramics, inorganics and the like, such as production of a porous titanium oxide, production of boehmite, production of photocatalytic coating agents and production of ceramics; a material or component of detergents and the like; a material or component of bleaches and the like; a material or component of dyeing aids; a material or component of electrolyte solvents, plating solutions and the like; a material or component of deodorants, air cleaning agents and the like; a material of bioabsorbable compounds used for bioabsorbable surgical sutures and the like; a material or component of treatment agents, softeners and the like of textile goods; a material or component of fluxes, solvents and the like; a material or component of water-soluble paint solvents; a material or component of biodegradable resins; a material or component of sealants such as odor-free sealants; a material or component of anticorrosive agents that are used in coating of steel products, copper products and alloy metal products, freeze proofing, metal processing, lead for perchloric acid, boiler water treatment and the like; a material or component for synthesizing lubricants such as synthetic lubricants, lubricants for heat-resistant plastics and electrical contact lubricants; a material or component of solvent-removing washing agents and the like that used for resins, polymer materials and the like; a material or component of products that are used in the textile industry, dry cleaning and the like; a material or component of pigments, dyes, inks and the like that are used in, for example, ink solvents, deinking agents, automobile top-coating agents, insulating varnishes, powder paints, inks for three-dimensional printing, photosetting-type paints, photosetting ink compositions, nanoparticle inks, inks for ink jet printers, printing screen washing agents, organic semiconductor solutions, inks for color filter production, toners, quinacridone pigment production, succinyl succinate production and dye intermediates; a material or component of oxygen-containing-type diesel fuels and the like; a material or component of cement admixtures, cement treatment agents and the like; a material or component of engine cleaners and the like; a material or component of petroleum refinery solvents and the like; a material or component of oil and natural gas extraction auxiliary agents such as proppant compositions and those auxiliary agents that are used for removal of precipitation filter cakes; a material or component of those products relating to natural gas production, such as natural gas dehydrating solvents; a material or component of construction materials such as low-dust concrete flooring materials and asphalt pavement materials; and a material or component of ink solvents and deinking agents.

DESCRIPTION OF SEQUENCES

SEQ ID NO:1 (nucleotide sequence of a primer)
SEQ ID NO:2 (nucleotide sequence of a primer)
SEQ ID NO:3 (nucleotide sequence of a primer)
SEQ ID NO:4 (nucleotide sequence of a primer)
SEQ ID NO:5 (nucleotide sequence of a primer)
SEQ ID NO:6 (nucleotide sequence of a primer)
SEQ ID NOs:7 and 8 (nucleotide sequence of the aroF gene and amino acid sequence encoded thereby)
SEQ ID NOs:9 and 10 (nucleotide sequence of the aroG gene and amino acid sequence encoded thereby)
SEQ ID NOs:11 and 12 (nucleotide sequence of the aroB gene and amino acid sequence encoded thereby)
SEQ ID NOs:13 and 14 (nucleotide sequence of the qsuC gene and amino acid sequence encoded thereby)
SEQ ID NOs:15 and 16 (nucleotide sequence of the qsuB gene and amino acid sequence encoded thereby)
SEQ ID NOs:17 and 18 (nucleotide sequence of the qsuD gene and amino acid sequence encoded thereby)
SEQ ID NO:19 (nucleotide sequence of a polymer used in the construction of pMJPC17.2)
SEQ ID NO:20 (nucleotide sequence of a polymer used in the construction of pMJPC17.2)
SEQ ID NO:21 (nucleotide sequence of a polymer used in the construction of pMJPC17.2)
SEQ ID NO:22 (nucleotide sequence of a polymer used in the construction of pMJPC17.2)
SEQ ID NO:23 (nucleotide sequence of a polymer used in the construction of pMJPC17.2)
SEQ ID NO:24 (nucleotide sequence of a polymer used in the construction of pMJPC17.2)
SEQ ID NO:25 (nucleotide sequence of a polymer used in the construction of pMJPC17.2)
SEQ ID NO:26 (nucleotide sequence of a polymer used in the construction of pMJPC17.2)
SEQ ID NO:27 (nucleotide sequence of a polymer used in the construction of pMJPC17.2)

The invention claimed is:

1. A Coryneform bacterium, which has an ability to produce an organic acid and has been modified so that at least one enzyme activity selected from the group consisting of dehydroquinate synthase activity, dehydroquinate dehydratase activity and dehydroshikimate dehydratase activity is reduced as compared to an unmodified strain, and the production of an aromatic carboxylic acid from a fermentable sugar is thereby reduced, wherein the at least one enzyme activity is reduced by disrupting a gene encoding the at least one enzyme, mutating a gene encoding the at least one enzyme, or modifying an expression control sequence of a gene encoding the at least one enzyme.

2. The Coryneform bacterium according to claim 1, which has been modified so that the dehydroshikimate dehydratase activity is reduced.

3. The Coryneform bacterium according to claim 2, wherein said gene encoding dehydroshikimate dehydratase is a DNA comprising the nucleotide sequence shown in SEQ ID NO: 15 or a DNA which hybridizes with a complementary sequence of said nucleotide sequence shown in SEQ ID NO: 15 under stringent conditions comprising hybridization under a salt concentration equivalent to 1×SSC and 0.1% SDS at 60° C. and encodes a protein having dehydroshikimate dehydratase activity.

4. The Coryneform bacterium according to claim 1, wherein said aromatic carboxylic acid is a hydroxybenzene carboxylic acid.

5. The Coryneform bacterium according to claim 4, wherein said aromatic carboxylic acid is protocatechuic acid.

6. The Coryneform bacterium according to claim 1, wherein the at least one enzyme activity is reduced by disrupting a gene encoding the at least one enzyme.

7. The Coryneform bacterium according to claim 1, wherein the at least one enzyme activity is reduced by mutating a gene encoding the at least one enzyme.

8. The Coryneform bacterium according to claim 1, wherein the at least one enzyme activity is reduced by modifying an expression control sequence of a gene encoding the at least one enzyme.

9. A Coryneform bacterium, which has an ability to produce an organic acid and has been modified so that dehydroquinate synthase activity is reduced as compared to an unmodified strain, and the production of an aromatic carboxylic acid is thereby reduced, wherein the dehydroquinate synthase activity is reduced by disrupting a gene encoding the dehydroquinate synthase, mutating a gene encoding the dehydroquinate synthase, or modifying an expression control sequence of a gene encoding the dehydroquinate synthase.

10. The Coryneform bacterium according to claim 9, which has further been modified so that at least one additional enzyme activity selected from the group consisting of dehydroquinate dehydratase activity and dehydroshikimate dehydratase activity is reduced as compared to an unmodified strain, and the production of an aromatic carboxylic acid is thereby reduced, wherein the at least one enzyme activity is reduced by disrupting a gene encoding the at least one enzyme, mutating a gene encoding the at least one enzyme, or modifying an expression control sequence of a gene encoding the at least one enzyme.

11. The Coryneform bacterium according to claim 1, wherein the fermentable sugar is glucose, fructose, or sucrose.

12. The Coryneform bacterium according to claim 1, wherein the fermentable sugar is glucose, or sucrose.

13. A method of producing a polymer of an organic acid, which comprises performing a polymerization reaction with an organic acid obtained by allowing the Coryneform bacterium according to claim 1, an immobilized bacterium of said bacterium, a homogenate of the bacterium, or a fraction of the bacterium to act on an organic raw material.

14. The method according to claim 1, further comprising crystallizing the organic acid.

15. The method according to claim 1, wherein said aromatic carboxylic acid is a hydroxybenzene carboxylic acid.

16. The method according to claim 1, wherein said organic acid is succinic acid.

17. The method according to claim 16, wherein said polymer is a polyester or a polyamide.

18. A method of producing an organic acid, comprising allowing the Coryneform bacterium according to claim 1, an immobilized bacterium of said bacterium, a homogenate of the bacterium, or a fraction of the bacterium to act on the fermentable sugar.

19. The method according to claim 18, which is performed in an anaerobic atmosphere.

20. The method according to claim 18, wherein said organic acid is succinic acid.

21. The method according to claim 18, further comprising crystallizing said organic acid.

22. The method according to claim 18, wherein said aromatic carboxylic acid is a hydroxybenzene carboxylic acid.

* * * * *